United States Patent
Gadwood et al.

[11] Patent Number: 5,977,373
[45] Date of Patent: Nov. 2, 1999

[54] THIADIAZOLYL AND OXADIAZOLYL PHENYL OXAZOLIDINONE ANTIBACTERIAL AGENTS

[75] Inventors: Robert C. Gadwood; Lisa Marie Thomasco; David John Anderson, all of Kalamazoo, Mich.

[73] Assignee: Pharmacia & Upjohn Company, Kalamazoo, Mich.

[21] Appl. No.: 09/111,995

[22] Filed: Jul. 8, 1998

Related U.S. Application Data

[60] Provisional application No. 60/052,907, Jul. 11, 1997, and provisional application No. 60/064,746, Nov. 7, 1997.

[51] Int. Cl.$^6$ .................. C07D 417/10; C07D 413/10
[52] U.S. Cl. ................ 548/128; 548/131; 548/134; 548/136; 548/138; 548/139; 548/143
[58] Field of Search ................... 548/131, 134, 548/136, 138, 128, 139, 143

[56] References Cited

U.S. PATENT DOCUMENTS

| | | | |
|---|---|---|---|
| 4,948,801 | 8/1990 | Carlson et al. | |
| 5,043,443 | 8/1991 | Carlson et al. | |
| 5,130,316 | 7/1992 | Carlson et al. | |
| 5,254,577 | 10/1993 | Carlson et al. | |
| 5,547,950 | 8/1996 | Hutchinson | 514/252 |
| 5,565,571 | 10/1996 | Barbachyn | 546/144 |
| 5,688,792 | 11/1997 | Barbachyn | 514/235.5 |
| 5,736,545 | 4/1998 | Gadwood | 514/252 |

FOREIGN PATENT DOCUMENTS

| | | |
|---|---|---|
| 0352781 | 1/1990 | European Pat. Off. |
| WO93/09103 | 5/1993 | WIPO |
| WO96/23788 | 8/1996 | WIPO |
| WO97/09328 | 3/1997 | WIPO |
| WO97/30981 | 8/1997 | WIPO |

OTHER PUBLICATIONS

PCT/US98/09889 Unpublished PCT Application; No copy attached.

*Primary Examiner*—Robert Gerstl
*Attorney, Agent, or Firm*—Lucy X. Yang

[57] ABSTRACT

The present invention provides thiadiazolyl and oxadiazolyl phenyl oxzolidinone compounds of formula I

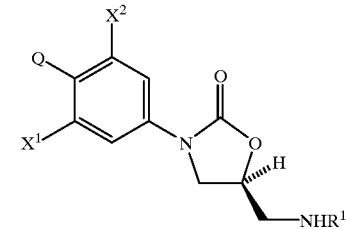

wherein Q is thiadiazolyl or oxadiazolyl;
wherein $X^1$ and $X^2$ are independently hydrogen, fluorine or chlorine; and
wherein $R^1$ is, for example, —COCH$_3$ or —COCH$_2$CH$_3$.

These compounds are useful antimicrobial agents, effective against a number of human and veterinary pathogens, including gram-positive and gram-negative aerobic bacteria.

6 Claims, No Drawings

THIADIAZOLYL AND OXADIAZOLYL PHENYL OXAZOLIDINONE ANTIBACTERIAL AGENTS

CROSS-REFERENCE TO RELATED APPLICATION

This application claims the benefit of the following provisional applications: U.S. Ser. No. 60/052,907, filed Jul. 11, 1997; U.S. Ser. No. 60/064,746, filed Nov. 7, 1997, both under 35 USC 119(e)(i).

BACKGROUND OF THE INVENTION

The subject invention discloses thiadiazolyl and oxadiazolyl phenyl oxazolidinone derivatives. The compounds are useful antimicrobial agents, effective against a number of human and veterinary pathogens, including gram-positive aerobic bacteria such as multiply-resistant staphylococci, streptococci and enterococci, as well as anaerobic organisms such as Bacteroides spp., and acid-fast organisms such as *Mycobacterium tuberculosis*.

Piperazine-containing oxazolidinonesare disclosed in International Publication No. WO93/23384, Nov. 25, 1987 (PCT/US93/03570). International Publication No. WO95/14684, Jun. 1, 1995 (PCT/US94/10582) discloses esters of the oxazolidinone, piperazine ring structures disclosed in the above PCT application. International Publication No. WO95/07271, Mar. 16, 1995 (PCT/US94/08904) discloses oxazolidinones although containing morpholine and thiomorpholine instead of the subject piperazine.

Other earlier publications in the area of oxazolidiiunes are U.S. Pat. Nos. 4,801,600; 4,921,869; EPA 0352781 (Jan. 31, 1989); and EPA 0316594 (May 24, 1989) all assigned to E. I. DuPont De Nemours and Company, which are cited here to exemplify the state of the art.

INFORMATION DISCLOSURE

International Publication No. WO 93/09103, published May 13, 1993, and corresponding U.S. Pat. No. 5,565,571, disclose substituted aryl- and heteroarylphenyl-oxazolidinones useful as antibacterial agents. Among the heteroaryl groups disclosed are groups such as imidazolyl, pyrazolyl, thiazolyl, isothiazolyl, oxazolyl, isoxazolyl and triazolyl.

International Publication No. WO96/23788, published Aug. 8, 1996, discloses nitrogen-containing heteroaromatic ring substituted phenyloxazolidinone antimicrobials. This 5-member nitrogen-containing hetero-aromatic ring has from 1 to 4 nitrogen atoms and is attached to the phenyloxazolidinone through one of the nitrogen atom.

U.S. Pat. Nos. 4,948,801; 5,043,443; 5,130,316; and 5,254,577 aminomethyloxodxazolidinyl aryl-substituted benzene derivatives useful as antibacterial agents. Among the aromatic groups disclosed are groups such as diazinyl, triazinyl, thiazolyl, oxazolyl and unsubstituted 1,2,3-thiadiazol-4-yl. These compounds do not have flanking halogens on the benzene ring.

International Publication No. WO97/30981, published Aug. 28, 1997, discloses azolyl piperazinyl phenyl oxazolidinone antibacterials. Among the five-membered ring heterocycles (i.e., azolyl rings) disclosed are groups such as thiadiazolyl, oxazdiazolyl, thiazolyl, benzothiazolyl, thiatriazolyl, imidazolyl, benzimidazolyl, triazolyl, tetrazolyl, pyrazolinyl, pyrazolyl, indazolyl, benzoisothiazolyl, isoxazolyl and benisoxazolyl. In all cases, the piperazine nitrogen atom is attached at the carbon atom of the carbon-nitrogen double bond of the heterocyclic ring.

U.S. Ser. No. 09/080,751, filed May 18, 1998 discloses oxazolidinone antibacterial agents having a thiocarbonyl functionality. It discloses the compound (S)-N-[[3-[3-fluoro-4-[4-(5-methyl-1,3,4-thiadiazol-2-yl)-1-piperazinyl]phenyl]-2-oxo-5-oxazolidinyl]methyl]thioacetamide.

SUMMARY OF THE INVENTION

The present invention provides a compound of structural formula I:

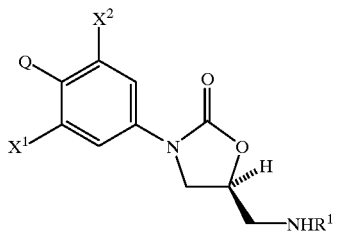

or a pharmaceutically acceptable salt thereof, wherein $R^1$ is
(a) —$COR^3$,
(b) —$COCH_2Cl$,
(c) —$COCHCl_2$,
(d) —$COCH_2F$,
(e) —$COCHF_2$,
(f) —$CO_2CH_3$,
(g) —$SO_2CH_3$,
(h) —$COCH_2OH$,
(i) —$CSR^3$,
(j) —$CSNH_2$, or
(k) —$CSNHCH_3$;

$X^1$ and $X^2$ are independently H, F, or Cl; and Q is an optionally substituted five membered ring heterocycle incorporating two nitrogen atoms and one sulfur or oxygen atom.

More specifically, in the present invention, Q is:

(a) 1,3,4-thiadiazol-2-yl:

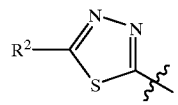

(b) 1,2,4-thiadiazol-3-yl:

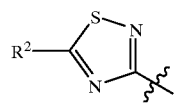

(c) 1,2,4-thiadiazol-5-yl:

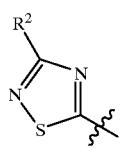

(d) 1,2,5-thiadiazol-3-yl:

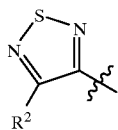
V (e) 1,2,3-thiadiazol-4-yl:

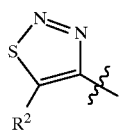
VI (f) 1,2,3-thiadiazol-5-yl:

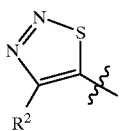
VII (g) 1,3,4-oxadiazol-2-yl:

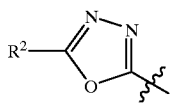
VIII (h) 1,2,4-oxadiazol-3-yl:

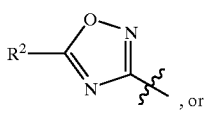
IX
, or (i) 1,2,4-oxadiazol-5-yl

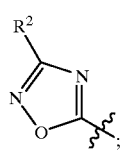
IX-A wherein $R^2$ is
(a) $R^3$—
(b) $R^4CO_2(CH_2)_n$—,
(c) $NC(CH_2)_n$—,
(d) $R^3OCO(CH_2)_n$—,
(e) $R^3R^5NCO(CH_2)_n$—,
(f) $R^3R^5N(CH_2)_n$—,
(g) $R^4CONR^5(CH_2)_n$—,
(h) $CF_3(CH_2)_n$—,
(i) $CF_2H(CH_2)_n$—,
(j) $R^4CO(CH_2)_n$—, (k) $F(CH_2)_n$—,
(l) $Cl(CH_2)_n$—,
(m) $Br(CH_2)_n$—,
(n) $R^3O(CH_2)_n$—,
(o) $R^3S(CH_2)_n$—,
(p) $R^3SO(CH_2)_n$—,
(q) $R^3SO_2(CH_2)_n$—,
(r) $R^3SO_2NR^5(CH_2)_n$—,
(s) $R^3R^4C(OH)(CH_2)_n$—,
(t) $R^3R^4C(NHR^5)(CH_2)_n$—,
(u) $HO_2C(CH_2)_n$—,
(v) $O_2N(CH_2)_n$—,
(w) $C_2$–$C_6$ alkenyl,
(x) $C_2$–$C_6$ alkynyl,
(y) —$CCl_3$,
(z) $R^3ON=CR^3(CH_2)_n$—,
(aa) $NCNR^5(CH_2)_n$—,
(bb) $R^3ONR^5(CH_2)_n$—, or
(cc) $R^3OC(O)NR^5(CH_2)_n$—;

wherein n is 0, 1, 2, 3, 4 or 5;
wherein p is 1, 2 or 3;
wherein $R^3$ is
(a) H,
(b) $C_1$–$C_5$ alkyl, or
(c) cyclopropyl-;
wherein $R^4$ is
(a) H,
(b) $C_1$–$C_5$ alkyl-,
(c) cyclopropyl-,
(d) $R^3O(CH_2)_p$—, or
(e) $R^3CO_2(CH_2)_p$—;
wherein $R^5$ is
(a) H, or
(b) $C_1$–$C_3$ alkyl;
or a pharmaceutically acceptable salt thereof;
with the following proviso:
at least one of $X^1$ and $X^2$ is F or Cl.

More specifically, the present invention provides a compound of formula I
wherein $R^1$ is —$COR^3$, or —$CSR^3$;
wherein $X^1$ and $X^2$ are independently
(a) H, or
(b) F;
wherein Q is the moiety of formula II or IV;
wherein $R^2$ is
(a) $R^3$,
(b) $R^4CO_2(CH_2)_n$—,
(c) $NC(CH_2)_n$—,
(d) $R^3OCO(CH_2)_n$—,
(e) $R^3R^5NCO(CH_2)_n$—,
(f) $R^3R^5N(CH_2)_n$—,
(g) $R^4CONR^5(CH_2)_n$—,
(h) $CF_3(CH_2)_n$—,
(i) $R^4CO(CH_2)_n$—,
(j) $F(CH_2)_n$—,
(k) $Cl(CH_2)_n$—,
(l) $R^3O(CH_2)_n$—,
(m) $R^3S(CH_2)_n$—,
(n) $R^3SO(CH_2)_n$—,
(o) $R^3SO_2(CH_2)_n$—,
(p) $R^3SO_2NR^5(CH_2)_n$—,
(q) $O_2N(CH_2)_n$—, or
(r) $R^3R^4C(NHR^5)(CH_2)_n$—;
wherein n is 0, 1, or 2;
wherein $R^4$ is
(a) H, (b) C$_1$–C$_3$ alkyl, or (c) cyclopropyl.

Even more specifically, the present invention provides the compound of formula I wherein R$^2$ is (a) R$^3$, (b) NC(CH$_2$)$_n$—, (c) R$^3$NHCO(CH$_2$)$_n$—, (d) R$^4$CO(CH$_2$)$_n$—, (e) F(CH$_2$)$_n$—, (g) Cl(CH$_2$)$_n$—, (h) R$^3$O(CH$_2$)$_n$—, (i) R$^3$S(CH$_2$)$_n$—, (j) R$^3$NH(CH$_2$)$_n$—, or (k) R$^4$CONH(CH$_2$)$_n$—.

Even more specifically, the present invention provides the above compounds wherein Q is the moiety of formula II.

In another aspect, the subject invention is directed toward a method for treating microbial infections in patients by administering to a patient in need thereof an effective amount of a compound of Formula I as described above. The compound may be administered in a pharmaceutical composition either orally, parenterally, transdermally, or topically. Preferably, the compound is administered in an amount of from about 0.1 to about 100 mg/kg of body weight/day, more preferably, from about 3.0 to about 50 mg/kg of body weight/day. Some of the compounds of the present invention, especially the 1,3,4-thiadiazol-2-yl-containing compounds, are also surprisingly effective antibacterial agents against fastidious gram-negative bacteria/organisms. The activity of several compounds of the present invention against a gram-negative bacterial strain is given in Table 2.

The compounds of the present invention are named according to the IUPAC or CAS nomenclature system.

The carbon atoms content of various hydrocarbon-containing moieties is indicated by a prefix designating the minimum and maximum number of carbon atoms in the moiety; i.e., the prefix Ci–Cj indicates a moiety of the integer "I" to the integer "j" carbon atoms, inclusive. Thus, for example, C$_1$–C$_3$ alkyl refers to alkyl of one to three carbon atoms, inclusive, or ethyl, ethyl, propyl, and isopropyl.

Examples of alkyl of one to nine carbon atoms, inclusive, are methyl, ethyl, propyl, butyl, pentyl, hexyl, heptyl, octyl, and nonyl, and all isomeric forms thereof, straight and branched.

Examples of alkenyl of one to five carbon atoms, inclusive, are ethenyl, propenyl, butenyl, pentenyl, and all isomeric forms thereof.

DETAILED DESCRIPTION OF THE INVENTION

The X$^1$ and X$^2$ groups may be independently either hydrogen atoms or the defined halogen atoms in a variety of substitution patterns. The X$^1$ and X$^2$ substituents are preferably one fluorine and one H.

The preferred absolute configuration at C-5 of the oxazolidinone ring of compounds claimed in this invention is as represented in the structure of Formula I. This configuration is called (S) under the Cahn-Ingold-Prelog nomenclature system. It is this (S)-enantiomer which is antibacterially active. The racemic mixture is useful in the same way and for the same purpose as the pure (S)-enantiomer; the difference is that twice as much racemic material must be used to produce the same antibacterial effect. It will be apparent to one skilled in the art that selected azolyl ring systems may have additional chiral centers present to give diastereomers. These diastereomers, in racemic and enantiomerically enriched forms, are also within the scope of the compounds of Formula I.

As is apparent to those of ordinary skill in the art, the compounds of the present invention can exist in several tautomeric forms, and all such tautomeric forms are included within the scope of the present invention. For instance, in the compound of Example 29 below, the 4,5-dihydro-5-oxo-1,3,4-thiadiazol-2-yl group, can exist as the 5-hydroxy-1,3,4-thiadiazol-2-yl group and both such tautomers are included within the scope of the present invention.

Methods for preparing the oxazolidinones of Formula I are depicted in the following pages. It will be apparent to those skilled in the art that the described synthetic procedures are merely representative in nature and that alternative procedures are feasible and may be preferred in some cases.

1,3,4-Thiadiazoles (I-A) of the present invention (formula I wherein Q is moiety II) are made by the reaction of the trimethylstannylphenyl oxazolidinone, X, with 2-chloro-1,3,4-thiadiazoles as shown in Scheme I-A below. Oxazolidinone X is prepared as described in U.S. Pat. No. 5,565,571 (Preparation 19). The required 2-chloro-1,3,4-thiadiazoles are well known in the chemical literature and many methods exist for their preparation.

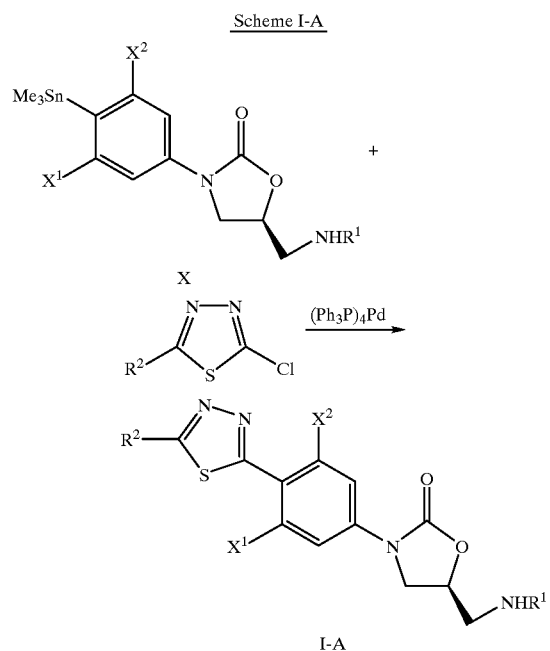

Scheme I-A

Alternatively, oxazolidinones I-A are preferably made by the sequence of steps shown in Scheme 1 below. Diazotization of aniline XI (prepared as described in International Publication No. WO 96/23788, published Aug. 8, 1996, on page 33, lines 13–20) and reaction of the diazonium salt with cuprous cyanide gives the nitrile, XII. This nitrile is converted to the thioamide XIII by reaction with hydrogen sulfide. Methylation of the thioamide is carried out by reaction with methyl triflate to produce the isothioamide XIV. Reaction of XIV with hydrogen sulfide gives the dithiobenzoate ester, XV. Addition of hydrazine to XV produces the thiobenzhydrazide XVI. Reaction of XVI with various carboxylic acids or acid chlorides affords the thiadiazoles I-A.

Scheme 1

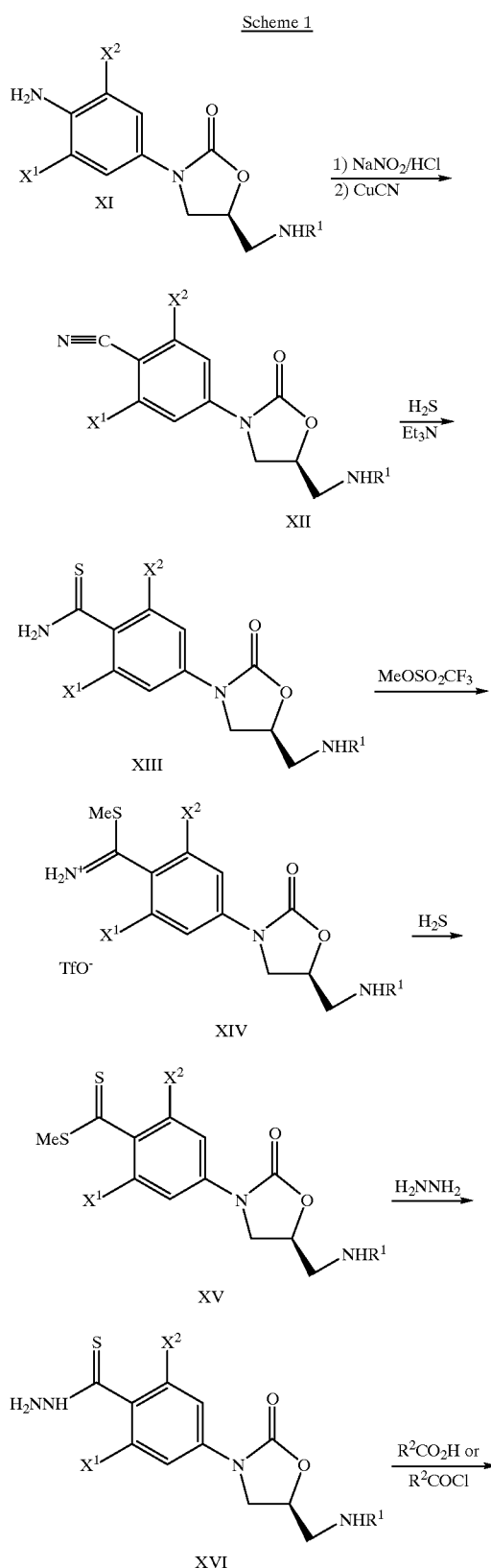

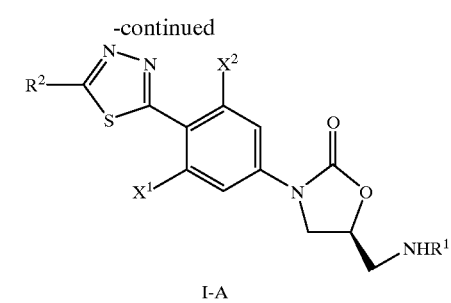

1,2,4-Thiadiazoles (I-B) of the present invention (formula I wherein Q is moiety III) are made by the reaction sequence shown in Scheme 2 below. Hydrolysis of the nitrile XII to the amide XVII is accomplished with potassium hydroperoxide. Reaction of XVII with chlorocarbonylsulfenylchloride produces the oxathiazolone, XVIII. Pyrolysis of XVIII in the presence of various nitriles leads to oxazolidinones I-B.

Scheme 2

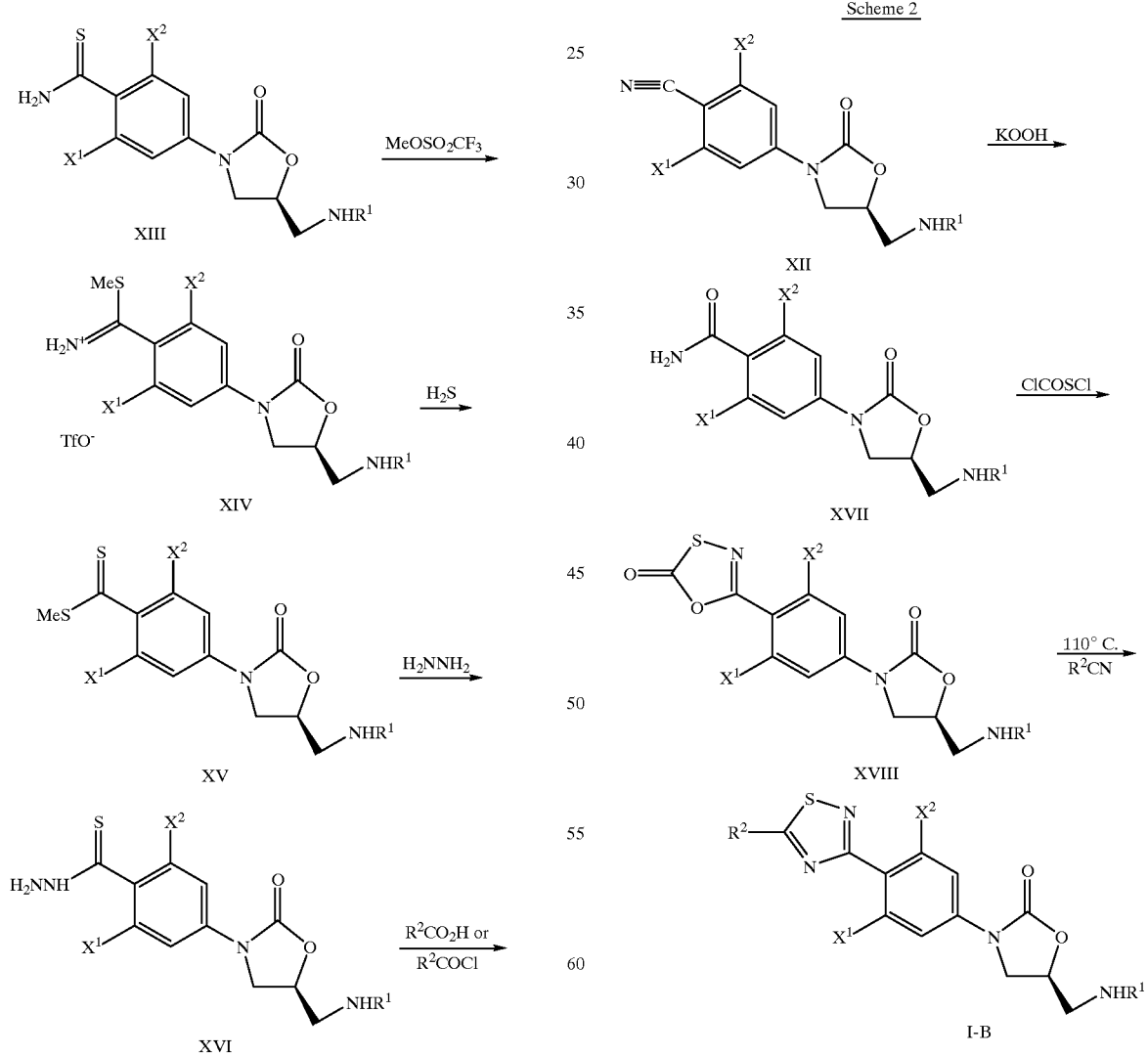

1,2,4-Thiadiazoles (I-C) of the present invention (formula I wherein Q is moiety IV) are made by procedures outlined by Y. Lin (*J. Org. Chem.* 1980, 45, 3750–3753) as shown in Scheme 3 below. Thus, reaction of the thiobenzamide XIII with a dimethoxyalkylamine leads to the amidine, XIX. Treatment of this amidine with hydroxylamine sulfonic acid produces the oxazolidinone I-C.

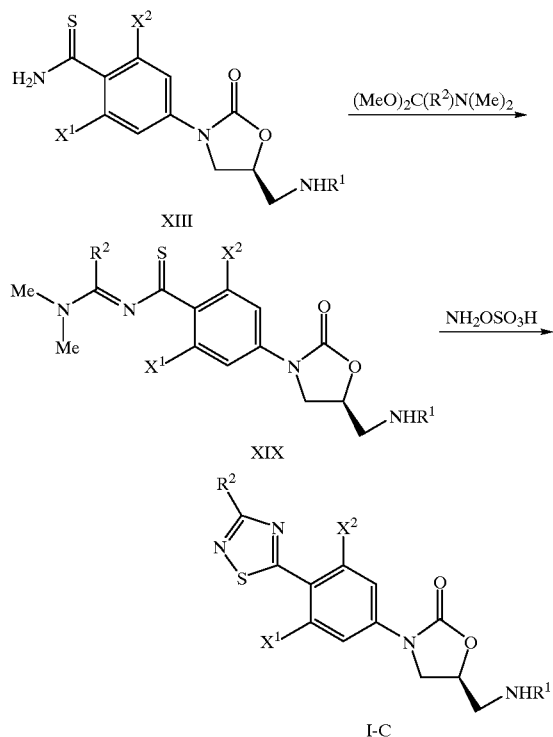

1,2,5-Thiadiazoles (I-D) of the present invention (formula I wherein Q is moiety V) are made by procedures outlined by J. Cho (*J. Chem. Soc. Perkin Trans. I*, 1993, 2345–2350). As shown in Scheme 4 below, reaction of the appropriate aryl ketone XX with hydroxylamine gives the oxime XXI. Treatment of XXI with $S_2N_4$ produces oxazolidinone I-D. The required ketones are prepared by procedures disclosed by C-H. Park (*J. Med. Chem.* 1992, 35, 1156–1165).

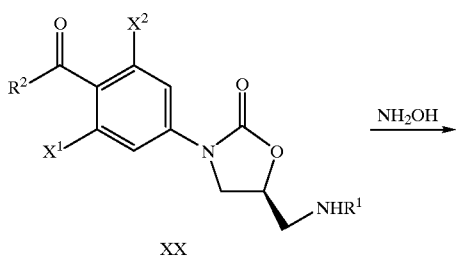

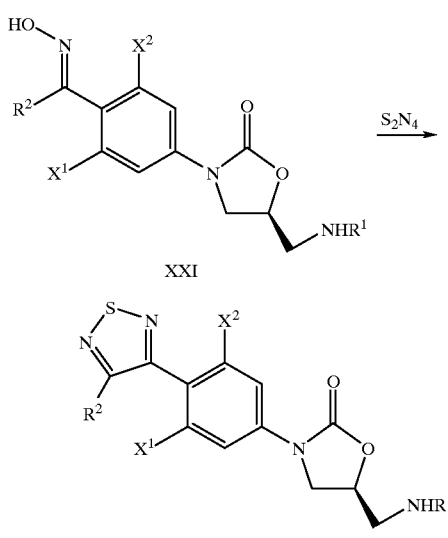

1,2,3-Thiadiazoles (I-E) of the present invention (formula I wherein Q is moiety VI) are made from the appropriate ketone XX by procedures outlined by E. Thomas (*J. Med. Chem.* 1985, 28, 2345–2350) and shown below in Scheme 5.

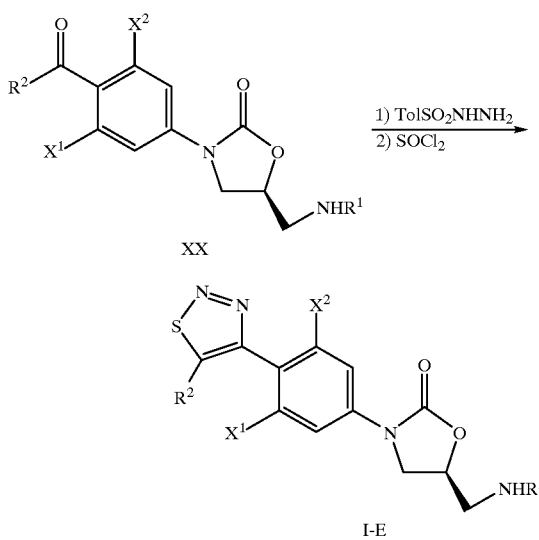

1,2,3-Thiadiazoles (I-F) of the present invention (formula I wherein Q is moiety VII) are made from the dithiobenzoate XIII according to the method of T. Aoyama (*Heterocycles*, 1986, 24, 589–592), as shown in Scheme 6 below.

Scheme 6

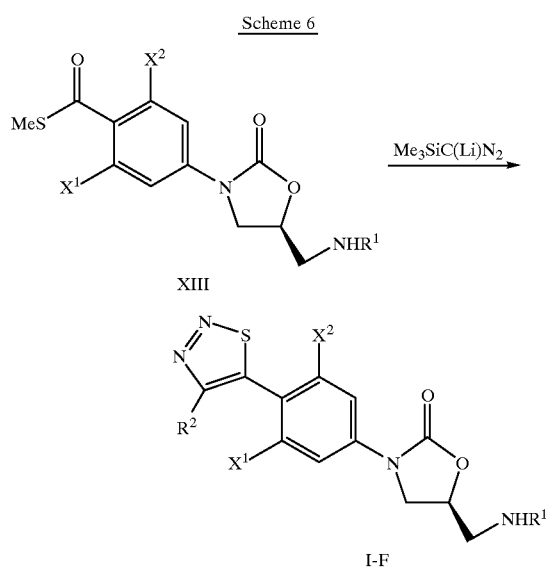

Scheme 8

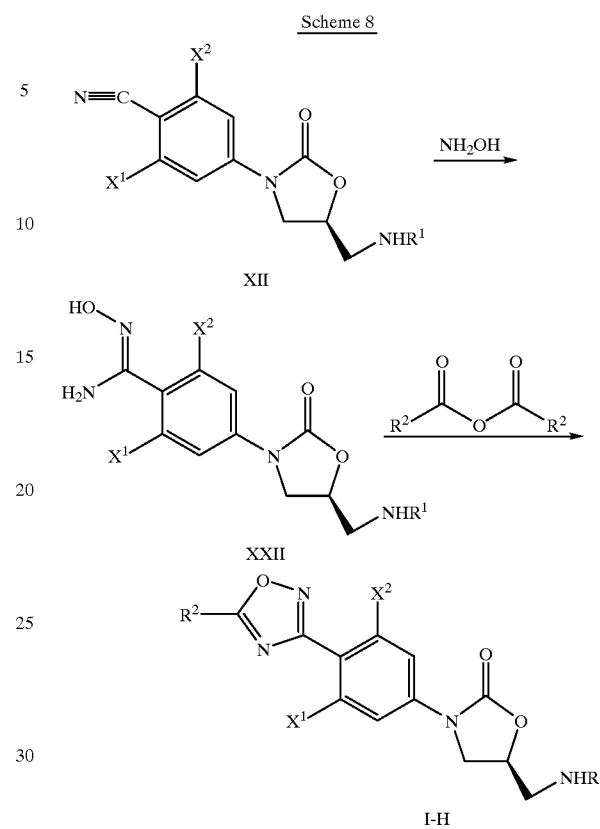

1,3,4-oxadiazoles (I-G) of the present invention (formula I wherein Q is moiety VIII) are made from the nitrile XII using the appropriate acylhydrazide, following the procedures reported by R. L. Harris (*Aust.J.Chem.* 1977, 30, 2225–2240) as shown below in Scheme 7.

Scheme 7

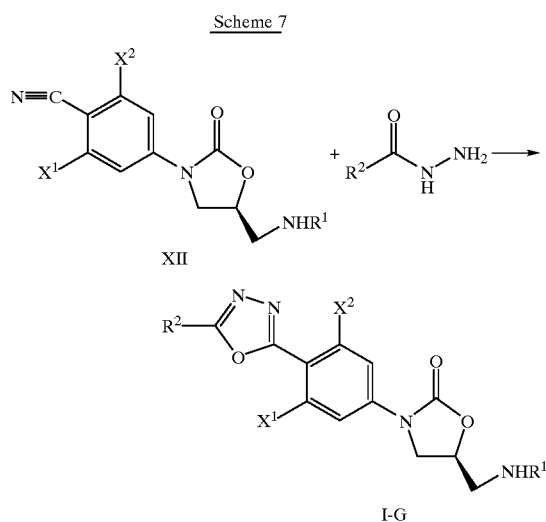

1,2,4-Oxadiazoles (I-H) of the present invention (formula I wherein Q is moiety IX) are made from the nitrile XII by conversion to the hydroxyamidine XXII and then cyclization with the appropriate anhydride, as shown in Scheme 8 below.

The 1,2,4-Oxadiazoles (I-I) of the present invention (formula I wherein Q is moiety IX-A) are made as additional products from the reaction shown in Scheme 3.

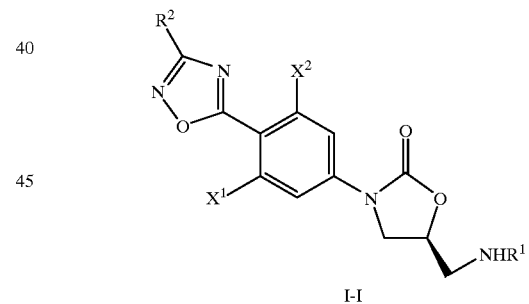

The preparation of oxazolidinones having a thiocarbonyl functionality is disclosed in U.S. patent application, Ser. No. 60/048,342, filed May 30, 1997, which is hereby incorporated by reference herein.

The compounds of Formula I are useful for treatment of microbial infections in humans and other warm blooded animals, under both parenteral, topical, transdermal, and oral administration.

The pharmaceutical compositions of this invention are prepared by combining the compounds of Formula I of this invention with a solid or liquid pharmaceutically acceptable carrier and, optionally, with pharmaceutically acceptable adjuvants and excipients employing standard and conventional techniques. Solid form compoions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound of Formula I according to this invention.

The quantity of active component, that is the compound of Formula I according to this invention, in the pharmaceutical composition and unit dosage form thereof may be varied or adjusted widely depending upon the particular application, the potency of the particular compound and the desired concentration. Generally, the quantity of active component will range between 0.5% to 90% by weight of the composition.

In therapeutic use for treating, or combatting, bacterial infections in warm-blooded animals, the compounds or pharmaceutical compositions thereof will be administered orally, parenterally, transdermally, or topically at a dosage to obtain and maintain a concentration, that is, an amount, or blood-level of active component in the animal undergoing treatment which will be antibacterially effective. The therapeutic uses of these compounds include their use in treating ocular infections and other ophthalmic uses. Generally, such antibacterially effective amount of dosage of active component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of Formula I according to this invention are administered parenterally, i.e., by injection, for example, by intravenous injection or by other parenteral routes of administration. Pharmaceutical compositions for parenteral administration will generally contain a pharmaceutically acceptable amount of the compound according to Formula I as a soluble salt (acid addition salt or base salt) dissolved in a pharmaceutically acceptable liquid carrier such as, for example, water-for-injection and a buffer to provide a suitably buffered isotonic solution, for example, having a pH of about 3–7. Suitable buffering agents include, for example, trisodium orthophosphate, sodium bicarbonate, sodium citrate, N-methylglucamine, L(+)-lysine and L(+)-arginine to name but a few representative buffering agents. The compound according to Formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage. The compounds of Formula I according to this invention, due to their aqueous solubility, are advantageously administered orally in solid and liquid dosage forms.

The oxazolidinone antibacterial agents of this invention have useful activity against a variety of microorganisms. The in vitro activity of compounds of this invention can be assessed by standard testing procedures such as the determination of minimum inhibitory concentration (MIC) by agar dilution as described in "Methods for Dilution Antimicrobial Susceptibility Tests for Bacteria That Grow Aerobically" (MFT) published January 1983 by the National Committee for Clinical Laboratory Standards, 771 East Lancaster Avenue, Villanova, Pa. 19084, USA. The activity of selected compounds of this invention against *Staphylococcus aureus* and *Streptococcus pneumoniae* are shown in Table 1.

The following compounds of the present invention are preferred:

1. (S)-N-[[3-[4-(5-Cyano-1,3,4-thiadiazol-2-yl)-3-fluorophenyl]-2-oxo-5-oxazolidinyl]methyl]acetamide;
2. (S)-5-[4-[5-[(Acetylamino)methyl]-2-oxo-3-oxazolidinyl]-2-fluorophenyl]-1,3,4-thiadiazole-2-carboxamide;
3. (S)-N-[[3-[3-Fluoro-4-(5-methyl-1,3,4-thiadiazol-2-yl)phenyl]-2-oxo-5-oxazolidinyl]methyl]acetamide;
4. (S)-N-[[3-[4-(5-Ethyl-1,3,4-thiadiazol-2-yl)-3-fluorophenyl]-2-oxo-5-oxazolidinyl]methyl]acetamide;
5. (S)-N-[[3-[3-Fluoro-4-(5-propyl-1,3,4-thiadiazol-2-yl)phenyl]-2-oxo-5-oxazolidinyl]methyl]acetamide;
6. (S)-N-[[3-[4-[5-(Aminomethyl)-1,3,4-thiadiazol-2-yl]-3-fluorophenyl]-2-oxo-5-oxazolidinyl]methyl]acetamide;
7. S)-N-[[3-[3-Fluoro-4-[5-[[(methylsulfonyl)amino]methyl]-1,3,4-thiadiazol-2-yl]phenyl]-2-oxo-5-oxazolidinyl]methyl]acetamide;
8. (S)-N-[[3-[3-Fluoro-4-(5-fluoromethyl-1,3,4-thiadiazol-2-yl)phenyl]-2-oxo-5-oxazolidinyl]methyl]acetamide;
9. (S)-N-[[3-[3-Fluoro-4-(1,3,4-thiadiazol-2-yl)phenyl]-2-oxo-5-oxazolidinyl]methyl]acetamide;
10. (S)-N-[[3-[4-(5-Acetoxymethyl-1,3,4-thiadiazol-2-yl)-3-fluorophenyl]-2-oxo-5-oxazolidinyl]methyl]acetamide;
11. (S)-N-[[3-[3-Fluoro-4-(5-hydroxymethyl-1,3,4-thiadiazol-2-yl)phenyl]-2-oxo-5-oxazolidinyl]methyl]acetamide;
12. (S)-N-[[3-[3-Fluoro-4-[5-(methoxymethyl)-1,3,4-thiadiazol-2-yl]phenyl]-2-oxo-5-oxazolidinyl]methyl]acetamide;
13. (S)-N-[[3-[4-[5-(Cyanomethyl)-1,3,4-thiadiazol-2-yl]-3-fluorophenyl]-2-oxo-5-oxazolidinyl]methyl]acetamide;
14. (S)-5-[4-[5-[(Acetylamino)methyl]-2-oxo-3-oxazolidinyl]-2-fluorophenyl]-1,3,4-thiadiazole-2-acetamide;
15. (S)-N-[[3-[3-Fluoro-4-[5-(trifluoromethyl)-1,3,4-thiadiazol-2-yl]phenyl]-2-oxo-5-oxazolidinyl]methyl]acetamide;
16. (S)-N-[[3-[3-Fluoro-4-[5-(3-oxobutyl)-1,3,4-thiadiazol-2-yl]phenyl]-2-oxo-5-oxazolidinyl]methyl]acetamide;
17. (5S)-N-[[3-[3-Fluoro-4-[5-(3-hydroxybutyl)-1,3,4-thiadiazol-2-yl]phenyl]-2-oxo-5-oxazolidinyl]methyl]acetamide;
18. (S)-Methyl 5-[4-[5-[(acetylamino)methyl]-2-oxo-3-oxazolidinyl]-2-fluorophenyl]-1,3,4-thiadiazole-2-propanoate;

19. (S)-5-[4-[5-[(Acetylamino)methyl]-2-oxo-3-oxazolidinyl]-2-fluorophenyl]-1,3,4-thiadiazole-2-propanamide;
20. (S)-N-[[3-[4-[5-(2-Cyanoethyl)-1,3,4-thiadiazol-2-yl]-3-fluorophenyl]-2-oxo-5-oxazolidinyl]methyl]acetamide;
21. (S)-N-[[3-[3-Fluoro-4-[5-[(methylthio)methyl]-1,3,4-thiadiazol-2-yl]phenyl]-2-oxo-5-oxazolidinyl]methyl]acetamide;
22. (S)-N-[[3-[3-Fluoro-4-[5-[(methylsulfinyl)methyl]-1,3,4-thiadiazol-2-yl]phenyl]-2-oxo-5-oxazolidinyl]methyl]acetamide;
23. (S)-N-[[3-[3-Fluoro-4-[5-[2-(methylthio)ethyl]-1,3,4-thiadiazol-2-yl]phenyl]-2-oxo-5-oxazolidinyl]methyl]acetamide;
24. (S)-N-[[3-[3-Fluoro-4-[5-[2-(methylsulfinyl)ethyl]-1,3,4-thiadiazol-2-yl]phenyl]-2-oxo-5-oxazolidinyl]methyl]acetamide;
25. (S)-Ethyl 5-[4-[5-[(acetylamino)methyl]-2-oxo-3-oxazolidinyl]-2-fluorophenyl]-1,3,4-thiadiazole-2-acetate;
26. (S)-N-[[3-[3-Fluoro-4-[5-(2-hydroxyethyl)-1,3,4-thiadiazol-2-yl]phenyl]-2-oxo-5-oxazolidinyl]methyl]acetamide;
27. (S)-Ethyl 5-[4-[5-[(acetylamino)methyl]-2-oxo-3-oxazolidinyl]-2-fluorophenyl]-1,3,4-thiadiazole-2-carboxylate;
28. (5S)-N-[[3-[3-Fluoro-4-[5-(2-hydroxypropyl)-1,3,4-thiadiazol-2-yl]phenyl]-2-oxo-5-oxazolidinyl]methyl]acetamide;
29. (S)-N-[[3-[4-(4,5-Dihydro-5-oxo-1,3,4-thiadiazol-2-yl)-3-fluorophenyl]-2-oxo-5-oxazolidinyl]methyl]acetamide;
30. (S)-N-[[3-[4-(5-Amino-1,3,4-thiadiazol-2-yl)-3-fluorophenyl]-2-oxo-5-oxazolidinyl]methyl]acetamide;
31. (S)-N-[[3-[3-Fluoro-4-[5-(methylthio)-1,3,4-thiadiazol-2-yl]phenyl]-2-oxo-5-oxazolidinyl]methyl]acetamide;
32. (S)-N-[[3-[3-Fluoro-4-(5-methyl-1,3,4-thiadiazol-2-yl)phenyl]-2-oxo-5-oxazolidinyl]methyl]propanamide;
33. (S)-3-[4-[5-[(Acetylamino)methyl]-2-oxo-3-oxazolidinyl]-2-fluorophenyl]-1,2,4-thiadiazole-5-carboxamide;
34. (S)-N-[[3-[3-Fluoro-4-(1,2,4-thiadiazol-5-yl)phenyl]-2-oxo-5-oxazolidinyl]methyl]acetamide;
35. (S)-N-[[3-[3-Fluoro-4-(5-methyl-1,2,4-oxadiazol-3-yl)phenyl]-2-oxo-5-oxazolidinyl]methyl]acetamide;
36. (S)-N-[[3-[3-Fluoro-4-(1,2,4-oxadiazol-3-yl)phenyl]-2-oxo-5-oxazolidinyl]methyl]acetamide;
37. (S)-3-[4-[5-[(Acetylamino)methyl]-2-oxo-3-oxazolidinyl]-2-fluorophenyl]-1,2,4-oxadiazole-5-carboxamide;
38. (S)-N-[[3-[4-(5-Cyano-1,2,4-oxadiazol-3-yl)-3-fluorophenyl]-2-oxo-5-oxazolidinyl]methyl]acetamide;
39. (S)-N-[[3-[3-Fluoro-4-[5-(trifluoromethyl)-1,2,4-oxadiazol-3-yl]phenyl]-2-oxo-5-oxazolidinyl]methyl]acetamide;
40. (S)-N-[[3-[3-Fluoro-4-(1,2,4-oxadiazol-5-yl)phenyl]-2-oxo-5-oxazolidinyl]methyl]acetamide;
41. (S)-N-[[3-[3-Fluoro-4-[5-(formylamino)-1,3,4-thiadiazol-2-yl]phenyl]-2-oxo-5-oxazolidinyl]methyl]acetamide;
42. (S)-N-[[3-[4-[5-(2-Chloroethyl)-1,3,4-thiadiazol-2-yl]-3-fluorophenyl]-2-oxo-5-oxazolidinyl]methyl]acetamide;
43. (S)-N-[[3-[3-Fluoro-4-[5-(1-propenyl)-1,3,4-thiadiazol-2-yl]phenyl]-2-oxo-5-oxazolidinyl]methyl]acetamide;
44. (S)-N-[[3-[4-[5-(2-Aminoethyl)-1,3,4-thiadiazol-2-yl]-3-fluorophenyl]-2-oxo-5-oxazolidinyl]methyl]acetamide;
45. (S)-N-[[3-[4-[5-[2-(Acetylamino)ethyl]-1,3,4-thiadiazol-2-yl]-3-fluorophenyl]-2-oxo-5-oxazolidinyl]methyl]acetamide;
46. (S)-N-[[3-[3-Fluoro-4-[5-[2-[(methylsulfonyl)amino]ethyl]-1,3,4-thiadiazol-2-yl]phenyl]-2-oxo-5-oxazolidinyl]methyl]acetamide;
47. (5S)-N-[[3-[3-Fluoro-4-[5-(methylsulfinyl)-1,3,4-thiadiazol-2-yl]phenyl]-2-oxo-5-oxazolidinyl]methyl]acetamide;
48. (S)-N-[[3-[3-Fluoro-4-[5-(1-methylethyl)-1,3,4-thiadiazol-2-yl]phenyl]-2-oxo-5-oxazolidinyl]methyl]acetamide;
49. (S)-N-[[5-[4-[5-[(Acetylamino)methyl]-2-oxo-3-oxazolidinyl]-2-fluorophenyl]-1,3,4-thiadiazol-2-yl]methyl]acetamide;
50. (S)-N-[[3-[3-Fluoro-4-[5-(3-hydroxypropyl)-1,3,4-thiadiazol-2-yl]phenyl]-2-oxo-5-oxazolidinyl]methyl]acetamide;
51. [S-(R*,R*)]-N-[[3-[3-Fluoro-4-[5-(1-hydroxyethyl)-1,3,4-thiadiazol-2-yl]phenyl]-2-oxo-5-oxazolidinyl]methyl]acetamide;
52. [S-(R*,S*)]-N-[[3-[3-Fluoro-4-[5-(1-hydroxyethyl)-1,3,4-thiadiazol-2-yl]phenyl]-2-oxo-5-oxazolidinyl]methyl]acetamide;
53. (S)-N-[[3-[3-Fluoro-4-[5-(2-nitroethyl)-1,3,4-thiadiazol-2-yl]phenyl]-2-oxo-5-oxazolidinyl]methyl]acetamide;
54. (S)-N-[[3-[3-Fluoro-4-[5-(3-nitropropyl)-1,3,4-thiadiazol-2-yl]phenyl]-2-oxo-5-oxazolidinyl]methyl]acetamide;
55. [S-(R*,R*)]-N-[[3-[4-[5-(1-Aminoethyl)-1,3,4-thiadiazol-2-yl]-3-fluorophenyl]-oxo-5-oxazolidinyl]methyl]acetamide;
56. [S-(R*,S*)]-N-[[3-[4-[5-(1-Aminoethyl)-1,3,4-thiadiazol-2-yl]-3-fluorophenyl]-2-oxo-5-oxazolidinyl]methyl]acetamide;
57. (S)-N-[[3-[4-[5-(3-Aminopropyl)-1,3,4-thiadiazol-2-yl]-3-fluorophenyl]-2-oxo-5-oxazolidinyl]methyl]acetamide;
58. (S)-N-[3-[5-[4-[5-[(Acetylamino)methyl]-2-oxo-3-oxazolidinyl]-2-fluorophenyl]-1,3,4-thiadiazol-2-yl]propyl]acetamide;
59. (S)-N-[[3-[4-(5-Acetyl-1,3,4-thiadiazol-2-yl)-3-fluorophenyl]-2-oxo-5-oxazolidinyl]methyl]acetamide;
60. (S)-N-[[3-[4-[5-(3-Chloropropyl)-1,3,4-thiadiazol-2-yl]-3-fluorophenyl]-2-oxo-5-oxazolidinyl]methyl]acetamide;
61. (S)-N-[[3-[4-[5-(3-Cyanopropyl)-1,3,4-thiadiazol-2-yl]-3-fluorophenyl]-2-oxo-5-oxazolidinyl]methyl]acetamide;
62. (S)-N-[[3-[3-Fluoro-4-[5-(methylsulfonyl)-1,3,4-thiadiazol-2-yl]phenyl]-2-oxo-5-oxazolidinyl]methyl]acetamide;
63. (S)-N-[[3-[3-Fluoro-4-[5-[3-(hydroxyimino)butyl]-1,3,4-thiadiazol-2-yl]phenyl]-2-oxo-5-oxazolidinyl]methyl]acetamide;
64. (S)-N-[[3-[3-Fluoro-4-[5-[2-(hydroxyimino)ethyl]-1,3,4-thiadiazol-2-yl]phenyl]-2-oxo-5-oxazolidinyl]methyl]acetamide;
65. (S)-N-[[3-[3-Fluoro-4-[5-[3-(methoxyimino)butyl]-1,3,4-thiadiazol-2-yl]phenyl]-2-oxo-5-oxazolidinyl]methyl]acetamide;
66. (S)-N-[[5-[4-[5-[(Acetyloxyacetylamino)methyl]-2-oxo-3-oxazolidinyl]-2-fluorophenyl]-1,3,4-thiadiazol-2-yl]methyl]acetamide;
67. (S)-N-[[5-[4-[5-[(Hydroxyacetylamino)methyl]-2-oxo-3-oxazolidinyl]-2-fluorophenyl]-1,3,4-thiadiazol-2-yl]methyl]acetamide;
68. (S)-N-[5-[4-[5-[(Acetylamino)methyl]-2-oxo-3-oxazolidinyl]-2-fluorophenyl]-1,3,4-thiadiazol-2-yl]-2-(acetyloxy)acetamide;
69. (S)-N-[[3-[3-Fluoro-4-[5-[(methylsulfonyl)methyl]-1,3,4-thiadiazol-2-yl]phenyl]-2-oxo-5-oxazolidinyl]methyl]acetamide;

70. (S)-N-[[3-[3-Fluoro-4-[5-[2-(methylsulfonyl)ethyl]-1,3,4-thiadiazol-2-yl]phenyl]-2-oxo-5-oxazolidinyl]methyl]acetamide;
71. (S)-N-[[3-[3-Fluoro-4-(1,3,4-thiadiazol-2-yl)phenyl]-2-oxo-5-oxazolidinyl]methyl]propanamide;
72. (S)-N-[[3-[3-Fluoro-4-[5-(2-methoxyethyl)-1,3,4-thiadiazol-2-yl]phenyl]-2-oxo-5-oxazolidinyl]methyl]propanamide;
73. (S)-N-[[3-[3-Fluoro-4-[5-(2-methoxyethyl)-1,3,4-thiadiazol-2-yl]phenyl]-2-oxo-5-oxazolidinyl]methyl]acetamide;
74. (S)-N-[[3-[3-Fluoro-4-(1,3,4-thiadiazol-2-yl)phenyl]-2-oxo-5-oxazolidinyl]methyl]ethanethioamide;
75. (S)-[[3-[3-Fluoro-4-(1,3,4-thiadiazol-2-yl)phenyl]-2-oxo-5-oxazolidinyl]methyl]thiourea;
76. (S)-N-[[3-[3-Fluoro-4-(1,3,4-thiadiazol-2-yl)phenyl]-2-oxo-5-oxazolidinyl]methyl]propanethioamide;
77. N-[((5S)-3-{4-[5-(aminomethyl)-1,3,4-thiadiazol-2-yl]-3-fluorophenyl}-2-oxo-1,3-oxazolidin-5-yl)methyl]ethanethioamide;
78. 2-({[5-(4-{(5S)-5-[(ethanethioylamino)methyl]-2-oxo-1,3-oxazolidin-3-yl}-2-fluorophenyl)-1,3,4-thiadiazol-2-yl]methyl}amino)-2-oxoethyl acetate; and
79. N-{[5-(4-{(5S)-5-[(ethanethioylamino)methyl]-2-oxo-1,3-oxazolidin-3-yl}-2-fluorophenyl)-1,3,4-thiadiazol-2-yl]methyl}-2-hydroxyacetamide.

The following compounds of the present invention are most preferred:

1. (S)-N-[[3-[4-(5-Cyano-1,3,4-thiadiazol-2-yl)-3-fluorophenyl]-2-oxo-5-oxazolidinyl]methyl]acetamide;
2. (S)-N-[[3-[3-Fluoro-4-(5-methyl-1,3,4-thiadiazol-2-yl)phenyl]-2-oxo-5-oxazolidinyl]methyl]acetamide;
3. (S)-N-[[3-[4-(5-Ethyl-1,3,4-thiadiazol-2-yl)-3-fluorophenyl]-2-oxo-5-oxazolidinyl]methyl]acetamide;
4. (S)-N-[[3-[4-[5-(Aminomethyl)-1,3,4-thiadiazol-2-yl]-3-fluorophenyl]-2-oxo-5-oxazolidinyl]methyl]acetamide;
5. (S)-N-[[3-[3-Fluoro-4-[5-[[(methylsulfonyl)amino]methyl]-1,3,4-thiadiazol-2-yl]phenyl]-2-oxo-5-oxazolidinyl]methyl]acetamide;
6. (S)-N-[[3-[3-Fluoro-4-(5-fluoromethyl-1,3,4-thiadiazol-2-yl)phenyl]-2-oxo-5-oxazolidinyl]methyl]acetamide;
7. (S)-N-[[3-[3-Fluoro-4-(1,3,4-thiadiazol-2-yl)phenyl]-2-oxo-5-oxazolidiryl]methyl]acetamide;
8. (S)-N-[[3-[4-(5-Acetoxymethyl-1,3,4-thiadiazol-2-yl)-3-fluorophenyl]-2-oxo-5-oxazolidinyl]methyl]acetamide;
9. (S)-N-[[3-[3-Fluoro-4-(5-hydroxymethyl-1,3,4-thiadiazol-2-yl)phenyl]-2-oxo-5-oxazolidinyl]methyl]acetamide;
10. (S)-N-[[3-[4-[5-(Cyanomethyl)-1,3,4-thiadiazol-2-yl]-3-fluorophenyl]-2-oxo-5-oxazolidinyl]methyl]acetamide;
11. (S)-5-[4-[5-[(Acetylamino)methyl]-2-oxo-3-oxazolidinyl]-2-fluorophenyl]-1,3,4-thiadiazole-2-acetamide;
12. (S)-N-[[3-[3-Fluoro-4-[5-(3-oxobutyl)-1,3,4-thiadiazol-2-yl]phenyl]-2-oxo-5-oxazolidinyl]methyl]acetamide;
13. (S)-N-[[3-[4-[5-(2-Cyanoethyl)-1,3,4-thiadiazol-2-yl]-3-fluorophenyl]-2-oxo-5-oxazolidinyl]methyl]acetamide;
14. (S)-N-[[3-[3-Fluoro-4-[5-[2-(methylsulfinyl)ethyl]-1,3,4-thiadiazol-2-yl]phenyl]-2-oxo-5-oxazolidinyl]methyl]acetamide;
15. (S)-N-[[3-[3-Fluoro-4-[5-(2-hydroxyethyl)-1,3,4-thiadiazol-2-yl]phenyl]-2-oxo-5-oxazolidinyl]methyl]acetamide;
16. (S)-N-[[3-[4-(4,5-Dihydro-5-oxo-1,3,4-thiadiazol-2-yl)-3-fluorophenyl]-2-oxo-5-oxazolidinyl]methyl]acetamide;
17. (S)-N-[[3-[3-Fluoro-4-[5-(methylthio)-1,3,4-thiadiazol-2-yl]phenyl]-2-oxo-5-oxazolidinyl]methyl]acetamide;
18. (S)-N-[[3-[3-Fluoro-4-(5-methyl-1,3,4-thiadiazol-2-yl)phenyl]-2-oxo-5-oxazolidinyl]methyl]propanamide;
19. (5S)-N-[[3-[3-Fluoro-4-[5-(methylsulfinyl)-1,3,4-thiadiazol-2-yl]phenyl]-2-oxo-5-oxazolidinyl]methyl]acetamide;
20. (S)-N-[[3-[3-Fluoro-4-[5-(3-hydroxypropyl)-1,3,4-thiadiazol-2-yl]phenyl]-2-oxo-5-oxazolidinyl]methyl]acetamide;
21. [S-(R*,R*)]-N-[[3-[3-Fluoro-4-[5-(1-hydroxyethyl)-1,3,4-thiadiazol-2-yl]phenyl]-2-oxo-5-oxazolidinyl]methyl]acetamide
22. [S-(R*,S*)]-N-[[3-[3-Fluoro-4-[5-(1-hydroxyethyl)-1,3,4-thiadiazol-2-yl]phenyl]-2-oxo-5-oxazolidinyl]methyl]acetamide;
23. (S)-N-[[3-[3-Fluoro-4-[5-(2-nitroethyl)-1,3,4-thiadiazol-2-yl]phenyl]-2-oxo-5-oxazolidinyl]methyl]acetamide;
24. (S)-N-[[3-[3-Fluoro-4-[5-(3-nitropropyl)-1,3,4-thiadiazol-2-yl]phenyl]-2-oxo-5-oxazolidinyl]methyl]acetamide;
25. [S-(R*,R*)]-N-[[3-[4-[5-(1-Aminoethyl)-1,3,4-thiadiazol-2-yl]-3-fluorophenyl]-2-oxo-5-oxazolidinyl]methyl]acetamide;
26. [S-(R*,S*)]-N-[[3-[4-[5-(1-Aminoethyl)-1,3,4-thiadiazol-2-yl]-3-fluorophenyl]-2-oxo-5-oxazolidinyl]methyl]acetamide;
27. (S)-N-[[3-[4-[5-(3-Cyanopropyl)-1,3,4-thiadiazol-2-yl]-3-fluorophenyl]-2oxo-5-oxazolidinyl]methyl]acetamide;
28. (S)-N-[[3-[3-Fluoro-4-[5-[3-(hydroxyimino)butyl]-1,3,4-thiadiazol-2-yl]phenyl]-2-oxo-5-oxazolidinyl]methyl]acetamide;
29. (S)-N-[[3-[3-Fluoro-4-[5-[2-(hydroxyimino)ethyl]-1,3,4-thiadiazol-2-yl]phenyl]-2-oxo-5-oxazolidinyl]methyl]acetamide;
30. (S)-N-[[3-[3-Fluoro-4-[5-[2-(methylsulfonyl)ethyl]-1,3,4-thiadiazol-2-yl]phenyl]-2-oxo-5-oxazolidinyl]methyl]acetamide;
31. (S)-N-[[3-[3-Fluoro-4-(1,3,4-thiadiazol-2-yl)phenyl]-2-oxo-5-oxazolidinyl]methyl]propanamide;
32. (S)-N-[[3-[3-Fluoro-4-(1,3,4-thiadiazol-2-yl)phenyl]-2-oxo-5-oxazolidinyl]methyl]ethanethioamide;
33. (S)-[[3-[3-Fluoro-4-(1,3,4-thiadiazol-2-yl)phenyl]-2-oxo-5-oxazolidinyl]methyl]thiourea;
34. (S)-N-[[3-[3-Fluoro-4-(1,3,4-thiadiazol-2-yl)phenyl]-2-oxo-5-oxazolidinyl]methyl]propanethioamide;
35. N-[((5S)-3-{4-[5-(aminomethyl)-1,3,4-thiadiazol-2-yl]-3-fluorophenyl}-2-ox 1,3-oxazolidin-5-yl)methyl]ethanethioamide;
36. 2-({[5-(4-{(5S)-5-[(ethanethioylamino)methyl]-2-oxo-1,3-oxazolidin-3-yl}-2-fluorophenyl)-1,3,4-thiadiazol-2-yl]methyl}amino)-2-oxoethyl acetate; or
37. N-{[5-(4-{(5S)-5-[(ethanethioylamino)methyl]-2-oxo-1,3-oxazolidin-3-yl}-2-fluorophenyl)-1,3,4-thiadiazol-2-yl]methyl}-2-hydroxyacetamide.

TABLE 1

In Vitro Activity of Examples Against Selected Gram-Positive Bacteria

| | MIC ($\mu$g/mL) | |
| --- | --- | --- |
| Example No. | S. Aureus UC ® 9213 | S. pneumoniae UC ® 9912 |
| 1 | 0.5 | <0.125 |
| 2 | 0.5 | 0.25 |
| 3 | 1 | <0.125 |
| 4 | 1 | 0.25 |
| 5 | 1 | 0.25 |
| 6 | 8 | <0.125 |
| 7 | 4 | <0.125 |
| 8 | 1 | 0.25 |

TABLE 1-continued

In Vitro Activity of Examples Against Selected Gram-Positive Bacteria

| | MIC (μg/mL) | |
|---|---|---|
| Example No. | S. Aureus UC ® 9213 | S. pneumoniae UC ® 9912 |
| 9 | 1 | 0.25 |
| 10 | 1 | <0.125 |
| 11 | 1 | <0.125 |
| 12 | 2 | 0.25 |
| 13 | 2 | 0.25 |
| 14 | 4 | <0.125 |
| 15 | 2 | 0.5 |
| 16 | 1 | <0.125 |
| 17 | 2 | 0.25 |
| 18 | 2 | 0.25 |
| 19 | 8 | <0.125 |
| 20 | 0.5 | <0.125 |
| 21 | 1 | 0.25 |
| 22 | 8 | 0.25 |
| 23 | 1 | 0.25 |
| 24 | 4 | 0.25 |
| 25 | 2 | 0.25 |
| 26 | 2 | <0.125 |
| 27 | 8 | <0.125 |
| 28 | 2 | 0.25 |
| 29 | 1 | 0.25 |
| 30 | 4 | 0.25 |
| 31 | 0.5 | <0.125 |
| 32 | 1 | <0.125 |
| 33 | 16 | 2 |
| 34 | 1 | 0.25 |
| 35 | 16 | 4 |
| 36 | 4 | 1 |
| 37 | >16 | 1 |
| 38 | >16 | 2 |
| 39 | 16 | 8 |
| 40 | 2 | 0.5 |
| 41 | 4 | 0.5 |
| 42 | 1 | <0.125 |
| 43 | 2 | 0.5 |
| 44 | >16 | 0.25 |
| 45 | 16 | 0.5 |
| 46 | 16 | 0.5 |
| 47 | 2 | 0.25 |
| 48 | 1 | 0.25 |
| 49 | 16 | 0.25 |
| 50 | 2 | 0.25 |
| 51 | 2 | 0.25 |
| 52 | 2 | 0.25 |
| 53 | 1 | 0.25 |
| 54 | 2 | 0.25 |
| 55 | 8 | <0.125 |
| 56 | 4 | <0.125 |
| 57 | 16 | 0.5 |
| 58 | 8 | 0.25 |
| 59 | 2 | 0.5 |
| 60 | 2 | 0.5 |
| 61 | 1 | <0.125 |
| 62 | 2 | 0.5 |
| 63 | 2 | <0.125 |
| 64 | 1 | <0.125 |
| 65 | 8 | 2 |
| 66 | 16 | <0.5 |
| 67 | 16 | <0.5 |
| 68 | 8 | 2 |
| 69 | 4 | <0.5 |
| 70 | 4 | <0.5 |
| 71 | 1 | 0.25 |
| 72 | 4 | 0.25 |
| 73 | 2 | <0.5 |
| 74 | 0.25 | <0.125 |
| 75 | 0.25 | <0.125 |
| 76 | 0.25 | <0.125 |
| 77 | <0.5 | <0.5 |
| 78 | 2 | <0.5 |

TABLE 2

MIC Data for a Gram Negative Bacterial Strain

| Example No. | MIC (μg/mL) for HI 30063 |
|---|---|
| 1 | 2 |
| 3 | 2 |
| 4 | 4 |
| 6 | 2 |
| 7 | 2 |
| 8 | 4 |
| 9 | 4 |
| 10 | 4 |
| 11 | 4 |
| 13 | 4 |
| 14 | 4 |
| 16 | 4 |
| 20 | 2 |
| 24 | 4 |
| 26 | 2 |
| 29 | 4 |
| 31 | 4 |
| 32 | 4 |
| 47 | 4 |
| 50 | 4 |
| 51 | 4 |
| 52 | 4 |
| 53 | 4 |
| 54 | 4 |
| 55 | 4 |
| 56 | 4 |
| 61 | 4 |
| 63 | 4 |
| 64 | 2 |
| 70 | 4 |
| 71 | 4 |
| 74 | 1 |
| 75 | 1 |
| 76 | 1 |
| 77 | <0.5 |
| 78 | 4 |

DESCRIPTION OF THE PREFERRED EMBODIMENTS

EXAMPLE 1

(S)-N-[[3-[4-(5-Cyano-1,3,4-thiadiazol-2-yl)-3-fluorophenyl]-2-oxo-5-oxazolidinyl]methyl] acetamide (I-A, $X^1$=F, $X^2$=H, $R^1$=$CH_3CO$, $R^2$=CN). Refer to Scheme 1-A

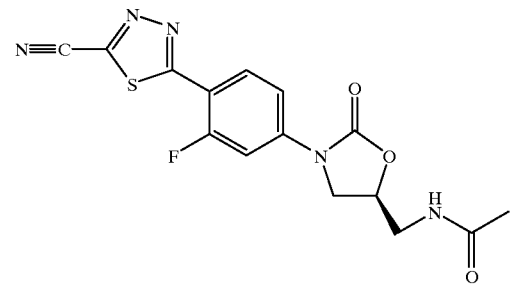

A mixture of the oxazolidinone X, prepared as described in U.S. Pat. No. 5,565,571 (Preparation 19) (208.1 mg), 2-chloro-5-cyano-1,3,4-thiadiazole (72.9 mg), tris(dibenzylideneacetone)dipalladium(0) (9.1 mg) and triphenylarsine (12.2 mg) in 1-methyl-2-pyrrolidinone (3 mL) is evacuated and flushed with $N_2$ three times. The dark reaction mixture is stirred under $N_2$ for 6 days. The reaction mixture is partitioned between water (20 mL) and ethyl acetate (30 mL) and the phases are separated. The aqueous phase is extracted with ethyl acetate (2×25 mL). The combined organics are washed with water (20 mL), brine (20 mL), dried ($MgSO_4$), filtered and concentrated. The dark residue is purified by flash chromatography using 5% methanol in ethyl acetate as the eluent to afford 25.2 mg of the desired thiadiazole.

Physical characteristics are as follows: mp 210–211° C. $^1$H NMR (DMSO) δ 8.39, 8.24, 7.78, 7.60, 4.78, 4.19, 3.81, 3.43, 1.81; Anal. Found: C, 48.67; H, 3.57; N, 18.86; S, 8.33.

EXAMPLE 2

(S)-5-[4-[5-[(Acetylamino)methyl]-2-oxo-3-oxazolidinyl]-2-fluorophenyl]-1,3,4-thiadiazole-2-carboxamide (I-A, $X^1$=F, $X^2$=H, $R^1$=$CH_3$CO, $R^2$=$H_2$NCO). Refer to Scheme 1

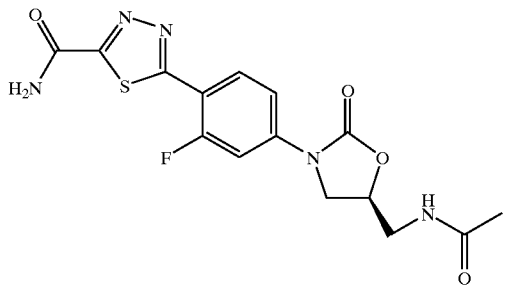

A solution of the title compound of Example 1 (58.6 mg) in 10:1 $H_2SO_4/H_2O$ (1 mL) is heated at 40° C. for 3.5 h. The cooled reaction mixture is treated with ice (15 mL) and the mixture is adjusted to pH 7 with 50 % NaOH, resulting in formation of a solid precipitate. The reaction mixture is concentrated. The resulting solid is dissolved in methanol/chloroform, absorbed onto silica gel, and purified on 20 g of silica gel using 8% methanol in dichloromethane as the eluent to afford 37.1 mg of the title product as a tan solid.

Physical characteristics are as follows: mp 243–244° C. (dec). $^1$H NMR (DMSO) δ 8.62, 8.32, 8.25, 8.18, 7.76, 7.59, 4.76, 4.18, 3.80, 3.42, 1.81.

EXAMPLE 3

(S)-N-[[3-[3-Fluoro-4-(5-methyl-1,3,4-thiadiazol-2-yl)phenyl]-2-oxo-5-oxazolidinyl]methyl]acetamide (I-A, $X^1$=F, $X^2$=H, $R^1$=$CH_3$CO, $R^2$=$CH_3$). Refer to Scheme 1

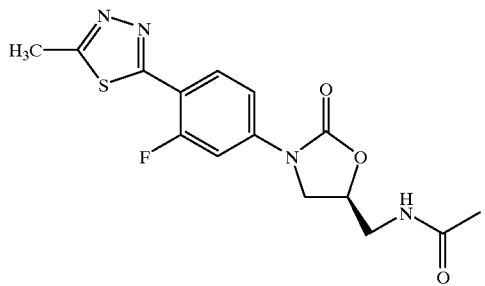

Step 1. The aniline XI, prepared as described in International Publication No. WO 96/23788, published Aug. 8, 1996 (5.2 g) is dissolved in 2 N HCl (23 mL) and cooled to 0° C. Sodium nitrite (2.0 g) in water (12 mL) is added and the resulting yellow solution is stirred at 0° C. for 30 min. Solid sodium bicarbonate is carefully added until the solution reaches pH 7. In a separate flask, copper (I) cyanide (2.3 g) and potassium cyanide (1.9 g) are suspended in water (19 mL) and ethyl acetate (38 mL) at 0° C. The neutralized diazonium salt is added to this solution via cannula over 35 min. The resulting mixture is stirred at 0° C. for 30 min (during which time the mixture becomes very dark in color) then at room temperature for 1 h. The dark heterogeneous reaction mixture is filtered through a pad of celite to remove copper salts. The filter cake is washed with ethyl acetate (2×50 mL) and water (1×50 mL). The phases of the filtrate are separated. The aqueous layer is extracted with ethyl acetate (100 mL). The combined organics are dried ($MgSO_4$), filtered and concentrated. The orange residue is dissolved in 30% acetone in dichloromethane and filtered through a short column of silica gel using 30% acetone in dichloromethane as the eluent. The filtrate is concentrated to afford 3.4 g of desired nitrile XII as a yellow solid.

Physical characteristics are as follows: mp 173–174° C. $^1$H NMR (DMSO) δ 8.22, 7.92, 7.74, 7.52, 4.76, 4.14, 3.76, 3.40, 1.80; Anal. Found: C, 56.16; H, 4.34; N, 14.83.

Step 2. To a stirred solution of the nitrile XII (prepared in Step 1, 3.06 g) in 30 mL of DMF is added triethylamine (3.8 mL) at room temperature. The reaction is heated to 100° C. and $H_2S$ is bubbled into the flask for 1 h. The reaction is then cooled to 60° C. over 30 min. A portion of the DMF (15 mL) is removed via bulb to bulb distillation. The reaction mixture is then poured onto 100 mL of ice and stirred until the ice melts. The mixture is filtered and the orange solid is dried overnight in a vacuum oven to afford 2.9 g of the thioamide XIII. An analytical sample of the thioamide is prepared by chromatography through a Biotage 40S column (1% MeOH in $CH_2Cl_2$).

Physical characteristics are as follows: mp 116–119° C.; $^1$H NMR (DMSO) δ 10.1, 9.4, 8.23, 7.12, 7.46, 7.29, 4.7, 4.12, 3.73, 3.4045, 1.81. Anal. Found: C, 50.54; H, 4.70; N, 13.04; S, 9.60.

Step 3. To a stirred solution of the thioamide XIII (prepared in step 2, 1.05 g) in 1:1 THF/$CH_2Cl_2$ (37 mL) under $N_2$ is added methyl triflate (0.49 mL). The resulting orange solution is stirred at room temperature for 1 h, then pyridine (0.82 mL) is added. Hydrogen sulfide is bubbled through the reaction mixture for 1 h. The hydrogen sulfide is replaced with $N_2$ and nitrogen is bubbled through the reaction mixture for 30 min. The orange solution is concentrated. The resulting orange residue is dissolved in MeOH/$CH_2Cl_2$, absorbed onto silica, and purified using a Biotage 40 M column with a SIM using 2.5% MeOH in $CH_2Cl_2$ as the eluent to afford 640.2 mg of the methyl dithiobenzoate XV as an orange foam which is used immediately in the next reaction without further purification.

Physical characteristics are as follows: $^1$H NMR ($CDCl_3$) 7.68, 7.47, 7.13, 6.81, 4.80, 4.04, 3.79, 3.64, 2.73, 2.00.

Step 4. To a stirred solution of the dithiobenzoate XV (prepared in step 3, 640.2 mg) in ethanol (18 mL) is added hydrazine monohydrate (0.33 mL). (The orange color of the dithiobenzoate dissipates within 5 min after addition of hydrazine). The reaction mixture is stirred at room temperature for 25 min, then concentrated. The yellow residue is dissolved in methanol/$CH_2Cl_2$, absorbed onto silica, and purified on a Biotage 40S column using a SIM and 7% methanol in dichloromethane as the eluent to afford 369.0 mg (60%) of the desired thiohydrazide XVI.

Physical characteristics are as follows: mp 207–208° C. (bubbles). $^1$H NMR (DMSO) δ 12.4, 8.23, 7.54, 7.48, 7.29, 6.25, 4.73, 4.11, 3.72, 3.40, 1.81.

Step 5. To a stirred suspension of the thiohydrazide XVI (prepared as described in step 4, 200.0 mg) in dry THF (4 mL) is added acetyl chloride (52 μL). The reaction mixture is heated at reflux for 30 min, cooled and concentrated. The yellow solid is dissolved in MeOH/CH$_2$Cl$_2$, absorbed onto silica, and purified by flash chromatography using 7% methanol in dichloromethane as the eluent to afford 156.7 mg of the desired thiadiazole 1-A as an off-white solid.

Physical characteristics are as follows: mp 240–242° C. $^1$H NMR (DMSO) δ 8.22, 7.72, 7.53, 4.76, 4.16, 3.78, 3.42, 2.77, 1.81; Anal. Found: C, 51.30; H, 4.17; N, 15.97.

EXAMPLE 4

(S)-N-[[3-[4-(5-Ethyl-1,3,4-thiadiazol-2-yl)-3-fluorophenyl]-2-oxo-5-oxazolidinyl]methyl] acetamide. (I-A, X$^1$=F, X$^2$=H, R$^1$=CH$_3$CO, R$^2$= CH$_3$CH$_2$). Refer to Scheme 1

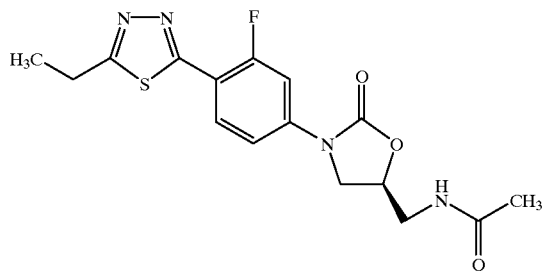

The thiohydrazide XVI from Step 4 of Example 3 (200 mg) is reacted with propionyl chloride (107 μL) according to the procedure of Step 5 of Example 3 to afford 261 mg of the title compound.

Physical characteristics are as follows: mp 221–223° C. $^1$H-NMR (DMSO) δ 8.23, 7.70, 7.53, 4.76, 4.17, 3.80, 3.42, 3.15, 1.82, 1.35. Anal. Found: C, 52.69; H, 4.59; N, 15.39.

EXAMPLE 5

(S)-N-[[3-[3-Fluoro-4-(5-propyl-1,3,4-thiadiazol-2-yl)phenyl]-2-oxo-5-oxazolidinyl]methyl]acetamide. (I-A, X$^1$=H, X$^2$=F, R$^1$=CH$_3$CO, R$^2$=CH$_3$CH$_2$CH$_2$). Refer to Scheme 1

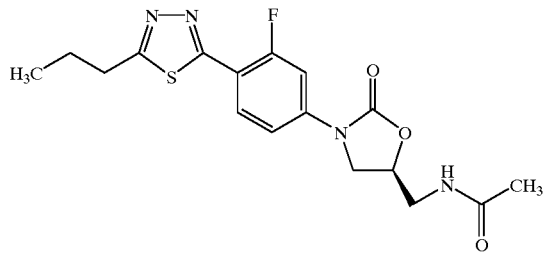

The thiohydrazide XVI from Step 4 of Example 3 (300 mg) is reacted with butyryl chloride (190 μL) according to the procedure of Step 5 of Example 3 to afford 205 mg of the title compound.

Physical characteristics are as follows: mp 210–212° C. $^1$H-NMR (DMSO) δ 8.24, 7.70, 7.53, 4.76, 4.17, 3.80, 3.42, 3.09, 1.82, 1.79, 0.96. Anal. Found: C, 53.57; H, 5.02; N, 14.69.

EXAMPLE 6

(S)-N-[[3-[4-[5-(Aminomethyl)-1,3,4-thiadiazol-2-yl]-3-fluorophenyl]-2-5-oxazolidinyl]methyl] acetamide. (I-A, X$^1$=H, X$^2$=F, R$^1$=CH$_3$CO, R$^2$= NH$_2$CH$_2$). Refer to Scheme 1

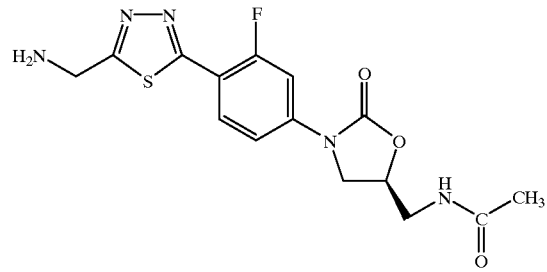

Step 1. The thiohydrazide XVI from Step 4 of Example 3 (532 mg) is reacted with FMOC glycyl chloride (669 mg) according to the procedure of Step 5 of Example 3 to afford 631 mg of the FMOC protected form of the title compound.

Step 2. The product from step 1 is stirred in 5 mL of piperidine at room temperature for 1 h. The desired product is collected by filtration. The mother liquor is absorbed onto silica gel and chromatographed using 2% MeOH (saturated with NH$_3$) in CH$_2$Cl$_2$ as eluent to afford 178 mg of the title compound.

Physical characteristics are as follows: mp 216–217° C. $^1$H-NMR (DMSO) δ 8.22, 7.70. 7.52, 4.76, 4.17, 4.13, 3.80, 3.42, 1.82. % H$_2$O: 3.65. Anal. Found: C, 46.09; H, 4.45; N, 17.01.

EXAMPLE 7

(S)-N-[[3-[3-Fluoro-4-[5-[[(methylsulfonyl)amino] methyl]-1,3,4-thiadiazol-2-yl]phenyl]-2-oxo-5-oxazolidinyl]methyl]acetamide. (I-A, X$^1$=H, X$^2$=F, R$^1$=CH$_3$CO, R$^2$=CH$_3$SO$_2$NHCH$_2$). Refer to Scheme 1

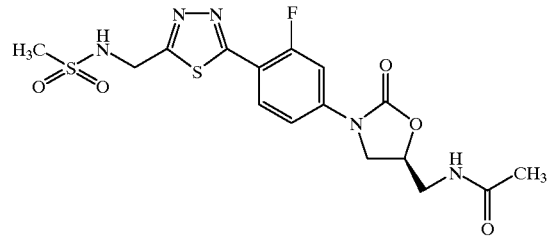

To a suspension of the amine prepared in Example 6 (300 mg) in CH$_2$Cl$_2$ (10 mL) is added triethylamine (459 μL) and methanesulfonyl chloride (127 μL). The reaction is heated to 100° C. for 2 h. The reaction mixture is then cooled to room temperature and concentrated. The residue is absorbed onto silica gel and chromatographed using 10% MeOH/CH$_2$Cl$_2$ as eluent to afford 161 mg of the title compound.

Physical characteristics are as follows: mp 160° C. $^1$H-NMR (DMSO) δ 8.22, 7.70, 7.52, 4.77, 4.17, 4.13, 3.81, 3.42, 3.29, 1.82. % H$_2$O: 3.08. Anal. Found: C, 46.12; H, 4.47; N, 17.06.

EXAMPLE 8

(S)-N-[[3-[3-Fluoro-4-(5-fluoromethyl-1,3,4-thiadiazol-2-yl)phenyl]-2-oxo-5-oxazolidinyl]methyl]acetamide (I-A, $X^1$=H, $X^2$=F, $R^1$=CH$_3$CO, $R^2$=FCH$_2$). Refer to Scheme 1

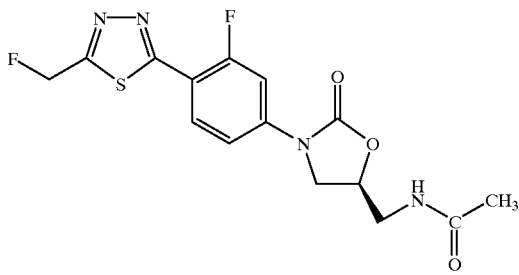

Prepared from the thiohydrazide XVI according to the procedure of Step 5 of Example 3, substituting fluoroacetyl chloride for acetyl chloride. Purified by flash chromatography using 5% methanol in dichloromethane to give 107.0 mg of the desired fluoromethyl thiadiazole as a white solid.

Physical characteristics are as follows: mp 222–223° C. $^1$H NMR (DMSO) δ 8.30, 8.27, 7.76, 7.57, 6.01, 5.85, 4.77, 4.18, 3.80, 3.42, 1.81; Anal. Found: C, 48.64; H, 3.90; N, 15.09.

EXAMPLE 9

(S)-N-[[3-[3-Fluoro-4-(1,3,4-thiadiazol-2-yl)phenyl]-2-oxo-5-oxazolidinyl]-methyl]acetamide. (I-A, $X^1$=H, $X^2$=F, $R^1$=CH$_3$CO, $R^2$=H). Refer to Scheme 1

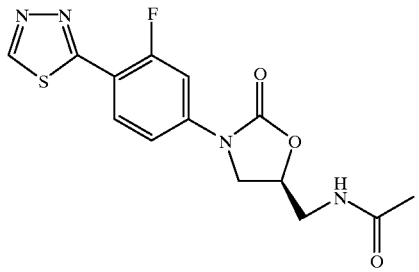

A mixture of thiohydrazide XVI from Step 4 of Example 3 (195 mg) and formic acid (2 mL) is heated at reflux for 45 min. The cooled reaction mixture is concentrated. The resulting residue is dissolved in methanol, absorbed onto silica gel and purified by flash chromatography using 5% MeOH in CH$_2$Cl$_2$ to afford 134 mg of the title compound.

Physical characteristics are as follows: mp 234–235° C. $^1$H-NMR (DMSO) δ 9.75, 8.27, 7.75, 7.55, 4.77, 4.17, 3.79, 3.42, 1.81. Anal. Found: C, 49.87; H, 3.79; N, 16.64; S, 9.43.

EXAMPLE 10

(S)-N-[[3-[4-(5-Acetoxymethyl-1,3,4-thiadiazol-2-yl)-3-fluorophenyl]-2-oxo-5-oxazolidinyl]methyl]acetamide (I-A, $X^1$=H, $X^2$=F, $R^1$=CH$_3$CO, $R^2$=CH$_3$CO$_2$CH$_2$). Refer to Scheme 1

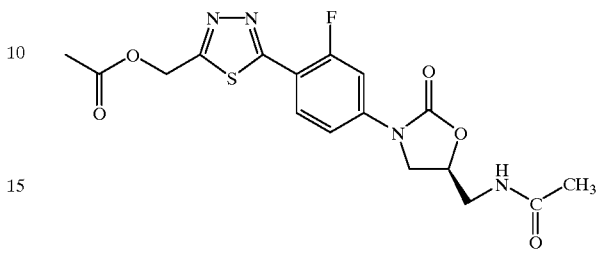

Prepared from the thiohydrazide XVI according to the procedure of Step 5 of Example 3, substituting acetoxyacetyl chloride for acetyl chloride. Purified by flash chromatography using 5% methanol in dichloromethane as the eluent to afford 374.1 mg of the title thiadiazole as an off-white solid.

Physical characteristics are as follows: mp 181–182° C. $^1$H NMR (DMSO) δ 8.27, 7.75, 7.55, 5.53, 4.76, 4.17, 3.76, 3.42, 2.11, 1.81.

EXAMPLE 11

(S)-N-[[3-[3-Fluoro-4-(5-hydroxymethyl-1,3,4-tfhiadiazol-2-yl)phenyl]-2-oxo-5-oxazolidinyl]methyl]acetamide (I-A, $X^1$=H, $X^2$=F, $R^1$=CH$_3$CO, $R^2$=HOCH$_2$). Refer to Scheme 1

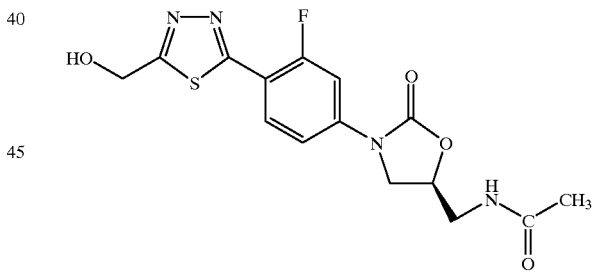

Potassium carbonate (60.6 mg) is added to a stirred suspension of the title compound of Example 10 (128.0 mg) in methanol (3 mL). The heterogeneous reaction mixture is stirred at room temperature for 15 min. Dichloromethane (3 mL) is added and the homogenous reaction mixture is filtered through a plug of cotton to remove the solids. The filtrate is absorbed onto silica gel and purified by flash chromatography using 10% methanol in dichloromethane as the eluent to afford 93.6 mg of the desired hydroxymethyl thiadiazole as a white solid.

Physical characteristics as follows: mp 212–214° C. $^1$H NMR (DMSO) δ 8.24, 7.73, 7.54, 6.25, 4.90, 4.77, 4.17, 3.81, 3.42, 1.81; Anal. Found: C, 49.00; H, 4.20; N, 15.23; S, 8.55.

EXAMPLE 12

(S)-N-[[3-[3-Fluoro-4-[5-(methoxymethyl)-1,3,4-thiadiazol -2-yl]phenyl]-2-oxo-5-oxazolidinyl] methyl]acetamide. (I-A, X¹=F, X²=H, R¹=CH₃CO, R²=CH₃OCH₂). Refer to Scheme 1

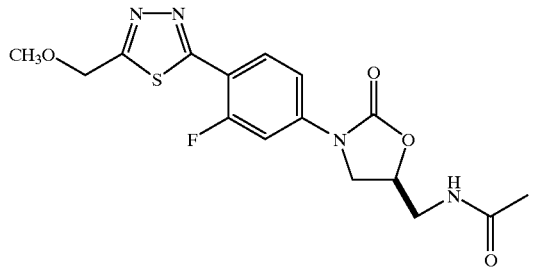

The thiohydrazide XVI from Step 4 of Example 3 (343 mg) is reacted with methoxyacetyl chloride (228 mg) according to the procedure of Step 5, Example 3 to afford 339 mg of the title compound.

Physical characteristics are as follows: mp 198–199° C. ¹H-NMR (DMSO) δ 8.26, 7.73, 7.55, 4.90, 4.77, 4.17, 3.79, 3.42, 3.40, 1.81. % Water (KF) =0.13. Anal. Found: C, 49.40; H, 4.44; N, 14.39; S, 8.24.

EXAMPLE 13

(S)-N-[[3-[4-[5-(Cyanomethyl)-1,3,4-thiadiazol-2-yl]-3-fluorophenyl]-2-oxo-5-oxazolidinyl]methyl] acetamide. (I-A, X¹=F, X²=H, R¹=CH₃CO, R²= NCCH₂). Refer to Scheme 1

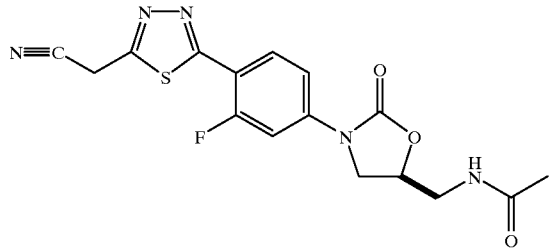

Step 1. To a stirred solution of cyanoacetic acid (10.0 mmol) in CH₂Cl₂ (40 mL) is added oxalyl chloride (11.0 mmol) followed by 2 drops of DMF. The reaction mixture is stirred at RT for 1–18 h, then concentrated. The cyanoacetyl chloride is isolated by distillation.

Step 2. The thiohydrazide XVI of Step 4 of Example 3 (216 mg) is reacted with cyanoacetyl chloride (82 mg) according to the procedure of Step 5 of Example 3 to afford 164 mg of the title compound.

Physical characteristics are as follows: mp 250–251° C. ¹H-NMR (DMSO) δ 8.26, 7.76, 7.56, 4.75, 4.17, 3.79, 3.42, 1.81. % Water (KF)=0.65. Anal. Found: C, 50.03; H, 3.91; N, 17.98; S, 8.33.

EXAMPLE 14

(S)-5-[4-[5-[(Acetylamino)methyl]-2-oxo-3-oxazolidinyl]-2-fluorophenyl]-1,3,4-thiadiazole-2-acetamide. (I-A, X¹=H, X²=F, R¹=CH₃CO, R²= H₂NCOCH₂). Refer to Scheme 1

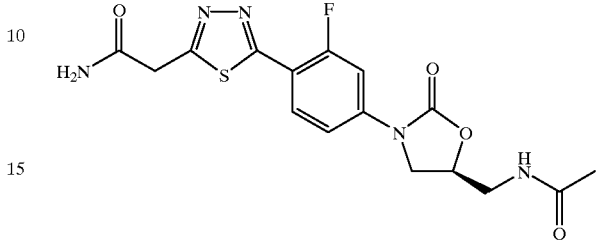

A solution of the nitrile of Example 13 (378 mg) in 7 mL of 10:1 H₂SO₄/H₂O is heated at 40° C. for 3 h. The cooled reaction mixture is poured onto 20 mL of ice and the pH is adjusted to 7 with 50% NaOH. A tan precipitate forms. The solid is isolated by filtration, washing with H₂O and drying. The solid is dissolved in MeOH/CH₂Cl₂, absorbed onto silica gel and purified by flash chromatography using 10% MeOH in CH₂Cl₂ as the eluent to afford 227 mg of the title compound.

Physical characteristics are as follows: mp 248–249° C. ¹H-NMR (DMSO) δ 8.24, 7.81, 7.72, 7.53, 7.31, 4.76, 4.17, 4.09, 3.80, 3.42, 1.81; % Water (KF)=1.02; Anal. Found: C, 48.35; H, 4.17, N, 17.01, S, 7.80.

EXAMPLE 15

(S)-N-[[3-[3-Fluoro-4-[5-(trifluoromethyl)-1,3,4-thiadiazol-2-yl]phenyl]-2-oxo-5-oxazolidinyl] methyl]acetamide. (I-A, X¹=H, X²=F, R¹=CH₃CO, R²=CF₃). Refer to Scheme 1

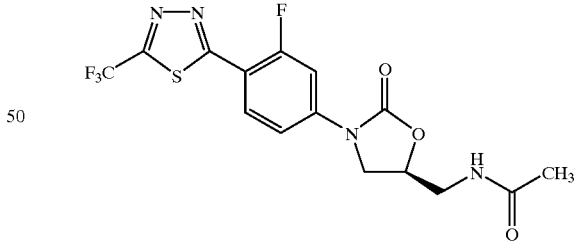

The thiohydrazide XVI from Step 4 of Example 3 (300 mg) is refluxed in neat trifluoroacetic acid (3 mL) for 8 h and then stirred overnight at rt. The reaction mixture is then concentrated in vacuo. The residue is triturated with C₃CN to afford 156 mg of the title compound.

Physical characteristics are as follows: mp 237–239° C. ¹H-NMR (DMSO) δ 8.38, 8.26, 7.78, 7.61, 4.78, 4.19, 3.81, 3.43, 1.82. Anal. Found: C, 44.97; H, 3.12; N, 13.90.

EXAMPLE 16

(S)-N-[[3-[3-Fluoro-4-[5-(3-oxobutyl)-1,3,4-thiadiazol-2-yl]phenyl]-2-oxo-5-oxazolidinyl]methyl]acetamide. (I-A, $X^1$=F, $X^2$=H, $R^1$=$CH_3CO$, $R^2$=$CH_3COCH_2CH_2$). Refer to Scheme 1

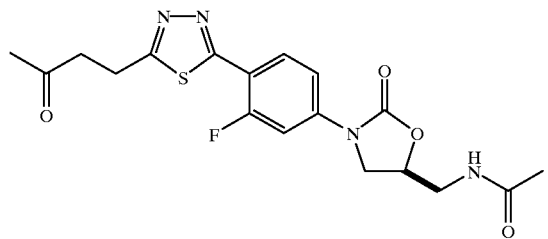

Step 1. Levulinyl chloride is prepared from levulinic acid and oxalyl chloride following the procedure of Step 1, Example 13.

Step 2. The thiohydrazide XVI of Step 4 of Example 3 (328 mg) is reacted with levulinyl chloride (268 mg) according to the procedure of Step 5, Example 3 to afford 323 mg of the title compound.

Physical characteristics are as follows: mp 209–210° C. $^1$H-NMR (DMSO) δ 8.23, 7.68, 7.52, 4.76, 4.16, 3.78, 3.42, 3.28, 3.03, 2.13, 1.81. Anal. Found: C, 52.86; H, 4.71; N, 13.79; S, 7.76.

EXAMPLE 17

(5S)-N-[[3-[3-Fluoro-4-[5-(3-hydroxybutyl)-1,3,4-thiadiazol-2-yl]phenyl]-2-oxo-5-oxazolidinyl]methyl]acetamide. (I-A, $X^1$=H, $X^2$=F, $R^1$=$CH_3CO$, $R^2$=$CH_3CH(OH)CH_2CH_2$). Refer to Scheme 1

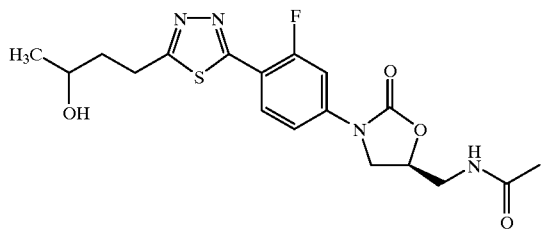

To a stirred suspension of the ketone of Example 16 (280 mg) in methanol, cooled to 0° C., is added sodium borohydride (52 mg). The reaction mixture is stirred at room temperature for 1 h, then additional sodium borohydride (25 mg) is added. Stirring is continued for an additional 3 h, then the reaction mixture is treated with water. The reaction mixture is poured into $CH_2Cl_2$ (50 mL) and the phases are separated. The aqueous phase is extracted with $CH_2Cl_2$ (3×25 mL) and the combined organic phases are dried ($MgSO_4$), filtered and concentrated. The residue is dissolved in methanol, absorbed onto silica gel and purified by flash chromatography using 5% MeOH in $CH_2Cl_2$ as the eluent to afford 130.3 mg of the title compound as a white solid.

Physical characteristics are as follows: mp 200–201° C. $^1$H-NMR (DMSO) δ 8.23, 7.72, 7.53, 4.76, 4.62, 4.17, 3.78, 3.67, 3.42, 3.16, 1.81, 1.10. Anal. Found: C, 52.59; H, 5.16; N, 13.63; S, 7.78.

EXAMPLE 18

(S)-Methyl 5-[4-[5-[(acetylamino)methyl]-2-oxo-3-oxazolidinyl]-2-fluorophenyl]-1,3,4-thiadiazole-2-propanoate. (I-A, $X^1$=F, $X^2$=H, $R^1$=$CH_3CO$, $R^2$=$CH_3OCOCH_2CH_2$). Refer to Scheme 1

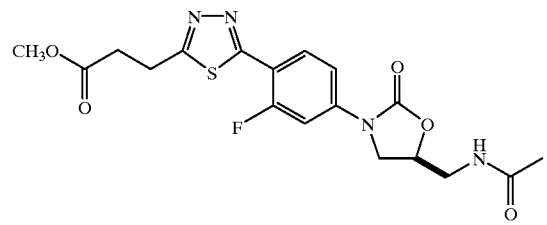

The thiohydrazide XVI of Example 3 (346 mg) is reacted with 3-carbomethoxypropionyl chloride (335 mg) according to the procedure of Step 5, Example 3 to afford 327 mg of the title compound.

Physical characteristics are as follows: mp 200–202° C. $^1$H-NMR (DMSO) δ 8.22, 7.70, 7.52, 4.76, 4.17, 3.78, 3.60, 3.40, 2.89, 1.81. Anal. Found: C, 51.06; H, 4.52; N, 13.23; S, 7.42.

EXAMPLE 19

(S)-5-[4-[5-[(Acetylamino)methyl]-2-oxo-3-oxazolidinyl]-2-fluorophenyl]-1,3,4-thiadiazole-2-propanamide. (I-A, $X^1$=H, $X^2$=F, $R^1$=$CH_3CO$, $R^2$=$NH_2COCH_2CH_2$). Refer to Scheme 1

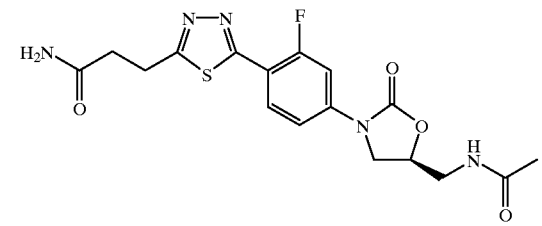

The ester of Example 18 (156.7 mg) in methanolic ammonia(7 mL) is heated in a sealed tube at 100° C. for 12 h. A solid precipitate forms upon cooling. The solid is isolated by filtration, washed with ether and dried to afford 115.0 mg of the title compound as a white solid.

Physical characteristics are as follows: mp 254–255° C. $^1$H-NMR (DMSO) δ 8.22, 7.72, 7.53, 7.41, 6.90, 4.76, 4.17, 3.79, 3.42, 2.60, 1.81. Anal. Found: C, 49.71; H, 4.49; N, 17.13; S, 7.87.

EXAMPLE 20

(S)-N-[[3-[4-[5-(2-Cyanoethyl)-1,3,4-thiadiazol-2-yl]-3-fluorophenyl]-2-oxo-5-oxazolidinyl]methyl]acetamide. (I-A, $X^1$=H, $X^2$=F, $R^1$=$CH_3CO$, $R^2$=$NCCH_2CH_2$). Refer to Scheme 1

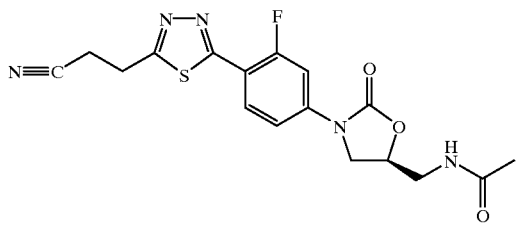

To a stirred suspension of the amide of Example 19 (110 mg) in dry THF (1.4 mL) and pyridine (0.42 mL) cooled to 0° C. is added trifluoroacetic anhydride (96 µL). The reaction mixture is stirred at 0° C., and then at RT for 2 h. The reaction mixture is concentrated and the residue is purified by flash chromatography using 5% MeOH in $CH_2Cl_2$ as the eluent to afford 64 mg of the title compound.

Physical characteristics are as follows: mp 208–210° C. $^1$H-NMR (DMSO) δ 8.25, 7.72, 7.54, 4.77, 4.16, 3.81, 3.50, 3.48, 3.06, 1.81; % Water (KF)=0.4; Anal. Found: C, 51.63; H, 4.18; N, 17.23; S, 7.92.

EXAMPLE 21

(S)-N-[[3-[3-Fluoro-4-[5-[(methylthio)methyl]-1,3,4-thiadiazol-2-yl]phenyl]-2-oxo-5-oxazolidinyl]methyl]acetamide. (I-A, $X^1$=F, $X^2$=H, $R^1$=$CH_3CO$, $R^2$=$CH_3SCH_2$). Refer to Scheme 1

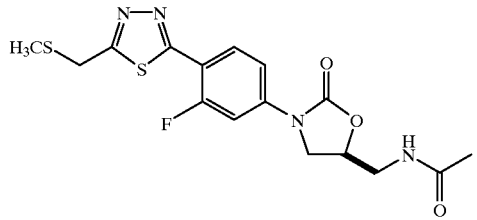

Step 1. (Methylthio)acetyl chloride is prepared as described in *J. Chem. Soc., Perkins Trans.* I 1996, 853.

Step 2. The thiohydrazide XVI of Example 3 (628 mg) is reacted with (methylthio)acetyl chloride (480 mg) according to the procedure of Step 5, Example 3 to afford 573 mg of the title compound.

Physical characteristics are as follows: mp 209–211° C. $^1$H-NMR (DMSO) δ 8.25, 7.70, 7.55, 4.76, 4.23, 4.17, 3.82, 3.42, 2.10, 1.81. Anal. Found: C, 48.36; H, 4.38; N, 14.05; S, 16.04.

EXAMPLE 22

(S)-N-[[3-[3-Fluoro-4-[5-[(methylsulfinyl)methyl]-1,3,4-thiadiazol-2-yl]phenyl]-2-oxo-5-oxazolidinyl]methyl]acetamide. (I-A, $X^1$=H, $X^2$=F, $R^1$=$CH_3CO$, $R^2$=$CH_3S(O)CH_2$). Refer to Scheme 1

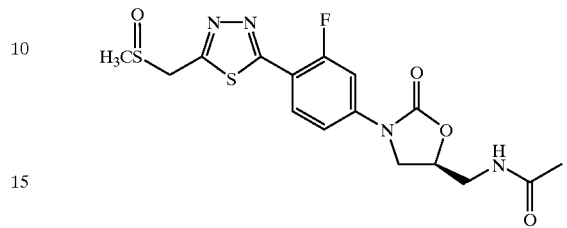

To a stirred suspension of the sulfide of Example 21 (110 mg) in 1:1 methanol/water (4.4 mL) is added sodium metaperiodate (65 mg). The reaction mixture is heated at reflux for 30 min, during which time the reaction mixture becomes homogeneous. The reaction mixture is cooled and a solid precipitate forms. The solid is removed by filtration and the filtrate is concentrated. The resulting residue is dissolved in $MeOH/CH_2Cl_2$, absorbed onto silica gel and purified by flash chromatography using 5% MeOH in $CH_2Cl_2$ as the eluent to afford 89 mg of the title compound.

Physical characteristics are as follows: mp 200–201° C. $^1$H-NMR (DMSO) δ 8.29, 8.23, 7.74, 7.55, 4.84, 4.77, 4.64, 4.18, 3.80, 3.42, 2.56, 1.81; Anal. Found: C, 46.32; H, 4.18; N, 13.38; 15.44.

EXAMPLE 23

(S)-N-[[3-[3-Fluoro-4-[5-[2-(methylthio)ethyl]-1,3,4-thiadiazol-2-yl]phenyl]-2-oxo-5-oxazolidinyl]methyl]acetamide. (I-A, $X^1$=F, $X^2$=H, $R^1$=$CH_3CO$, $R^2$=$CH_3SCH_2CH_2$). Refer to Scheme 1

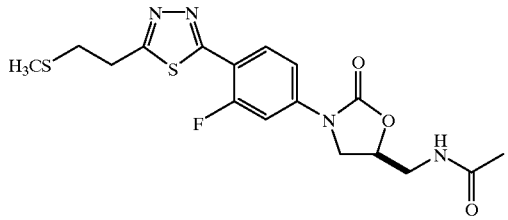

Step 1. 3-(Methylthio)propionyl chloride is prepared according to the procedure found in Synthesis, 1986, 1070.

Step 2. The thiohydrazide XVI of Example 3 (357 mg) is reacted with 3-(methylthio)propionyl chloride (299 mg) according to the procedure of Step 5, Example 3 to afford 404 mg of the title compound.

Physical characteristics are as follows: mp 211–213° C. $^1$H-NMR (DMSO) d 8.24, 7.69, 7.53, 4.77, 4.17, 3.79, 3.42, 2.91, 2.10, 1.81. Anal. Found: C, 49.90; H, 4.79; N, 13.50; S, 15.37.

EXAMPLE 24

(S)-N-[[3-[3-Fluoro-4-[5-[2-(methylsulfinyl)ethyl]-1,3,4-thiadiazol-2-yl]phenyl]-2-oxo-5-oxazolidinyl]methyl]acetamide. (I-A, $X^1$=H, $X^2$=F, $R^1$=$CH_3CO$, $R^2$=$CH_3S(O)CH_2CH_2$). Refer to Scheme 1

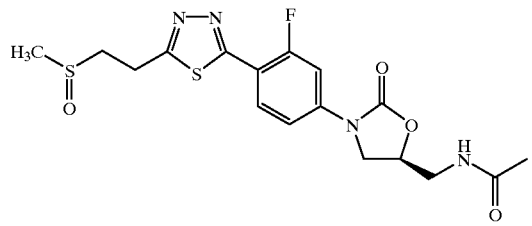

To a stirred suspension of the sulfide of Example 23 (170 mg) in 6.4 mL MeOH/H$_2$O (1:1) is added sodium metaperiodate (97 mg). The reaction is heated to reflux for 15 min. during which time the reaction mixture becomes homogeneous. The reaction mixture is cooled and a precipitate forms. The solid is removed by filtration and the filtrate is absorbed onto silica gel and purified by flash chromatography using 7% MeOH in CH$_2$Cl$_2$ as the eluent to afford 150 mg of the title compound as a white solid.

Physical characteristics are as follows: mp 193–914° C. $^1$H-NMR (DMSO) δ 8.24, 7.74, 7.54, 4.76, 4.17, 3.79, 3.55, 3.42, 3.16, 2.61, 1.81. Anal. Found: C, 47.70; H, 4.64; N, 13.02; S, 14.83.

EXAMPLE 25

(S)-Ethyl 5-[4-[5-[(acetylamino)methyl]-2-oxo-3-oxazolidinyl]-2-fluorophenyl]-1,3,4-thiadiazole-2-acetate. (I-A, $X^1$=F, $X^2$=H, $R^1$=$CH_3CO$, $R^2$=$CH_3CH_2OCOCH_2$). Refer to Scheme 1

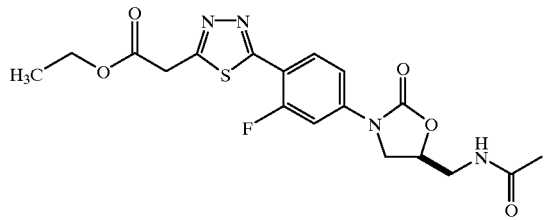

The thiohydrazide XVI of Example 3 (587 mg) is reacted with ethyl malonyl chloride (352 mg) according to the procedure of Step 5, Example 3 to afford 539 mg of the title compound.

Physical characteristics are as follows: mp 158–159° C. $^1$H-NMR (DMSO) δ 8.26, 7.72, 7.52, 4.76, 4.38, 4.15, 3.79, 3.69, 3.42, 1.82, 1.21. Anal. Found: C, 50.94; H, 4.61; N, 13.22; S, 7.56.

EXAMPLE 26

(S)-N-[[3-[3-Fluoro-4-[5-(2-hydroxyethyl)-1,3,4-thiadiazol-2-yl]phenyl]-2-oxo-5-oxazolidinyl]methyl]acetamide. (I-A, $X^1$=H, $X^2$=F, $R^1$=$CH_3CO$, $R^2$=$HOCH_2CH_2$). Refer to Scheme 1

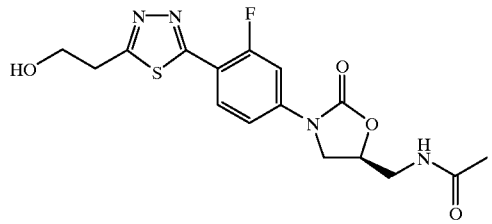

To a stirred suspension of the ester of Example 25 (138 mg) in isopropanol (3 mL) is added a 2 M solution of lithium borohydride in THF (0.33 mL). The bright yellow reaction mixture is stirred at RT for 4 h, then quenched with water. The reaction mixture is concentrated. The residue is dissolved in MeOH/CH$_2$Cl$_2$, absorbed onto silica gel and purified by flash chromatography using 7% MeOH in CH$_2$Cl$_2$ as the eluent to afford 54.0 mg of the title compound as a white solid.

Physical characteristics are as follows: mp 192–194° C. $^1$H-NMR (DMSO) δ 8.24, 7.70, 7.51, 5.08, 4.77, 4.17, 3.76, 3.42, 3.25, 1.81. Anal. Found: C, 50.09; H, 4.62; N, 14.71; S, 8.22.

EXAMPLE 27

(S)-Ethyl 5-[4-[5-[(acetylamino)methyl]-2-oxo-3-oxazolidinyl]-2-fluorophenyl]-1,3,4-thiadiazole-2-carboxylate. (I-A, $X^1$=F, $X^2$=H, $R^1$=$CH_3CO$, $R^2$=$CH_3CH_2OCO$). Refer to Scheme 1

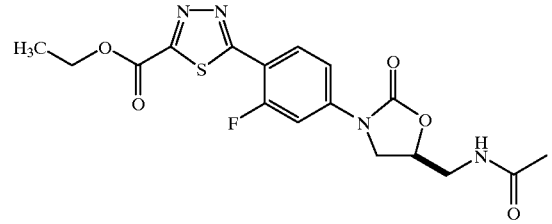

The thiohydrazide XVI of Example 3 (364 mg) is reacted with ethyl oxalyl chloride (198 mg) according to the procedure of Step 5, Example 3 to afford 332 mg of the title compound.

Physical characteristics are as follows: mp 220–222° C. $^1$H-NMR (DMSO) δ 8.37, 8.23, 7.76, 7.59, 4.77, 4.43, 4.18, 3.81, 3.42, 3.29, 1.81, 1.35. Anal. Found: C, 49.53; H, 4.23; N, 13.53; S, 7.79.

EXAMPLE 28

(5S)-N-[[3-[3-Fluoro-4-[5-(2-hydroxypropyl)-1,3,4-thiadiazol-2-yl]phenyl]-2-oxo-5-oxazolidinyl]methyl]acetamide. (I-A, $X^1$=H, $X^2$=F, $R^1$=$CH_3CO$, $R^2$=$CH_3CH(OH)CH_2$). Refer to Scheme 1

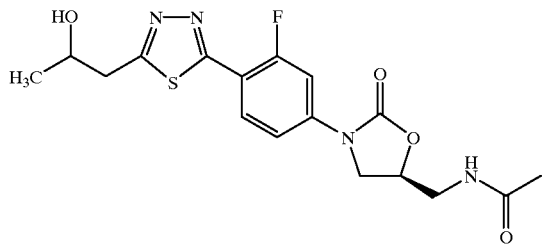

Step 1. 3-(tert-Butyldimethylsiloxy)butyryl chloride is prepared according to the procedure found in *J. Org. Chem.* 1987, 52, 1780–1789.

Step 2. The thiohydrazide XVI of Example 3 (323 mg) is reacted with 3-(tert-butyldimethylsiloxy) butyryl chloride (468 mg) according to the procedure of Step 5, Example 3 to afford 219 mg of the title compound.

Physical characteristics are as follows: mp 200–202° C. $^1$H-NMR (CDCl$_3$) δ 4.35, 2.95, 1.23, 0.87. 0.07. Anal. Found: C, 51.42; h, 4.89; N, 14.03; S, 7.93.

EXAMPLE 29

(S)-N-[[3-[4-(4,5-Dihydro-5-oxo-1,3,4-thiadiazol-2-yl)-3-fluorophenyl]-2-oxo-5-oxazolidinyl]methyl]acetamide. (I-A, $X^1$=H, $X^2$=F, $R^1$=$CH_3CO$, $R^2$=HO). Refer to Scheme 1

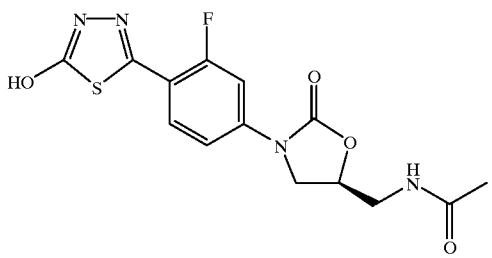

To a stirred suspension of the thiohydrazide XVI of Step 4 of Example 3 (339 mg) in THF (10 mL) is added diphosgene (0.16 mL). The reaction is heated at reflux for 1 h. The cooled reaction is concentrated. The residue is dissolved in MeOH/CH$_2$Cl$_2$, absorbed onto silica gel and purified by flash chromatography to afford 54 mg of the title compound.

Physical characteristics are as follows: mp 230–232° C. 1H-NMR (DMSO) δ 8.22, 7.88, 7.50, 7.46, 4.74, 4.15, 3.76, 3.41, 1.81.

EXAMPLE 30

(S)-N-[[3-[4-(5-Amino-1,3,4-thiadiazol-2-yl)-3-fluorophenyl]-2-oxo-5-oxazolidinyl]methyl]acetamide (I-A, $X^1$=F, $X^2$=H, $R^1$=$CH_3CO$, $R^2$=$H_2N$)

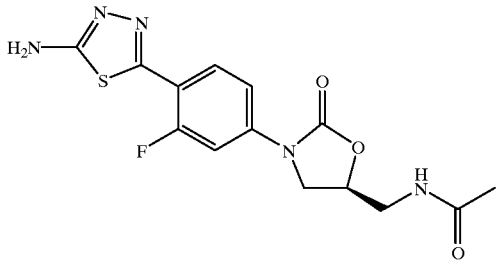

Another method of making the compounds of formula I-A is as follows: A mixture of the nitrile XII (prepared in step 1 of Example 3, 1.22 g) and thiosemicarbazide (441.2 mg) in methane sulfonic acid (5 mL) is heated at 70° C. for 45 min. The cooled reaction mixture is treated with 1 N NH$_4$OH, until precipitation occurs. The yellow precipitate is isolated by filtration and dried. This solid is dissolved in hot ethanol and water and the solution is made alkaline (pH 8) with 1 N NH$_4$OH. Upon cooling, a solid is deposited. The solid is isolated by filtration, washed with water and dried in a vacuum oven at 40° C. overnight to afford 982.7 mg of the title thiadiazole.

Physical characteristics are as follows: mp 261–262° C. (dec). $^1$H NMR (DMSO) δ 8.24, 8.06, 7.62, 7.45, 4.74, 4.14, 3.76, 3.41, 1.81; % Water (KF)=0.35%. Anal. Found: C, 47.42; H, 4.09; N, 19.75; S, 9.14.

EXAMPLE 31

(S)-N-[[3-[3-Fluoro-4-[5-(methylthio)-1,3,4-thiadiazol-2-yl]phenyl]-2-oxo-5-oxazolidinyl]methyl]acetamide. (I-A, $X^1$=H, $X^2$=F, $R^1$=$CH_3CO$, $R^2$=$CH_3S$). Refer to Scheme 1

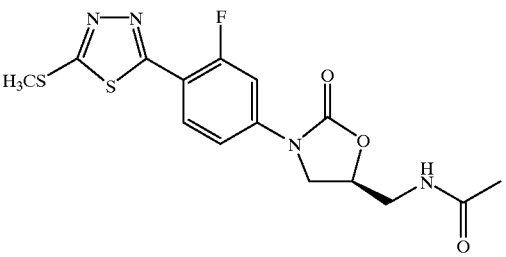

Step 1. Methyl hydrazinecarbodithioate is prepared according to the procedure in *J. Med. Chem.* 1979, 22, 855–862).

Step 2. A mixture of the nitrile XII prepared in Step 1, Example 3 (266 mg) and methyl hydrazinecarbodithioate (293 mg) in methane sulfonic acid (4 mL) is heated at 65° C. for 18 h. The cooled reaction mixture is cooled and treated with 1 M aqueous NH$_4$OH after which a solid precipitate forms. The solid is isolated by filtration. The solid is dissolved in MeOH/CH$_2$Cl$_2$, absorbed onto silica gel and purified using a Biotage 40 S column using 3% MeOH in CH$_2$Cl$_2$ as eluent to afford 124.5 mg of the title compound as a white solid.

Physical characteristics are as follows: mp 196–198° C. $^1$H-NMR (DMSO) δ 8.23, 7.75, 7.54, 4.77, 4.16, 3.78, 3.42, 2.80, 1.81. % Water (KF) 2.50; Anal. Found: C, 45.51; H, 3.88; N, 14.15; S, 16.22.

EXAMPLE 32

(S)-N-[[3-[3-Fluoro-4-(5-methyl-1,3,4-thiadiazol-2-yl)phenyl]-2-oxo-5-oxazolidinyl]methyl] propanamide. (I-A, $X^1$=H, $X^2$=F, $R^1$=CH$_3$CH$_2$CO, $R^2$=CH$_3$). Refer to Scheme 1

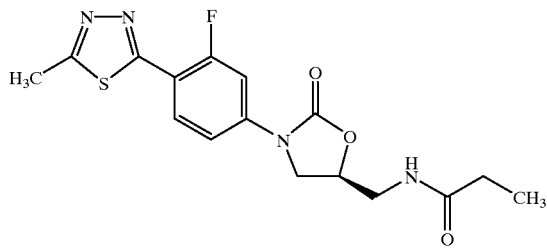

Step 1. To a solution of hydroxylamine hydrochloride (732 mg) in pyridine (25 mL) is added the title compound of Example 3 (693 mg). The mixture turns homogenous with the addition of EtOH (2.5 mL). The reaction mixture is heated to reflux for 4 hours. The reaction is cooled to room temperature and the precipitated product is collected by filtration to afford 124 mg of the aminomethyl oxazolidinone.

Step 2. To a suspension of the compound prepared in Step 1 (200 mg) in 10 mL of CH$_2$Cl$_2$ is added propionyl chloride (113 μL) and triethylamine (362 μL). The reaction is heated to 70° C. for 2 hours. The reaction is concentrated and the residue is triturated with Et$_2$O. Further purification by chromatography using 5% MeOH/CH$_2$Cl$_2$ as eluent gives 189 mg of the title compound.

Physical characteristics are as follows: mp 249–251° C. $^1$H-NMR (DMSO) δ 8.20, 7.69, 7.51, 4.78, 4.17, 3.82, 3.43, 2.77, 2.08, 0.93. Anal. Found: C, 52.78; H, 4.66; N, 15.32.

EXAMPLE 33

(S)-3-[4-[5-[(Acetylamino)methyl]-2-oxo-3-oxazolidinyl]-2-fluorophenyl]-1,2,4-thiadiazole-5-carboxamide (I-B, $X^1$=H, $X^2$=F, $R^1$=COCH$_3$, $R^2$= NH$_2$CO). Refer to Scheme 2

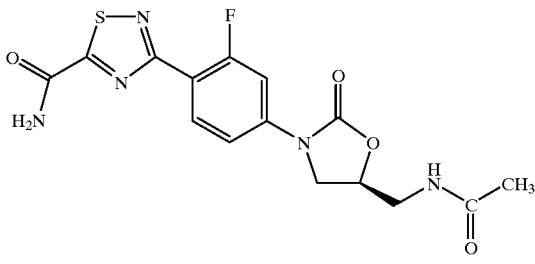

Step 1. The nitrile XII (prepared in step 1 of Example 3, 1.11 g) is dissolved in warm DMSO (3.0 mL) and powdered potassium carbonate (100 mg) is added. The mixture is cooled to 15° C. and 30% hydrogen peroxide (900 uL) is added. A vigorous exothermic reaction begins and after it subsides, the cooling bath is removed and the reaction stirred 15 minutes at 20° C. The reaction is diluted with ethanol (100 mL) and toluene (200 mL) and filtered, then concentrated in vacuo to an orange oil. The oil is chromatographed over silica gel, eluting with 10% methanol in methylene chloride. The product is recrystallized from ethyl acetate to give 840 mg of the product XVII as white crystals.

Physical characteistics as follows: mp 219–20° C.; $^1$H NMR (300 MHz, DMSO) δ 8.27, 7.71, 7.56, 7.53, 7.34, 4.72, 4.12, 3.74, 3.40, 1.80; Anal. Found: C, 52.55; H, 4.90; N, 14.12.

Step 2. The amide XVII prepared in step 1 (100 mg) is dispersed in acetonitrile (4 mL) and chlorocarbonyl sulfenyl chloride (70 uL) is added. The reaction is warmed to 80° C. for 1.5 hours. The solvent is evaporated and the residue is chromatographed over silica gel, eluting with 5% methanol in methylene chloride to give the product XVIII (47 mg) as a tan solid.

Physical characteristics are as follows: mp 175° C., dec.$^1$H NMR (300 MHz, DMSO) δ 8.24, 7.92, 7.65, 7.51, 4.75, 4.16, 3.78, 3.41, 1.81;

Step 3. The 1,3,4-oxathiazole-2-one XVIII prepared in step 2 (40 mg) is mixed with ethylcyanoformate (1.5 mL) in toluene (3.0 mL) and heated to reflux (130° C.) for 17 hours. The solvent is evaporated under a stream of dry nitrogen and the residue is chromatographed over silica gel, eluting with 5% methanol in methylene chloride to afford 21 mg of the ethyl thiadiazolecarboxylate (I-B, $R^2$=CH$_3$CH$_2$CO) as a yellow solid.

Physical characteristics are as follows: mp 115–117° C.,$^1$HNMR (300 MHz, CDCl$_3$) δ 8.25, 7.60, 7.28, 6.43, 4.83, 4.53, 4.11, 3.84, 3.69, 2.03, 1.46.

Step 4. The ethyl thiadiazolecarboxylate prepared in Step 3 (175 mg) is dissolved in methanol (10 mL) and methanol saturated with ammonia (5 mL) is added. The reaction is stirred at 20° C. for 2 hours. A tan precipitate forms. The solution is diluted with warm methanol (10 mL) and treated with decolorizing carbon and filtered. The solution is concentrated and the residue is recrystallized from ethyl acetate/methanol, to give 120 mg of the title compound as tan crystals.

Physical characteristics are as follows: mp=238–240° C. $^1$H NMR (300 MHz, DMSO) δ 8.53, 8.26, 8.24, 7.67, 7.49, 4.77, 4.18, 3.80, 3.42, 1.82. HRMS (FAB) found for $C_{15}H_{14}FN_5O_4S$+H1, 380.0822.

EXAMPLE 34

(S)-N-[[3-[3-Fluoro-4-(1,2,4-thiadiazol-5-yl) phenyl]-2-oxo-5-oxazolidinyl]methyl]acetamide (I-C, $X^1$=F, $X^2$=H, $R^1$=COCH$_3$, $R^2$=H). Refer to Scheme 3

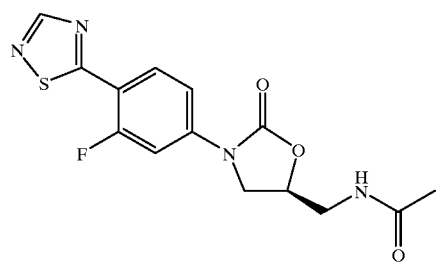

Step 1: A mixture of thioamide XIII, prepared as described in Step 2 of Example 3 (0.500 g) and N,N- dimethylformamide dimethyl acetal (257 μL) in dry methylene chloride (3.2 mL) is stirred under nitrogen for 1 hr. The reaction mixture is then triturated with diethyl ether and the orange precipitate filtered and dried under reduced pressure to give the amidine which is not further purified but is used directly in the next step. mp 163–165° C. (decomp.).

Step 2: A mixture of the amidine prepared in step 1 (0.250 g) in absolute ethanol (1.7 mL) and pyridine (0.11 mL) under nitrogen is treated with a solution of hydroxylamine-O-sulfonic acid (85 mg) in methanol (1.0 mL). The resulting mixture is stirred at ambient temperature for 45 mins, concentrated under reduced pressure, rediluted with water (25 mL) and extracted with methanolchloroform (10/90, 4×50 mL). The combined organic phases are then washed with aqueous sodium hydroxide (0.1 M, 50 mL), water (50 mL) and saline (20 mL), dried over anhydrous sodium sulfate and concentrated under reduced pressure to give the crude product. Purification by reverse phase HPLC (Zorbax SB-18 column, 20–60% acetonitrile/water eluent) gives 21 mg of the title compound.

Physical characteristics are as follows: mp 199–200° C. $^1$HNMR (CDCl$_3$) δ 8.71, 8.34, 7.76, 7.32, 6.17, 4.85, 4.13, 3.86, 3.72, 2.05.

EXAMPLE 35

(S)-N-[[3-[3-Fluoro-4-(5-methyl-1,2,4-oxadiazol-3-yl)phenyl]-2-oxo-5-oxazolidinyl]methyl]acetamide (I-H where $X^1$ is H, $X^2$ is F, $R^1$ is COCH$_3$ and $R^2$ is CH$_3$). Refer to Scheme 8

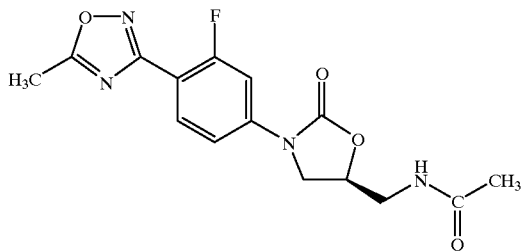

Step 1. The nitrile XII (prepared in step 1 of Example 3, 2.77 g), hydroxylamine hydrochloride (2.08 g) and powdered sodium carbonate (4.23 g) are dissolved in methanol (30 mL). The reaction is warmed to reflux for 2.5 hours and turns very dark in color. The reaction is diluted with 1:1 methylene chloride and methanol (50 mL) and filtered through celite. The celite is washed with another aliquot of solvent (50 mL) and the combined filtrates are concentrated in vacuo. The residue is chromatographed over silica gel, eluting with 10% methanol in methylene chloride to give a yellow foam which is crystallized from methanol/ethyl acetate to give 2.2 g of the hydroxyamidine XXII as a yellow crystalline solid.

Physical characteristics are as follows: mp 196–7° C. dec.;$^1$H NMR (300 MHz, DMSO) δ 9.63, 8.26, 7.50, 7.31, 5.78, 4.75, 4.13, 3.75, 3.42, 1.83; Anal. Found: C, 50.23; H, 4.89; N, 17.96.

Step 2. The hydroxyamidine XXII prepared in step 1 (310 mg) is dissolved in acetic anhydride (3 mL) and heated at 120° C. for 3 hours. The solvent is evaporated under a stream of dry nitrogen and the residue is chromatographed over silica gel, eluting with 10 % methanol in methylene chloride to give a white solid. The product is recrystallized from ethyl acetate/hexane as white needles to afford 145 mg of title product.

Physical characteristics are as follows: mp 177–9° C. $^1$H NMR (300 MHz, CDCl$_3$) δ 8.02, 7.62, 7.31, 6.13, 4.82, 4.10, 3.83, 3.68, 2.66, 2.03; Anal. Found: C, 53.55; H, 4.64; N, 16.41.

EXAMPLE 36

(S)-N-[[3-[3-Fluoro-4-(1,2,4-oxadiazol-3-yl)phenyl]-2-oxo-5-oxazolidinyl]methyl]acetamide(I-H where $X^1$ is H, $X^2$ is F, $R^1$ is COCH$_3$ and $R^2$ is H). Refer to Scheme 8

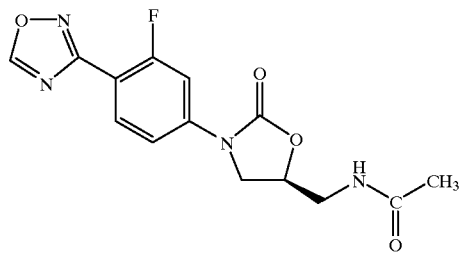

The hydroxyamidine XXII (prepared in step 1 of Example 35, 200 mg) is dispersed in triethyl orthoformate (3 mL) and heated at reflux until all starting material is gone by TLC. Triethylamine (3 equivalents) and methanol (2 mL) are added and the mixture is stirred at 50° C. for 17 hours. The solvent is evaporated and the residue is chromatographed over silica gel to give 47 mg of the desired product as a white solid.

Physical characteristics are as follows: mp 197–9° C. $^1$H NMR (300 MHz, DMSO) δ 9.77, 8.27, 8.08, 7.75, 7.56, 4.78, 4.19, 3.81, 3.44, 1.83; Anal. Found: C, 52.51; H, 4.45; N, 16.37.

EXAMPLE 37

(S)-3-[4-[5-[(Acetylamino)methyl]-2-oxo-3-oxazolidinyl]-2-fluorophenyl]-1,2,4-oxadiazole-5-carboxamide (I-H where $X^1$ is H, $X^2$ is F, $R^1$ is COCH$_3$ and $R^2$ is H$_2$NCO). Refer to Scheme 8

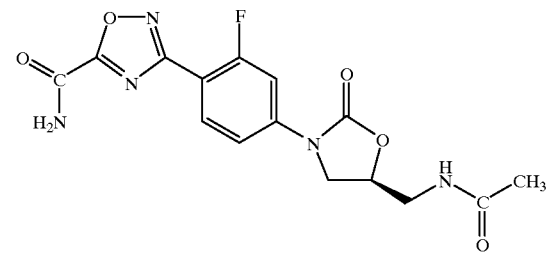

Step 1. The hydroxyamidine XXII (prepared in step I of example 35, 930 mg), is dissolved in pyridine (1.0 mL) and methylene chloride (10 mL) and the solution is stirred at 20° C. Ethyl oxalyl chloride (285 uL) is added dropwise and the reaction is stirred for 1 hour. The solvent is evaporated under a stream of nitrogen and the residue is chromatographed over silica gel, eluting with 10% methanol in methylene chloride, to give 700 mg of crude oxadiazole ester.

Step 2. The crude ester prepared in step 1 (700 mg) is dissolved in methanol (15 mL) and methanol saturated with ammonia (10 mL) is added. The reaction is stirred 3 hours at ambient temperature and then cooled in a refrigerator for 2 hours. The product crystallizes from the reaction mixture and is collected by filtration to afford 315 mg of title product.

Physical characteristics are as follows: mp 218–20° C.;¹H NMR (300 MHz, DMSO) δ 8.80, 8.48, 8.27, 8.08, 7.74, 7.58, 4.80, 4.20, 3.82, 3.45, 1.84; Anal. Found: C, 48.35; H, 4.13; N, 18.48.

EXAMPLE 38

(S)-N-[[3-[4-(5-Cyano-1,2,4-oxadiazol-3-yl)-3-fluorophenyl]-2-oxo-5-oxazolidinyl]methyl]acetamide(I-H where $X^1$ is H, $X^2$ is F, $R^1$ is COCH$_3$ and $R^2$ is CN)

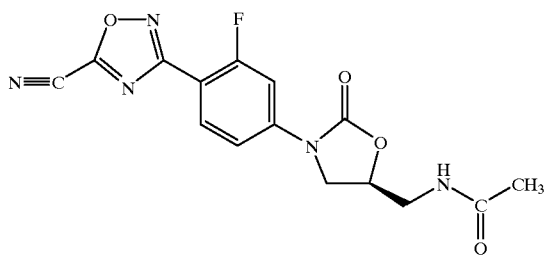

The title amide of Example 37 (150 mg) is dissolved in pyridine (1.0 mL) and THF (2.0 mL) and cooled to 0° C. Trifluoroacetic anhydride (170 uL) is added. The reaction is stirred for 20 minutes, then allowed to warm to ambient temperature and stirred for 17 hours. The solvent is evaporated under dry nitrogen and the residue is chromatographed over silica gel, eluting with 10% methanol in methylene chloride to give a white solid. Recrystallization from ethyl acetate/hexane gives 110 mg of the title product as white needles.

Physical characteristics are as follows: mp 200–2° C. ¹H NMR (300 MHz, CDCl$_3$) δ 7.98, 7.67, 7.31, 7.26, 4.78, 4.04, 3.83, 3.58, 1.93; Anal. Found: C, 51.98; H, 3.72; N, 20.00.

EXAMPLE 39

(S)-N-[[3-[3-Fluoro-4-[5-(trifluoromethyl)-1,2,4-oxadiazol-3-yl]phenyl]-2-oxo-5-oxazolidinyl]methyl]acetamide(I-H where $X^1$ is H, $X^2$ is F, $R^1$ is COCH$_3$ and $R^2$ is CF$_3$). Refer to Scheme 8

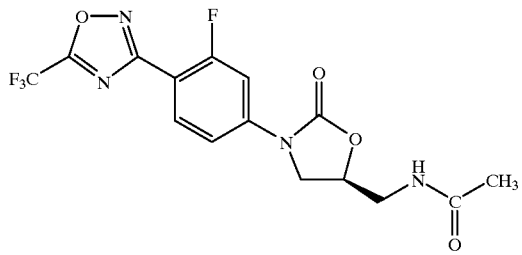

The hydroxyamidine XXII prepared in step 1 of Example 35 (310 mg) is dissolved in pyridine (3.0 mL) and trifluoroacetic anhydride (282 uL) is added at 20° C. The reaction is stirred for 10 minutes, and then warmed to reflux for 30 minutes. The reaction is allowed to slowly cool and then the solvent is evaporated under a stream of dry nitrogen. The residue is chromatographed over silica gel, eluting with 10% methanol in methylene chloride to give a white solid which is recrystallized from ethyl acetate/hexane to afford 295 mg of the title product.

Physical characteristics are as follows: mp 192–3° C. ¹H NMR (300 MHz, DMSO) δ 8.27, 8.10, 7.74, 7.60, 4.80, 4.20, 3.81, 3.44, 1.83. Anal. Found: C, 46.21; H, 3.25; N, 14.29.

EXAMPLE 40

(S)-N-[[3-[3-Fluoro-4-(1,2,4-oxadiazol-5-yl)phenyl]-2-oxo-5-oxazolidinyl]methyl]acetamide (I-I, $X^1$ =F, $X^2$=H, $R^1$=COCH$_3$, $R^2$=H)

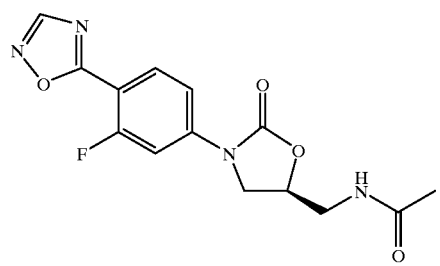

The title compound (57 mg) is obtained as a byproduct from the procedure of example 34.

Physical characteristics are as follows: mp 199–200° C. ¹HNMR (CDCl$_3$) δ 9.12, 8.24, 8.17, 7.73, 7.59, 4.79, 4.20, 3.82, 3.44, 1.83. Anal. Found: C, 52.16; H, 4.13; N, 17.34.

EXAMPLE 41

(S)-N-[[3-[3-Fluoro-4-[5-(formylamino)-1,3,4-thiadiazol-2-yl]phenyl]-2-oxo-5-oxazolidinyl]methyl]acetamide (I-A, $X^1$=H, $X^2$=F, $R^1$=COCH$_3$, $R^2$=HC(O)NH)

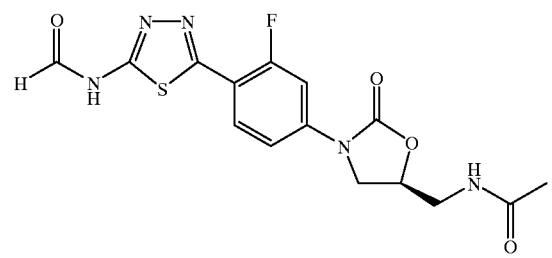

To a stirred suspension of the compound of Example 30 (184 mg) in dry THF (5 mL) is added 1H-benzotriazole-1-carboxaldehyde (168 mg). The reaction mixture is heated at reflux for 48 hours, cooled and concentrated. The residue is dissolved in EtOH/CH$_3$CN, absorbed onto silica gel and purified by flash chromatography using 7% MeOH in CH$_2$Cl$_2$ as the eluent to yield 155 mg of the title compound as a white solid.

Physical characteristics are as follows: mp 259–260° C. (dec). ¹H NMR (DMSO-d$_6$) δ 12.9, 8.53, 8.25, 7.71, 7.53, 4.76, 4.17, 3.79, 3.42, 1.81. % Water (KF)=3.65. Anal. Found: C, 46.29; H, 3.92; N, 17.65; S, 8.04.

EXAMPLE 42

(S)-N-[[3-[4-[5-(2-Chloroethyl)-1,3,4-thiadiazol-2-yl]-3-fluorophenyl]-2-oxo-5-oxazolidinyl]methyl] acetamide (I-A, $X^1$=F, $X^2$=H, $R^1$=COCH$_3$, $R^2$= ClCH$_2$CH$_2$)

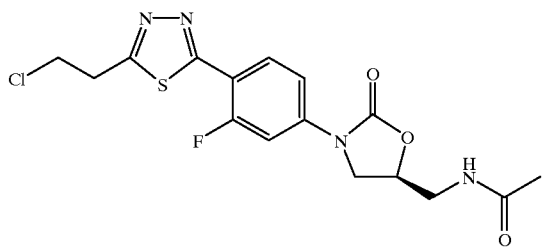

The thiohydrazide XVI of Example 3 (250 mg) is reacted with acryloyl chloride (125 μL) according to the procedure of Step 5, Example 3 to afford 196 mg of the title compound.

Physical characteristics are as follows: mp 178–180° C. $^1$H NMR (DMSO-d$_6$) δ 8.26, 7.73, 7.53, 4.76, 4.18, 4.05, 3.80, 3.63, 3.43, 1.82. Anal. Found: C, 48.94; H, 4.08; N, 13.96.

EXAMPLE 43

(S)-N-[[3-[3-Fluoro-4-[5-(1-propenyl)-1,3,4-thiadiazol-2-yl]phenyl]-2-oxo-5-oxazolidinyl] methyl]acetamide.(I-A, $X^1$=F, $X^2$=H, $R^1$=COCH$_3$, $R^2$=CH$_3$CH=CH)

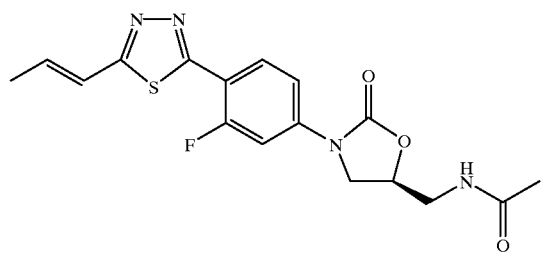

The thiohydrazide XVI from Step 4 of Example 3 (200 mg) is reacted with 3-butenoyl chloride (127 mg) according to the procedure of Step 5, Example 3 to afford 120 mg of the title compound.

Physical characteristics are as follows: mp 242–244° C. $^1$H NMR (DMSO-d$_6$) δ 8.27, 7.71, 7.53, 6.88, 6.76, 4.77, 3.80, 3.42, 1.94, 1.82. HRMS (EI) Found for $C_{17}H_{17}FN_4O_3S$, 377.1075.

EXAMPLE 44

(S)-N-[[3-[4-[5-(2-Aminoethyl)-1,3,4-thiadiazol-2-yl]-3-fluorophenyl]-2-oxo-5-oxazolidinyl]methyl] acetamide. (I-A, $X^1$=F, $X^2$=H, $R^1$=CH$_3$CO, $R^2$= H$_2$NCH$_2$CH$_2$). Refer to Scheme I

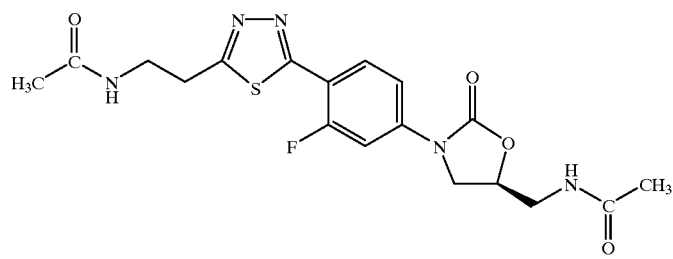

Step 1. Fmoc-β-Ala-OH (1.0 g) is suspended in methylene chloride at room temperature under nitrogen. Oxalyl chloride (298 μL) is added followed by two drops of DMF. After stirring overnight at room temperature, the reaction is concentrated to afford 0.75 g of the acid chloride (Fmoc-β-Ala-Cl).

Step 2. The thiohydrazide XVI of Example 3 (210 mg) is reacted with Fmoc-β-Ala-Cl (275 mg, from Step 1) according to the procedure of Step 5, Example 3 to afford 358 mg of the Fmoc-protected title compound.

Step 3. The Fmoc-protected amine prepared in Step 2 (1.3 g) is dissolved in piperidine (30 mL) and stirred for 1 hour at room temperature. The reaction is concentrated and the residue is purified by flash chromatography using 5% MeOH (saturated with NH$_3$) in CH$_2$Cl$_1$ to afford 0.59 g of the title compound. Physical characteristics are as follows: mp 195–197° C. $^1$H NMR (DMSO-d$_6$) δ 8.22, 7.70, 7.52, 4.76, 4.17, 3.80, 3.42, 3.32, 3.15, 2.91, 1.82. Anal. Found: C, 50.19; H, 5.07; N, 17.92; S, 8.02.

EXAMPLE 45

(S)-N-[[3-[4-[5-[2-(Acetylamino)ethyl]-1,3,4-thiadiazol-2-yl]-3-fluorophenyl]-2-oxo-5-oxazolidinyl]methyl]acetamide. (I-A, $X^1$=F, $X^2$=H, $R^1$=CH$_3$CO, $R^2$=CH$_3$C(O)NHCH$_2$CH$_2$). Refer to Scheme I The thiadiazole prepared in Example 44, Step 3 (300 mg) is combined with acetic anhydride (97 µL) and pyridine (199 µL) in 20 mL of CH₂Cl₂. The reaction is heated overnight and then concentrated in vacuo. The residue is dissolved in CH₂Cl₂ and MeOH, absorbed onto silica, and purified by flash chromatography using 5% MeOH in CH₂Cl₂ as eluent to afford 251 mg of the title compound.

Physical characteristics are as follows: mp 259–261° C. $^1$H NMR (DMSO-d$_6$) δ 8.25, 8.08, 7.70, 7.53, 4.77, 4.17, 3.79, 3.42, 3.26, 1.82, 1.78. Anal. Found: C, 51.25; H, 4.83; N, 16.59; S, 7.46.

EXAMPLE 46

(S)-N-[[3-[3-Fluoro-4-[5-[2-[(methylsulfonyl)amino] ethyl]-1,3,4-thiadiazol-2-yl]phenyl]-2-oxo-5-oxazolidinyl]methyl]acetamide. (I-A, X$^1$=F, X$^2$=H, R$^1$=CH$_3$CO, R$^2$=CH$_3$SO$_2$NHCH$_2$CH$_2$). Refer to Scheme I

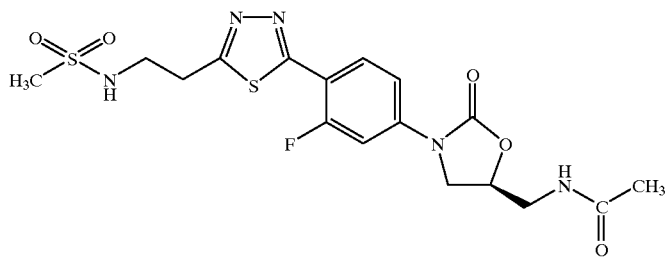

The thiadiazole prepared in Example 44, Step 3 (300 mg) is suspended in CH₂Cl₂ (10 mL) and methanesulfonyl chloride (127µL) and triethylamine (458 µL) are added. The reaction is heated to 60° C. for 3 hours and then concentrated to dryness. The residue is taken up in CH₂Cl₂ and MeOH, absorbed onto silica gel, and purified by flash chromatography using 5% MeOH in CHCl₃ as eluent to afford 145 mg of the title compound.

Physical characteristics are as follows: mp 213–214. $^1$H NMR (DMSO-d$_6$) δ 8.25, 7.71, 7.53, 7.30, 4.77, 4.17, 3.81, 3.35, 2.92, 1.82. Anal. Found: C, 44.19; H, 4.57; N, 15.08; S, 13.57.

EXAMPLE 47

(5S)-N-[[3-[3-Fluoro-4-[5-(methylsulfinyl)-1,3,4-thiadiazol-2-yl]phenyl]-2-oxo-5-oxazolidinyl] methyl]acetamide. (I-A, X$^1$=F, X$^2$=H, R$^1$=CH$_3$CO, R$^2$=CH$_3$SO). Refer to Scheme I

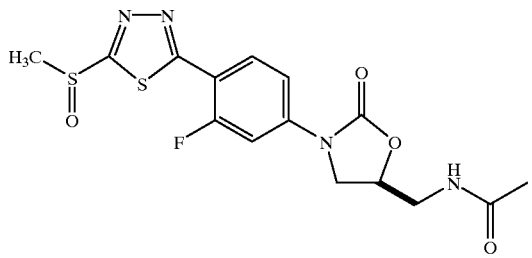

The sulfide prepared in Step 2 of Example 31 (252 mg) is suspended in CH₃OH (5 mL) and water (5 mL). Sodium metaperiodate (155 mg) is added with stirring. The reaction mixture is heated at reflux for 18 hours and then cooled and concentrated. The residue is dissolved in CH₃OH and CH₂Cl₂, absorbed onto silica gel and purified by flash chromatography using 20% CH₃CN in ethyl acetate to 5 % CH₃OH in CH₂Cl₂ as the eluent to afford 104 mg of the title compound.

Physical characteristics are as follows: mp 213–215° C. $^1$H NMR (DMSO-d$_6$) δ 8.31, 7.76, 7.59, 4.77, 4.18, 3.81, 3.42, 3.17, 1.81. Anal. Found: C, 44.87; H, 3.72; N, 13.88; S, 15.61.

EXAMPLE 48

(S)-N-[[3-[3-Fluoro-4-[5-(1-methylethyl)-1,3,4-thiadiazol-2-yl]phenyl]-2-oxo-5-oxazolidinyl] methyl]acetamide. (I-A, X$^1$=F, X$^2$=H, R$^1$=CH$_3$CO, R$^2$=(CH$_3$)$_2$CH). Refer to Scheme I

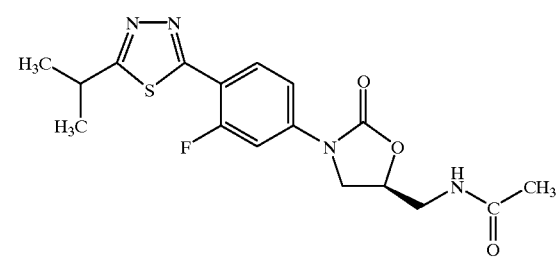

The thiohydrazide XVI prepared in Example 3, Step 4 (300 mg) is reacted with isobutyryl chloride (125 µL) according to the procedure of Step 5, Example 3 to afford 150 mg of the title compound.

Physical characteristics are as follows: mp 158° C. $^1$H NMR (DMSO-d$_6$) δ 8.22, 7.70, 7.52, 4.73, 3.79, 3.79, 3.50, 3.42, 1.82, 1.39. Anal. Found: C, 53.63; H, 5.18; N, 14.81; S, 8.43.

EXAMPLE 49

(S)-N-[[5-[4-[5-[(Acetylamino)methyl]-2-oxo-3-oxazolidinyl]-2-fluorophenyl]-1,3,4-thiadiazol-2-yl]methyl]acetamide. (I-A, $X^1$=F, $X^2$=H, $R^1$=CH$_3$CO, $R^2$=CH$_3$C(O)NHCH$_2$). Refer to Scheme I

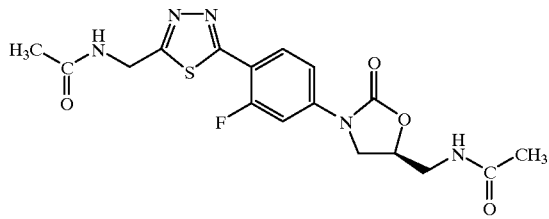

The amine of Example 6, Step 2 (300 mg) is mixed with CH$_2$Cl$_2$ (10 mL) and triethylamine (457 μL). The temperature is lowered to 0° C. and acetyl chloride (117 μL) is added. The reaction is warmed to RT and then concentrated in vacuo. The solid is dissolved in CH$_2$Cl$_2$ and MeOH, absorbed onto silica gel, and flash chromatographed using 6% MeOH in CH$_2$Cl$_2$ as eluent to give 301 mg of the title compound.

Physical characteristics are as follows: mp 233–235° C. $^1$H NMR (DMSO-d$_6$) δ 8.90, 8.25, 7.70, 7.51, 4.77, 4.65, 4.17, 3.81, 3.41, 1.89, 1.82. Anal. Found: C, 49.98; H, 4.45; N, 16.95.

EXAMPLE 50

(S)-N-[[3-[3-Fluoro-4-[5-(3-hydroxypropyl)-1,3,4-thiadiazol-2-yl]phenyl]-2-oxo-5-oxazolidinyl]methyl]acetamide. (I-A, $X^1$=F, $X^2$=H, $R^1$=CH$_3$CO, $R^2$=HOCH$_2$CH$_2$CH$_2$). Refer to Scheme I

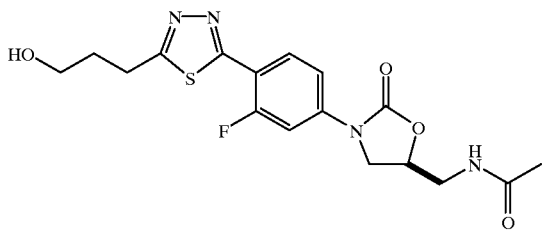

Step 1. 4-[(tert-Butyldiphenylsilyl)oxy]butyryl chloride is prepared as described in *J. Org. Chem*, 1996, 61, 2413–2427.

Step 2. The thiohydrazide XVI prepared in Example 3, Step 4 (352 mg) is reacted with the acid chloride prepared in Step 1 of this example (776 mg) according to the procedure of Example 3, Step 5. The residue is treated with methanol to afford 363 mg of the title compound.

Physical characteristics are as follows: mp 195–197° C. $^1$H NMR (DMSO-d$_6$) δ 8.23, 7.70, 7.51, 4.76, 4.62, 4.16, 3.79, 3.42, 3.16, 1.89, 1.81; Anal. Found: C, 51.33; H, 4.97; N, 14.06; S, 7.42.

EXAMPLE 51

[S-(R*,R*)]-N-[[3-[3-Fluoro-4-[5-(1-hydroxyethyl)-1,3,4-thiadiazol-2-yl]phenyl]-2-oxo-5-oxazolidinyl]methyl]acetamide. (I-A, $X^1$=F, $X^2$=H, $R^1$=CH$_3$CO, $R^2$=S—CH$_3$CH(OH)). Refer to Scheme I

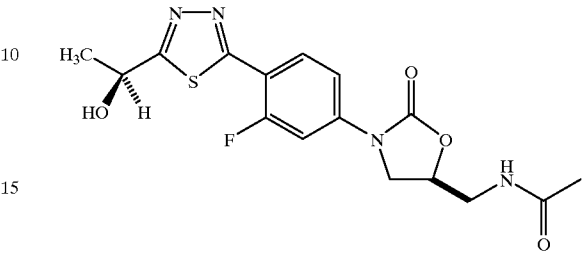

Step 1. The t-butyldimethylsilyl ether of L-lactic acid chloride is prepared as described in *Tetrahedron Letters*, 1996, 37, 3515–3518.

Step 2. The thiohydrazide XVI prepared in Example 3, Step 4 (414 mg) is reacted with the acid chloride prepared in Step 1 of this example (563 mg) according to the procedure of Example 3, Step 5. The residue is treated with methanol to afford 383 mg of the title compound.

Physical characteristics are as follows: mp 202–203° C. $^1$H NMR (DMSO-d$_6$) δ 8.25, 7.70, 7.52, 6.39, 5.15, 4.76, 4.17, 3.79, 3.42, 1.81, 1.53. Anal. Found: C, 50.28; H, 4.44; N, 14.73; S, 8.42.

EXAMPLE 52

[S-(R*,S*)]-N-[[3-[3-Fluoro-4-[5-(1-hydroxyethyl)-1,3,4-thiadiazol-2-yl]phenyl]-2-oxo-5-oxazolidinyl]methyl]acetamide. (I-A, $X^1$=F, $X^2$=H, $R^1$=CH$_3$CO, $R^2$=R—CH$_3$CH(OH)). Refer to Scheme I

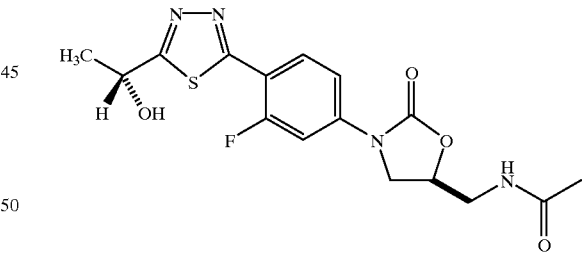

Step 1. The t-butyldimethylsilyl ether of R-lactic acid chloride is prepared as described in *Tetrahedron Letters*, 1996, 37, 3515–3518.

Step 2. The thiohydrazide XVI of Example 3, Step 4 (414 mg) is reacted with the acid chloride prepared in Step 1 of this example (563 mg) according to the procedure of Example 3, Step 5. The residue is treated with methanol to afford 383 mg of the title compound.

Physical characteristics are as follows: mp 209–210° C.; $^1$H NMR (DMSO-d$_6$) δ 8.23, 7.70, 7.51, 6.41, 5.15, 4.76, 4.17, 3.79, 3.42, 1.81, 1.50; Anal. Found: C, 50.32; H, 4.66; N, 14.56; S, 8.27.

EXAMPLE 53

(S)-N-[[3-[3-Fluoro-4-[5-(2-nitroethyl)-1,3,4-thiadiazol-2-yl]phenyl]-2-oxo-5-oxazolidinyl]methyl]acetamide. (I-A, X$^1$=F, X$^2$H, R$^1$=CH$_3$CO, R$^2$=O$_2$NCH$_2$CH$_2$). Refer to Scheme I

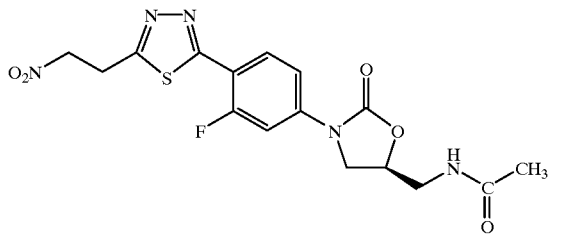

Step 1. 3-Nitropropionyl chloride is prepared according to the procedure of *J. Pharm. Sci.* 1978, 67,421–3.

Step 2. The thiohydrazide XVI of Example 3, Step 4 (300 mg) is reacted with the acid chloride prepared in Step 1 of this example (164 mg) according to the procedure of Example 3, Step 5.

Physical characteristics are as follows: mp 195–197° C. $^1$H NMR (DMSO-d$_6$) δ 8.23, 7.71, 7.53, 5.09, 4.76, 4.17, 3.81, 3.42, 1.82. Anal. Found: C, 46.87; H, 4.19; N, 16.79; S, 7.70.

EXAMPLE 54

(S)-N-[[3-[3-Fluoro-4-[5-(3-nitropropyl)-1,3,4-thiadiazol-2-yl]phenyl]-2-oxo-5-oxazolidinyl]methyl]acetamide. (I-A, X$^1$=F, X$^2$=H, R$^1$=CH$_3$CO, R$^2$=O$_2$NCH$_2$CH$_2$CH$_2$). Refer to Scheme I

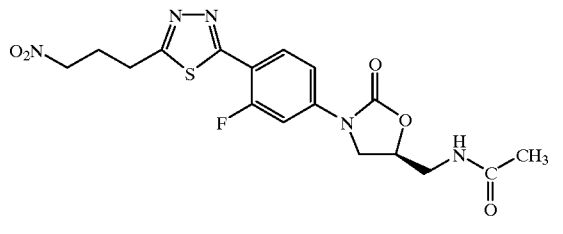

Step 1. 4-Nitrobutyryl chloride is prepared according to the procedure of *Chem Pharm. Bull.* 1992, 40, 2338–2343.

Step 2. The thiohydrazide XVI of Example 3, step 4 (1.44 g) is reacted with the acid chloride prepared in Step 1 of this example (868 mg) according to the procedure of Example 3, Step 5.

Physical characteristics are as follows: mp 183–185° C. $^1$H NMR (DMSO-d$_6$) δ 8.26, 7.71, 7.53, 4.76, 4.69, 4.17, 3.80, 3.42, 3.24, 2.40, 1.82. Anal. Found: C, 48.50; H, 4.44; N, 16.10; S, 7.45.

EXAMPLE 55

[S-(R*,R*)]-N-[[3-[4-[5-(1-Aminoethyl)-1,3,4-thiadiazol-2-yl]-3-fluorophenyl]-2-oxo-5-oxazolidinyl]methyl]acetamide. (I-A, X$^1$=F, X$^2$=H, R$^1$=CH$_3$CO, R$^2$=S—CH$_3$CHNH$_2$). Refer to Scheme I

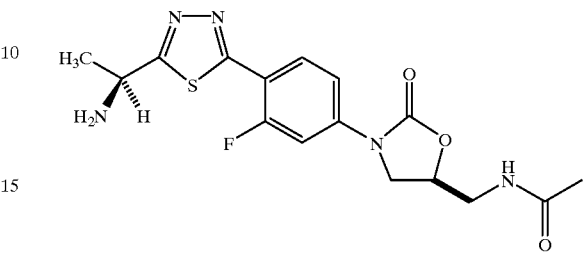

Step 1. The thiohydrazide XVI of Example 3, Step 4 (383 mg) is reacted with FMOC-Ala-Cl (503 mg) according to the procedure of Example 3, Step 5 to afford a protected aminoethyl thiadiazole.

Step 2. The protected thiadiazole prepared in step 1 (355 mg) is stirred in piperidine (8.4 mL) at room temperature for 1 hour and then concentrated. The residue is triturated with ether and the solid is isolated by filtration and dried. The solid is dissolved in methanol/CH$_2$Cl$_2$, absorbed onto silica gel and purified by flash chromatography using 7% methanol in CH$_2$Cl$_2$ as the eluent to afford 211 mg of the title compound.

Physical characteristics are as follows: mp 184–186° C. $^1$H NMR (DMSO-d$_6$) δ 8.24, 7.70, 7.50, 4.76, 4.40, 4.17, 3.78, 3.42, 2.57, 1.81, 1.44. Anal. Found: C, 49.49; H, 5.10; N, 17.93; S, 8.11.

EXAMPLE 56

[S-(R*,S*)]-N-[[3-[4-[5-(1-Aminoethyl)-1,3,4-thiadiazol-2-yl]-3-fluorophenyl]-2-oxo-5-oxazolidinyl]methyl]acetamide. (I-A, X$^1$=F, X$^2$ H, R$^1$=CH$_3$CO, R$^2$=R—CH$_3$CHNH$_2$). Refer to Scheme I

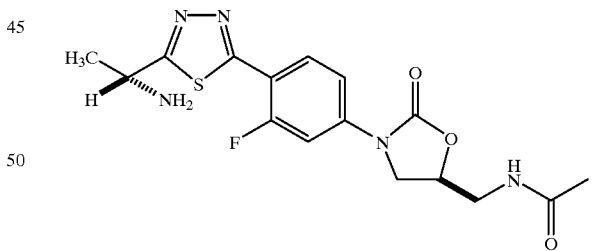

Step 1. The thiohydrazide XVI of Example 3, Step 4 (359 mg) is reacted with FMOC-D-Ala-Cl (472 μL) according to the procedure of Example 3, Step 5 to afford a protected aminoethyl thiadiazole.

Step 2. A suspension of the thiadiazole prepared in Step 1 of this example (390 mg) in piperidine (9 mL) is stirred at room temperature for 1 hour and then concentrated. The residue is triturated with ether and the solid is isolated by filtration and dried. The solid is dissolved in methanol/CH$_2$Cl$_2$, absorbed onto silica gel and purified by flash chromatography using 7% methanol in CH$_2$Cl$_2$ as the eluent to afford 229 mg of the title compound.

Physical characteristics are as follows: mp 201–203° C. ¹H NMR (DMSO-d₆) δ 8.24, 7.70, 7.51, 4.76, 4.40, 4.16, 3.79, 3.42, 3.33, 2.63, 1.81, 1.44. Anal. Found: C, 49.27; H, 5.03; N, 17.90; S, 8.07.

EXAMPLE 57

(S)-N-[[3-[4-[5-(3-Aminopropyl)-1,3,4-thiadiazol-2-yl]-3-fluorophenyl]-2-oxo-5-oxazolidinyl]methyl]acetamide. (I-A, $X^1$=F, $X^2$=H, $R^1$=CH₃CO, $R^2$= H₂NCH₂CH₂CH₂). Refer to Scheme I

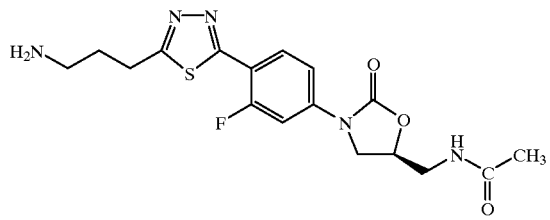

The 3-nitropropylthiadiazole prepared in Example 54, Step 2 (400 mg) is dissolved in MeOH (100 mL) and DMF (25 mL). Raney Nickel (approx. 1.0 g) is added and the reaction is placed on a Parr apparatus under H₂ (45 psi) overnight. The reaction is filtered and concentrated. The residue is taken up in CHCl₃ and MeOH, absorbed onto silica gel, and purified by flash chromatography using 1.5% MeOH (saturated with NH₃) in CH₂Cl₂ as eluent to afford 193 mg of the title compound.

Physical characteristics are as follows: mp 181–183° C. ¹H NMR (DMSO-d₆) δ 8.23, 7.70, 7.52, 4.77, 4.16, 3.81, 3.42, 3.17, 2.61, 1.82. Anal. Found: C, 51.36; H, 5.04; N, 17.23; S, 7.85.

EXAMPLE 58

(S)-N-[3-[5-[4-[5-[(Acetylamino)methyl]-2-oxo-3-oxazolidinyl]-2-fluorophenyl]-1,3,4-thiadiazol-2-yl]propyl]acetamide. (I-A, $X^1$=F, $X^2$=H, $R^1$=CH₃CO, $R^2$=CH₃C(O)NHCH₂CH₂CH₂). Refer to Scheme I

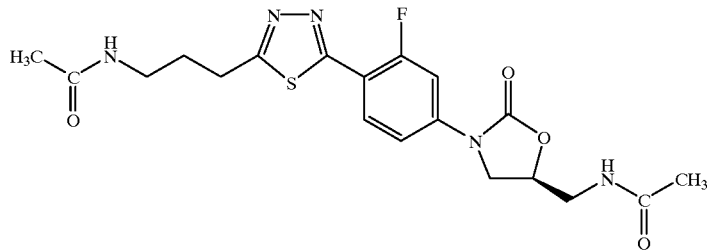

The 3-aminopropylthiadiazole prepared in Example 57 (300 mg) is dissolved in CH₂Cl₂ (20 mL) at room temperature under nitrogen. Acetic anhydride (90 μL) and pyridine (185 μL) are added, and the reaction is heated to reflux for 1 hour. The reaction is then cooled and concentrated. The residue is dissolved in MeOH and CH₂Cl₂, absorbed onto silica gel, and purified by flash chromatography using 3% MeOH (saturated with NH₃) in CH₂Cl₂ as eluent to give 287 mg of the title compound.

Physical characteristics follow: mp 229–230° C. ¹H NMR (DMSO-d₆) δ 8.23, 7.93, 7.71, 7.53, 4.77, 4.17, 3.82, 3.42, 3.13, 1.88, 1.82, 1.79. Anal. Found: C, 52.04; H, 5.10; N, 15.89; S, 7.27.

EXAMPLE 59

(S)-N-[[3-[4-(5-Acetyl-1,3,4-thiadiazol-2-yl)-3-fluorophenyl]-2-oxo-5-oxazolidinyl]methyl]acetamide. (I-A, $X^1$=F, $X^2$=H, $R^1$=CH₃CO, $R^2$= CH₃CO). Refer to Scheme I

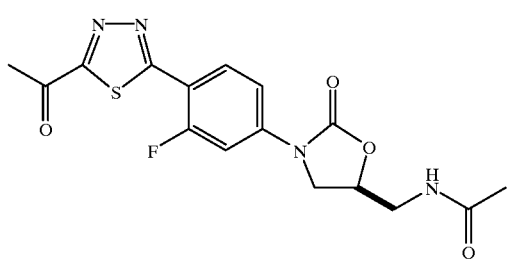

Step 1. Pyruvyl chloride is prepared as described in *Synthesis*, 1975, 163–164.

Step 2. The thiohydrazide XVI of Example 3, Step 4 (959 mg) is reacted with the acid chloride prepared in Step 1 of this example (655 mg) according to the procedure of Example 3, Step 5 to give 442 mg of the title compound.

Physical characteristics are as follows: mp 242–244° C. ¹H NMR (DMSO-d₆) δ 8.35, 8.27, 7.75, 7.56, 4.78, 4.18, 3.81, 3.43, 2.74, 1.81. Anal. Found: C, 50.43; H, 4.03; N, 14.75; S, 8.35.

EXAMPLE 60

(S)-N-[[3-[4-[5-(3-Chloropropyl)-1,3,4-thiadiazol-2-yl]-3-fluorophenyl]-2-oxo-5-oxazolidinyl]methyl]acetamide. (I-A, $X^1$=F, $X^2$=H, $R^1$=$CH_3CO$, $R^2$= $ClCH_2CH_2CH_2$). Refer to Scheme I

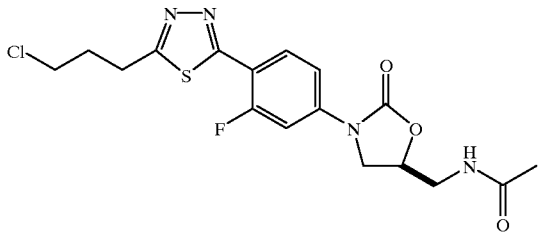

The thiohydrazide XVI of Example 3, Step 4 (322 mg) is reacted with 4-chlorobutyryl chloride (140 μL) according to the procedure of Example 3, Step 5 to give the title compound (306 mg).

Physical characteristics are as follows: mp 199–200° C. $^1$H NMR (DMSO-$d_6$) δ 8.23, 7.73, 7.52, 4.77, 4.17, 3.79, 3.74, 3.42, 3.29, 2.27, 1.8. Anal. Found: C, 49.08; H, 4.50; N, 13.45; Cl, 8.52; S, 7.62.

EXAMPLE 61

(S)-N-[[3-[4-[5-(3-Cyanopropyl)-1,3,4-thiadiazol-2-yl]-3-fluorophenyl]-2-oxo-5-oxazolidinyl]methyl]acetamide. (I-A, $X^1$=F, $X^2$=H, $R^1$=$CH_3CO$, $R^2$= $NCCH_2CH_2CH_2$). Refer to Scheme I

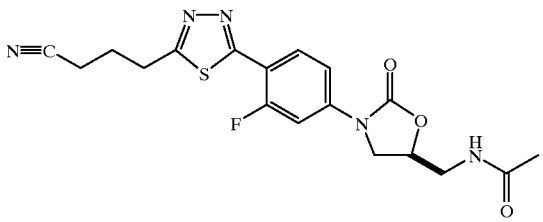

A mixture of the chloride prepared in Example 60 (145 mg) and tetrabutylammonium cyanide (189 mg) in dry DMF (3.5 mL) is heated at 80° C. for 30 minutes. The DMF is removed under vacuum and the residue is dissolved in methanol/$CH_2Cl_2$. The solid that forms is isolated by filtration and dried to afford 81 mg of the title compound.

Physical characteristics are as follows: mp 186–187° C. $^1$H NMR (DMSO-$d_6$) δ 8.24, 7.73, 7.55, 4.77, 4.17, 3.79, 3.42, 3.24, 2.63, 2.08, 1.81. Anal. Found: C, 51.05; H, 4.74; N, 16.47; S, 7.59.

EXAMPLE 62

(S)-N-[[3-[3-Fluoro-4-[5-(methylsulfonyl)-1,3,4-thiadiazol-2-yl]phenyl]-2-oxo-5-oxazolidinyl]methyl]acetamide. (I-A, $X^1$=F, $X^2$=H, $R^1$=$CH_3CO$, $R^2$=$CH_3SO_2$). Refer to Scheme I

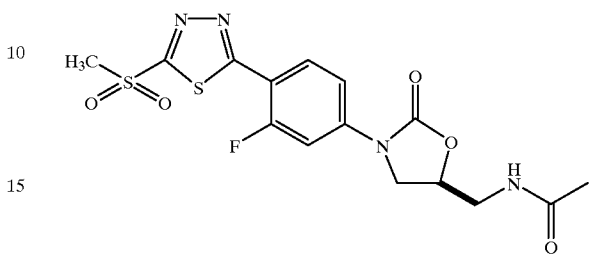

The sulfide prepared in Example 31, Step 2 (206 mg) is dissolved in methanol (2 mL) and water (2 mL). Oxone (431 mg) is added and the reaction mixture is heated at reflux for 4 hours. The reaction mixture is cooled and the solid is separated by filtration and then washed with water. The solid is dissolved in methanol/$CH_2Cl_2$, absorbed onto silica gel and purified by flash chromatography using 6% methanol in $CH_2Cl_2$ as the eluent to afford 166 mg of the title compound.

Physical characteristics are as follows: mp 244–245° C. $^1$H NMR (DMSO-$d_6$) δ 8.36, 8.24, 7.80, 7.62, 4.78, 4.19, 3.81, 3.65, 3.43, 1.81. Anal. Found: C, 43.08; H, 3.90; N, 13.28; S, 14.92.

EXAMPLE 63

(S)-N-[[3-[3-Fluoro-4-[5-[3-(hydroxyimino)butyl]-1,3,4-thiadiazol-2-yl]phenyl]-2-oxo-5-oxazolidinyl]methyl]acetamide. (I-A, $X^1$=F, $X^2$=H, $R^1$=$CH_3CO$, $R^2$=$CH_3C(NOH)CH_2CH_2$). Refer to Scheme I

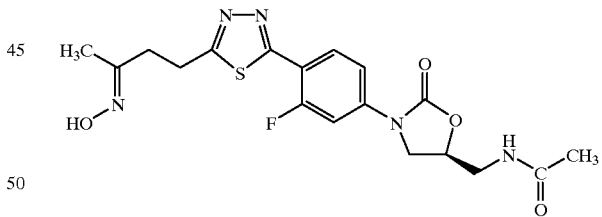

The ketone prepared in Example 16, Step 2 (330 mg) is dissolved in EtOH (20 mL) and $CH_2Cl_2$ (15 mL). Hydroxylamine hydrochloride (169 mg) is added and the reaction is heated to 60° C. overnight under a nitrogen atmosphere. The reaction is then concentrated and the residue is dissolved in MeOH and $CH_2Cl_2$, absorbed onto silica, and purified by flash chromatography using 3% MeOH in $CH_2Cl_2$ as eluent to afford 304 mg of the title compound.

Physical characteristics are as follows: mp 218–220° C. $^1$H NMR (DMSO-$d_6$) δ 8.23, 7.70, 7.50, 4.76, 4.17, 3.79, 3.42, 3.29, 2.64, 1.82, 1.78. Anal. Found: C, 50.58; H, 4.78; N, 16.36; S, 8.07.

EXAMPLE 64

(S)-N-[[3-[3-Fluoro-4-[5-[2-(hydroxyimino)ethyl]-1,3,4-thiadiazol-2-yl]phenyl]-2-oxo-5-oxazolidinyl]methyl]acetamide. (I-A, $X^1$=F, $X^2$=H, $R^1$=$CH_3CO$, $R^2$=HC(NOH)$CH_2$). Refer to Scheme I

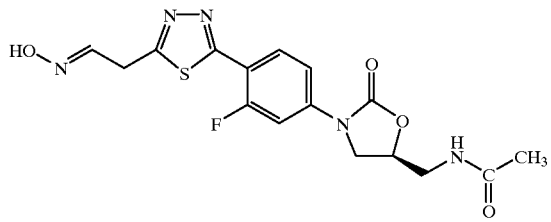

A mixture of stannous chloride (407 mg), thiophenol (462 mg), and triethylamine (0.98 mL) is prepared in $CH_3CN$ (5 mL) at room temperature. The nitroethyl thiadiazole prepared in Example 53, Step 2 (585 mg) is added to this mixture as a solution in 5 mL of 1:1 MeOH and $CH_2Cl_2$. The reaction is stirred for 2 hours and then concentrated to dryness. The residue is absorbed onto silica gel purified by flash chromatography using 5% MeOH in $CH_2Cl_2$ as eluent to afford 205 mg of the title compound.

Physical characteristics are as follows: mp 228–230° C. $^1$H NMR (DMSO-$d_6$) δ 8.25, 7.70, 7.55, 7.08, 4.80, 4.16, 3.79, 3.42, 1.81. Anal. Found: C, 48.51; H, 4.17; N, 17.39; S, 7.88.

EXAMPLE 65

(S)-N-[[3-[3-Fluoro-4-[5-[3-(methoxyimino)butyl]-1,3,4-thiadiazol-2-yl]phenyl]-2-oxo-5-oxazolidinyl]methyl]acetamide. (I-A, $X^1$=F, $X^2$=H, $R^1$=$CH_3CO$, $R^2$=$CH_3$C(N$OCH_3$)$CH_2CH_2$). Refer to Scheme I

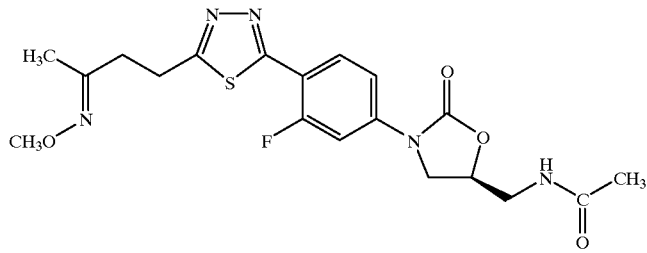

The ketone prepared in Example 16, Step 2 (200 mg) is dissolved in MeOH (2 mL) and $H_2O$ (6 mL). To this solution is added methoxylamine hydrochloride (45 mg), $Na_2CO_3$ (28 mg), and one drop of acetic acid. The reaction is heated at 100° C. for 2 hours. The reaction is cooled and the solids are removed by filtration. The filtrate is flash chromatographed using 5% MeOH in $CH_2Cl_2$ as eluent to afford 104 mg of the title compound.

Physical characteristics are as follows: mp 220–221° C. $^1$H NMR (DMSO-$d_6$) δ 8.26, 7.73, 7.55, 4.78, 4.19, 3.80, 3.73, 3.44, 3.33, 2.67, 1.85, 1.83. Anal. Found: C, 52.13; H, 5.03; N, 15.78; S, 7.20.

EXAMPLE 66

(S)-N-[[5-[4-[5-[(Acetyloxyacetylamino)methyl]-2-oxo-3-oxazolidinyl]-2-fluorophenyl]-1,3,4-thiadiazol-2-yl]methyl]acetamide. (I-A, $X^1$=F, $X^2$=H, $R^1$=$CH_3CO$, $R^2$=$CH_3CO_2CH_2$C(O)NH$CH_2$). Refer to Scheme I

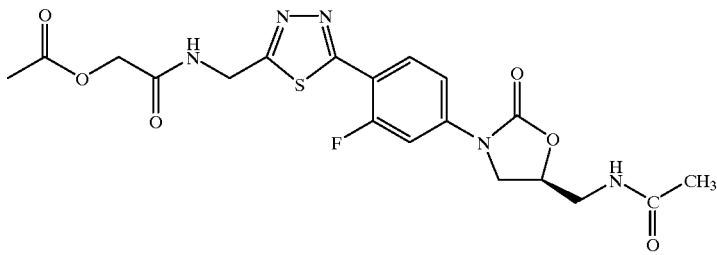

The amine prepared in Example 6, Step 2 (605 mg) is dissolved in $CH_2Cl_2$ (25 mL). To this solution is added acetoxyacetylchloride (348 μL) and pyridine (541 μL). The reaction is heated at reflux for 1 hour. The solvent is removed and the residue is absorbed onto silica gel and purified by flash chromatography using 5% MeOH in $CH_2Cl_2$ as eluent to afford 445 mg of the title compound.

Physical characteristics are as follows: mp 210–21 1° C. $^1$H NMR (DMSO-$d_6$) δ 9.00, 8.27, 7.74, 7.55, 4.75, 4.54, 4.20, 3.82, 3.44, 2.11, 1.84. Anal. Found: C, 48.41; H, 4.24; N, 14.63; S, 6.58.

EXAMPLE 67

(S)-N-[[5-[4-[5-[(Hydroxyacetylamino)methyl]-2-oxo-3-oxazolidinyl]-2-fluorophenyl]-1,3,4-thiadiazol-2-yl]methyl]acetamide. (I-A, $X^1$=F, $X^2$=H, $R^1$=$CH_3CO$, $R^2$=$HOCH_2C(O)NHCH_2$). Refer to Scheme I

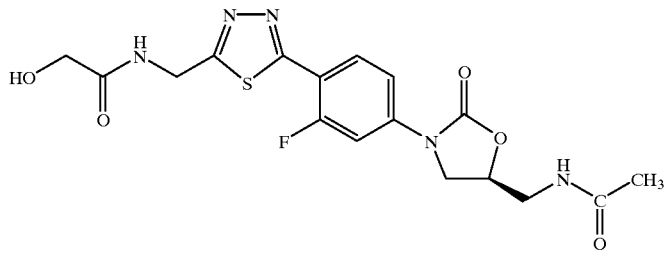

The thiadiazole prepared in Example 66 (250 mg) is suspended in MeOH (8 mL) at room temperature and $K_2CO_3$ (104 mg) is added. The reaction is stirred at room temperature for 30 minutes and then diluted with $CH_2Cl_2$ until homogeneous. The solids are removed by filtration and the reaction is concentrated. The residue is dissolved in MeOH and $CH_2Cl_2$, absorbed onto silica gel and purified by flash chromatography using 8% MeOH in $CH_2Cl_2$ as eluent to afford 108 mg of the title compound.

Physical characteristics are as follows: mp 202–5° C. $^1H$ NMR (DMSO-$d_6$) δ 8.80, 8.26, 7.73, 7.55, 5.26, 4.76, 4.19, 3.89, 3.82, 3.44, 1.84. Anal. Found: C, 47.76; H, 4.39; N, 15.97; S, 7.28.

EXAMPLE 68

(S)-N-[5-[4-[5-[(Acetylamino)methyl]-2-oxo-3-oxazolidinyl]-2-fluorophenyl]-1,3,4-thiadiazol-2-yl]-2-(acetyloxy)acetamide. (I-A, $X^1$=F, $X^2$=H, $R^1$=$CH_3CO$, $R^2$=$CH_3CO_2CH_2C(O)NH$). Refer to Scheme I

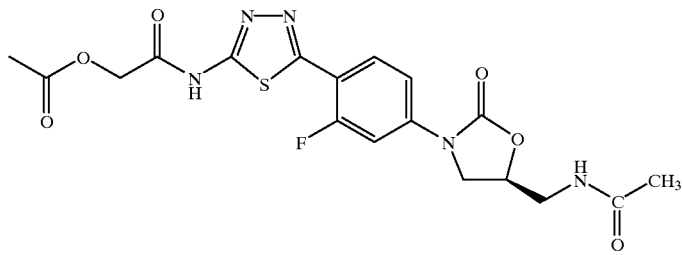

The aminothiadiazole prepared in Example 30 (100 mg) is dissolved in pyridine (5 mL) and chilled in an ice bath. Acetoxyacetyl chloride (184 mL) is added and the ice bath is removed. The reaction is stirred for 30 minutes and then concentrated in vacuo. The residue is dissolved in MeOH/$CH_2Cl_2$, absorbed onto silica gel, and flash chromatographed using 4% MeOH in $CH_2Cl_2$ as eluent to afford 89 mg of the title compound.

Physical characteristics are as follows: mp 245–246° C. $^1H$ NMR (DMSO-$d_6$) δ 13.0, 8.26, 7.71, 7.55, 4.85, 4.78, 4.19, 3.82, 3.44, 2.14, 1.84. Anal. Found: C, 47.66; H, 4.14; N, 14.94; S, 6.74.

EXAMPLE 69

(S)-N-[[3-[3-Fluoro-4-[5-[(methylsulfonyl)methyl]-1,3,4-thiadiazol-2-yl]phenyl]-2-oxo-5-oxazolidinyl]methyl]acetamide. (I-A, $X^1$=F, $X^2$=H, $R^1$=$CH_3CO$, $R^2$=$CH_3SO_2CH_2$). Refer to Scheme I

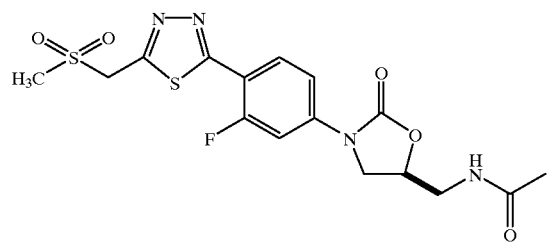

The sulfide prepared in Example 21, Step 2 (177 mg) is suspended in 1:1 methanol/water (4.0 mL) and oxone (359 mg) is added. The reaction mixture is heated at reflux for 2 hours and then cooled. The solid is isolated by filtration, washed with water and dried. The solid is dissolved in THF/acetone, absorbed onto silica gel and purified by flash chromatography using 5 % MeOH in $CH_2Cl_2$ as the eluent to afford 136 mg of the title compound.

Physical characteristics are as follows: mp 216–217° C. $^1H$ NMR (DMSO-$d_6$) δ 8.32, 8.25, 7.74, 7.59, 5.32, 4.79, 4.20, 3.83, 3.45, 3.16, 1.84. Anal. Found: C, 44.68; H, 4.06; N, 12.95; S, 14.65.

EXAMPLE 70

(S)-N-[[3-[3-Fluoro-4-[5-[2-(methylsulfonyl)ethyl]-1,3,4-thiadiazol-2-yl]phenyl]-2-oxo-5-oxazolidinyl]methyl]acetamide. (I-A, $X^1$=F, $X^2$=H, $R^1$=$CH_3CO$, $R^2$=$CH_3SO_2CH_2CH_2$). Refer to Scheme I

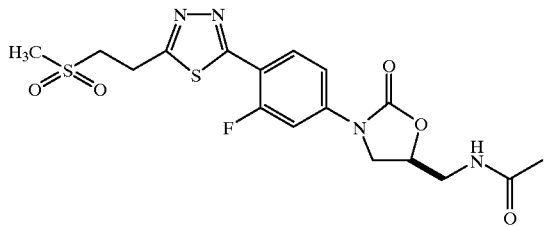

The sulfide prepared in Example 23, Step 2 (303 mg) is suspended in 1:1 methanol/water (8.0 mL). Oxone (590 mg) is added and the reaction mixture is heated at reflux for 3 hours and then cooled. The solid is isolated by filtration, washed with water and dried. The solid is dissolved in THF/acetone, absorbed onto silica gel and purified by flash chromatography using 5 % MeOH in $CH_2Cl_2$ as the eluent to afford 213 mg of the title compound.

Physical characteristics are as follows: mp 217–218° C. $^1$H NMR (DMSO-$d_6$) δ 8.26, 7.76, 7.56, 4.78, 4.19, 3.81, 3.69, 3.63, 3.44, 3.08, 1.83. Anal. Found: C, 45.61; H, 4.41; N, 12.52; S, 14.32.

EXAMPLE 71

(S)-N-[[3-[3-Fluoro-4-(1,3,4-thiadiazol-2-yl)phenyl]-2-oxo-5-oxazolidinyl]methyl]propanamide. (I-A, $X^1$=F, $X^2$=H, $R^1$=$CH_3CH_2CO$, $R^2$=H). Refer to Scheme I

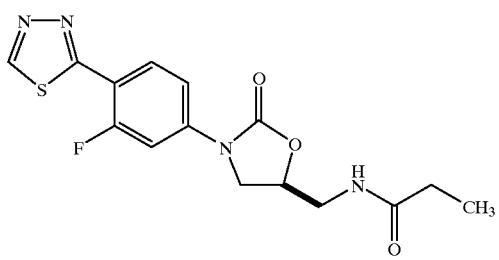

Step 1. The thiadiazole prepared in Example 9 (1.65 g) is dissolved in MeOH (130 mL) and 6M HCl (42 mL) is added. The reaction is heated at reflux for 24 hours and then cooled and diluted with ether (20 mL). The precipitate is filtered, washed with ether and dried to afford 1.60 g of the aminomethyl oxazolidinone as an HCl salt.

Step 2. The aminomethyl oxazolidinone prepared in Step 1 (249 mg) is dissolved in THF (10 mL) and saturated, aqueous $Na_2CO_3$ (10 mL) is added. The solution is chilled in an ice bath and propionyl chloride (98 μL) is added. The ice bath is removed, and the reaction is stirred for 1 hour. The liquid phases are separated and the aqueous phase is extracted with $CH_2Cl_2$. The combined organic phases are diluted with MeOH (10 mL) in order to dissolve the suspended solids. This organic solution is dried with $MgSO_4$, filtered, and concentrated. The residue is triturated with t-butyl methyl ether and a few drops of MeOH to afford a solid which is filtered and dried to give 234 mg of the title compound.

Physical characteristics are as follows: mp 232–234° C. $^1$H NMR (DMSO-$d_6$) δ 9.70, 8.31, 8.17, 7.73, 7.54, 4.79, 4.18, 3.82, 3.44, 2.08, 0.93. Anal. Found: C, 50.77; H, 4.27; N, 15.75; S, 9.15.

EXAMPLE 72

(S)-N-[[3-[3-Fluoro-4-[5-(2-methoxyethyl)-1,3,4-thiadiazol-2-yl]phenyl]-2-oxo-5-oxazolidinyl]methyl]propanamide. (I-A, $X^1$=F, $X^2$=H, $R^1$=$CH_3CH_2CO$, $R^2$=$CH_3OCH_2CH_2$). Refer to Scheme I

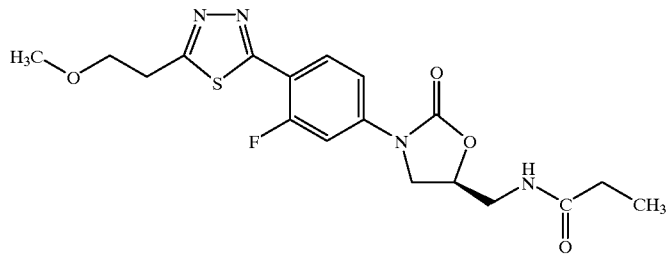

Step 1. The 2-chloroethyl thiadiazole prepared in Example 42 (760 mg) is dissolved in MeOH (60 mL) and 6M HCl (22 mL) is added. This solution is refluxed for 24 hours and then cooled and diluted with ether (20 mL). The precipitate is filtered, washed with ether and dried to afford 800 mg of the 2-methoxyethyl thiadiazole intermediate amine as an HCl salt.

Step 2. The amine salt prepared in step 1 (700 mg) is dissolved in a mixture of 15 mL of THF and 15 mL of saturated, aqueous $Na_2CO_3$ at 0° C. Propionyl chloride (170 μL) is added and the reaction mixture is stirred at room temperature for 3 hours. The reaction is concentrated and the residue is dissolved in MeOH and $CH_2Cl_2$ and absorbed onto silica gel. The product is purified by flash chromatography using 2.5% MeOH (saturated with $NH_3$) in $CH_2Cl_2$ as eluent to afford 175 mg of the title compound.

Physical characteristics are as follows: mp 189–190° C. $^1$H NMR (DMSO-$d_6$) δ 8.24, 8.16, 7.70, 7.52, 4.78, 4.16, 3.81, 3.69, 3.44, 3.37, 3.29, 2.08, 0.93. Anal. Found: C, 52.78; H, 5.21; N, 13.65; S, 7.78.

EXAMPLE 73

(S)-N-[[3-[3-Fluoro-4-[5-(2-methoxyethyl)-1,3,4-thiadiazol-2-yl]phenyl]-2-oxo-5-oxazolidinyl]methyl]acetamide. (I-A, $X^1$=F, $X^2$=H, $R^1$=$CH_3CO$, $R^2$=$CH_3OCH_2CH_2$). Refer to Scheme I

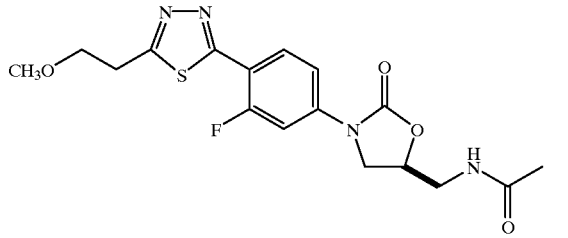

The amine salt prepared in Step 1 of Example 72 (150 mg) is dissolved in a mixture of THF (5 mL) and saturated, aqueous $Na_2CO_3$ (5 mL) at 0° C. To this solution is added acetyl chloride (30 μL), the reaction is allowed to warm to room temperature, and stirred for one hour. The reaction is diluted with water (5 mL) and extracted with $CH_2Cl_2$. The organic phases are combined, dried over MgSO, filtered, and concentrated to give 142 mg of the title compound.

Physical characteristics are as follows: mp 187–18° C. $^1$H NMR (DMSO-$d_6$) δ 8.26, 7.73, 7.53, 4.78, 4.20, 3.85, 3.71, 3.45, 3.40, 3.31, 1.84. Anal. Found: C, 51.43; H, 4.97; N, 13.95; S, 8.03.

EXAMPLE 74

(S)-N-[[3-[3-Fluoro-4-(1,3,4-thiadiazol-2-yl)phenyl]-2-oxo-5-oxazolidinyl]methyl]ethanethioamide. (I-A, $X^1$=F, $X^2$=H, $R^1$=$CH_3CS$, $R^2$=H). Refer to Scheme I

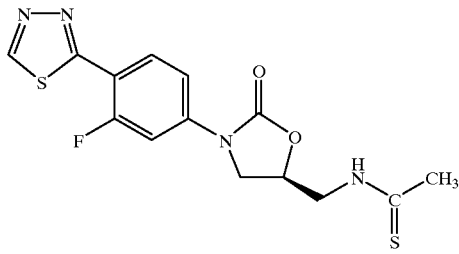

The amine hydrochloride salt prepared in Step 1 of Example 71 (300 mg) is dissolved in THF (10 mL). Triethylamine (507 μL) and ethyldithioacetate (210 μL) are added to the solution. The reaction mixture is stirred at room temperature for 1.5 hours and then concentrated to dryness. The residue is taken up in $CH_2Cl_2$ and washed with 10% $KHSO_4$ solution, $H_2O$, and brine. The aqueous portions are back washed with $CH_2Cl_2$. The combined organic layers are dried over $MgSO_4$, filtered and absorbed onto silica for purification by flash chromatography using 2.5% MeOH in $CH_2Cl_2$ as eluent to give 175 mg of the title compound.

Physical characteristics are as follows: mp 195–196° C. $^1$H NMR (DMSO-$d_6$) δ 10.4, 9.7, 8.31, 7.74, 7.56, 5.00, 4.23, 3.90, 2.43. Anal. Found: C, 47.53; H, 3.89; N, 15.70; S, 18.08.

EXAMPLE 75

(S)-[[3-[3-Fluoro-4-(1,3,4-thiadiazol-2-yl)phenyl]-2-oxo-5-oxazolidinyl]methyl]thiourea. (I-A, $X^1$=F, $X^2$=H, $R^1$=$H_2NCS$, $R^2$=H). Refer to Scheme I

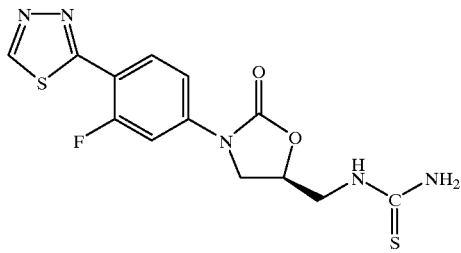

Step 1. The amine hydrochloride salt prepared in Step 1 of Example 71 (500 mg) is dissolved in 60 mL of $CH_2Cl_2$. This solution is added at 0° C. to a stirred solution of 1,1'-thiocarbonyl-di-2-(1H)-pyridone (422 mg) in $CH_2Cl_2$ (18 mL). The reaction is warmed to room temperature and stirred overnight. Triethylamine (315 μL) is added and the reaction is stirred for an additional hour. The reaction is then washed with $H_2O$ and brine and dried over $Na_2SO_4$, filtered and concentrated. The residue is absorbed onto silica and purified by flash chromatography using 20% $CH_3CN$ in $CH_2Cl_2$ as eluent to give 250 mg of an isothiocyanate which is used immediately in the next reaction.

Step 2. The isothiocyanate (240 mg) prepared in Step 1 is dissolved in THF (20 mL) and the resulting solution cooled to 0° C. Ammonia gas is bubbled into the reaction for 6 minutes. The reaction is capped and allowed to stand for 45 minutes. The reaction is then concentrated and triturated with $Et_2O$ and a few drops of MeOH to give 230 mg of the title compound.

Physical characteristics are as follows: mp 215–217° C. $^1$H NMR (DMSO-$d_6$) δ 9.85, 8.31, 7.93, 7.74, 7.55, 7.20, 4.90, 4.20, 3.85. Anal. Found: C, 43.91; H, 3.59; N, 19.40; S, 17.92.

EXAMPLE 76

(S)-N-[[3-[3-Fluoro-4-(1,3,4-thiadiazol-2-yl)phenyl]-2-oxo-5-oxazolidinyl]methyl]propanethioamide. (I-A, $X^1$=F, $X^2$=H, $R^1$=$CH_3CH_2CS$, $R^2$=H). Refer to Scheme I

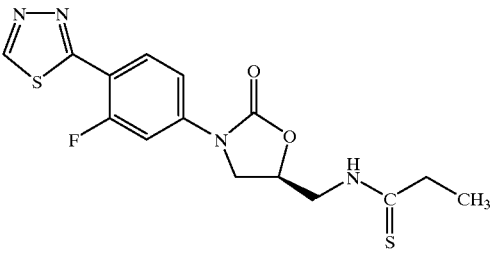

The thiadiazole propionamide prepared in Example 71, Step 2 (238 mg) is dissolved in 1,4-dioxane (7 mL) and Lawesson's reagent (286 mg) is added to this solution. The reaction is heated at 100° C. for 18 hours. The dioxane is removed in vacuo and the residue is dissolved in MeOH and $CH_2Cl_2$, absorbed onto silica gel, and purified by flash chromatography using 5% MeOH in $CH_2Cl_2$ as eluent to give 225 mg of the title compound.

Physical characteristics are as follows: mp 179–181° C.
$^1$H NMR (DMSO-d$_6$) δ 10.3, 9.80, 8.31, 7.73, 7.55, 5.02, 4.23, 3.92, 2.58, 1.13. Anal. Found: C, 48.94; H, 4.36; N, 14.84; S, 17.21.

EXAMPLE 77

N-[((5S)-3-{4-[5-(aminomethyl)-1,3,4-thiadiazol-2-yl]-3-fluorophenyl}-2-oxo-1,3-oxazolidin-5-yl)methyl]ethanethioamide. (I-A, X$^1$=F, X$^2$=H, R$^1$=CH$_3$CS, R2 =H$_2$NCH$_2$). Refer to Scheme I

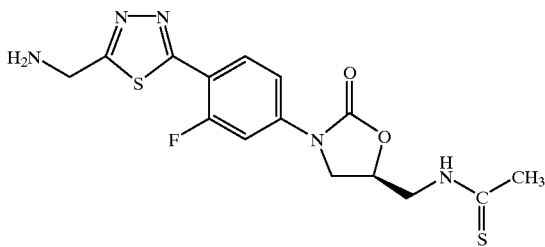

Step 1. The FMOC-protected amine prepared in Example 6, Step 1 (3.0 g) is dissolved in 60 mL of p-dioxane at room temperature. Lawesson's reagent (2.13 g) is added and the reaction is heated at 100° C. for 2 hours. The reaction is cooled to room temperature and diluted with Et$_2$O. The resulting precipitate is triturated with MeOH to give 2.6 g of the thioamide.

Step 2. The thioamide prepared in Step 1 (2.4 g) is stirred in 41 mL of piperidine at room temperature for 30 minutes. The reaction mixture is then concentrated. Purification by flash chromatography using 10% MeOH in CH$_2$Cl$_2$ as eluent gives 1.17 g of the title compound.

Physical characteristics are as follows: mp 205–206° C.
$^1$H NMR (DMSO-d6) δ 10.35, 8.25, 7.73, 7.55, 5.00, 4.24, 4.16, 3.90, 2.58, 2.50. Anal. Found: C, 47.12; H, 4.26; N, 18.16; S, 16.48.

EXAMPLE 78

2-({[5-(4-{(5S)-5-[(ethanethioylamino)methyl]-2-oxo-1,3-oxazolidin-3-yl}-2-fluorophenyl)-1,3,4-thiadiazol-2-yl]methyl}amino)-2-oxoethyl acetate. (I-A, X$^1$=F, X$^2$=H, R$^1$=CH$_3$CS, R2= CH$_3$CO$_2$CH$_2$CONHCH$_2$). Refer to Scheme I

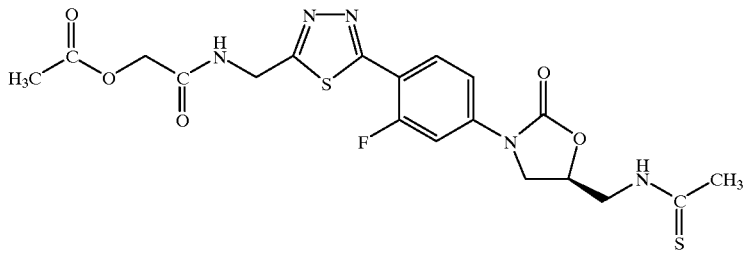

The amine prepared in Example 77, Step 2 (850 mg) is stirred in 35 mL of CH$_2$Cl$_2$. To this is added acetoxyacetylchloride (480 μL) and pyridine (730 μL). The reaction is heated to reflux for 1 hour. The reaction is cooled to room temperature and concentrated. Purification by flash chromatography using 1% NH$_4$OH, 10% isopropanol, and 89% CHCl$_3$ as eluent results in partial hydrolysis of the acetoxyacetamide and gives a mixture of compounds. Further purification of this mixture by flash chromatography using 5% MeOH in CHCl$_3$ as eluent affords 157 mg of the title compound.

Physical characteristics are as follows: mp 145–146° C.
$^1$H NMR (DMSO-d6) δ 10.35, 9.00, 8.28, 7.74, 7.54, 5.00, 4.75, 4.55, 4.25, 3.94, 2.50, 2.11. Anal Found: C, 47.18; H, 4.28; N, 14.21; S, 12.82.

EXAMPLE 79

N-{[5-(4-{(5S)-5-[(ethanethioylamino)methyl]-2-oxo-1,3-oxazolidin-3-yl}-2-fluorophenyl)-1,3,4-thiadiazol-2-yl]methyl}-2-hydroxyacetamide. (I-A, X$^1$=F, X$^2$=H, R$^1$=CH$_3$CS, R2=HOCH$_2$CONHCH$_2$). Refer to Scheme I

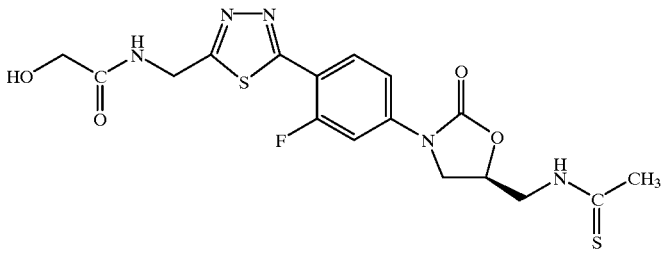

The mixture produced in the first chromatography of Example 78 is further purified by flash chromatography using 5% MeOH in CHCl$_3$ to afford 319 mg of the title compound.

Physical characteristics are as follows: mp 182–184° C.
$^1$H NMR (DMSO-d$_6$) δ 10.40, 8.80, 8.27, 7.73, 7.57, 5.62, 5.00, 4.74, 4.24, 3.90, 2.50. Anal. Found: C, 46.28; H, 4.15; N, 15.88; S, 14.31.

We claim:

1. A compound of formula I:

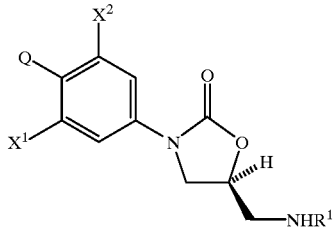

I wherein R¹ is
(a) —COR³,
(b) —COCH₂Cl,
(c) —COCHCl₂,
(d) —COCH₂F,
(e) —COCHF₂,
(f) —CO₂CH₃,
(g) —SO₂CH₃,
(h) —COCH₂OH,
(i) —CSR³,
(j) —CSNH₂, or
(k) —CSNHCH₃;

wherein X¹ and X² are independently
(a) H,
(b) F, or
(c) Cl;

wherein Q is
(a) 1,3,4-thiadiazol-2-yl:

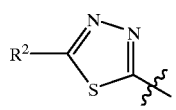

II (b) 1,2,4-thiadiazol-3-yl:

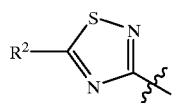

III (c) 1,2,4-thiadiazol-5-yl:

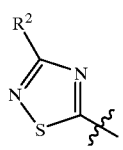

IV (d) 1,2,5-thiadiazol-3-yl:

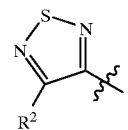

V (e) 1,3,4-oxadiazol-2-yl:

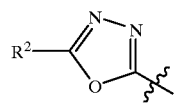

VIII (f) 1,2,4-oxadiazol-3-yl:

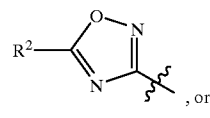

IX

, or (g) 1,2,4-oxadiazol-5-yl

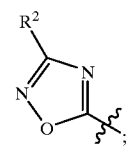

IX-A

;

wherein R² is
(a) R³—
(b) R⁴CO₂(CH₂)ₙ—,
(c) NC(CH₂)ₙ—,
(d) R³OCO(CH₂)ₙ—,
(e) R³R⁵NCO(CH₂)ₙ—,
(f) R³R⁵N(CH₂)ₙ—,
(g) R⁴CONR⁵(CH₂)ₙ—,
(h) CF₃(CH₂)ₙ—,
(i) CF₂H(CH₂)ₙ—,
(j) R⁴CO(CH₂)ₙ—,
(k) F(CH₂)ₙ—,
(l) Cl(CH₂)ₙ—,
(m) Br(CH₂)ₙ—,
(n) R³O(CH₂)ₙ—,
(o) R³S(CH₂)ₙ—,
(p) R³SO(CH₂)ₙ—,
(q) R³SO₂(CH₂)ₙ—,
(r) R³SO₂NR⁵(CH₂)ₙ—,
(s) R³R⁴C(OH)(CH₂)ₙ—,
(t) R³R⁴C(NHR⁵)(CH₂)ₙ—,
(u) HO₂C(CH₂)ₙ—,
(v) O₂N(CH₂)ₙ—,
(w) C₂–C₆ alkenyl,
(x) C₂–C₆ alkynyl,
(y) —CCl₃,
(z) R³ON=CR³(CH₂)ₙ—,
(aa) NCNR⁵(CH₂)ₙ—,
(bb) R³ONR⁵(CH₂)ₙ—, or
(cc) R³OC(O)NR⁵(CH₂)ₙ—;

wherein n is 0, 1, 2, 3, 4 or 5;
wherein p is 1, 2 or 3;
wherein $R^3$ is
(a) H,
(b) $C_1$–$C_5$ alkyl, or
(c) cyclopropyl-;
wherein $R^4$ is
(a) H,
(b) $C_1$–$C_5$ alkyl-,
(c) cyclopropyl-,
(d) $R^3O(CH_2)_p$—, or (e) $R^3CO_2(CH_2)_p$—;
wherein $R^5$ is
(a) H, or
(b) $C_1$–$C_3$ alkyl;
or a pharmaceutically acceptable salt thereof;
with the following proviso:
at least one of $X^1$ and $X^2$ is F or Cl.

2. The compound of claim 1
wherein $R^1$ is
(a) —$COR^3$, or
(b) —$CSR^3$;
wherein $X^1$ and $X^2$ are independently
(a) H, or
(b) F;
wherein Q is the moiety of formula II or IV;
wherein $R^2$ is
(a) $R^3$,
(b) $R^3CO_2(CH_2)_n$—,
(c) $NC(CH_2)_n$—,
(d) $R^3OCO(CH_2)_n$—,
(e) $R^3R^5NCO(CH_2)_n$—,
(f) $R^3R^5N(CH_2)_n$—,
(g) $R^4CONR^5(CH_2)_n$—,
(h) $CF_3(CH_2)_n$—,
(i) $R^4CO(CH_2)_n$—,
(j) $F(CH_2)_n$—,
(k) $Cl(CH_2)_n$—,
(l) $R^3O(CH_2)_n$—,
(m) $R^3S(CH_2)_n$—,
(n) $R^3SO(CH_2)_n$—,
(o) $R^3SO_2(CH_2)_n$—,
(p) $R^3SO_2NR^5(CH_2)_n$—,
(q) $O_2N(CH_2)_n$—, or
(r) $R^3R^4C(NHR^5)(CH_2)_n$—;
(o) $R^3SO_2NR^3(CH_2)_n$—,
(p) $R^3R^4C(OH)(CH_2)_n$—, or
(q) $C_2$–$C_6$ alkenyl;
wherein n is 0, 1, or 2;
wherein $R^4$ is
(a) H,
(b) $C_1$–$C_3$ alkyl, or
(c) cyclopropyl.

3. The compound of claim 2
wherein $R^2$ is
(a) $R^3$,
(b) $NC(CH_2)_n$—,
(c) $R^3NHCO(CH_2)_n$—,
(d) $R^4CO(CH_2)_n$—,
(e) $F(CH_{-2})_n$—,
(g) $Cl(CH_2)_n$—,
(h) $R^3O(CH_2)_n$—,
(i) $R^3S(CH_2)_n$—,
(j) $R^3NH(CH_2)_n$—, or
(k) $R^4CONH(CH_2)_n$—.

4. The compound of claim 3 wherein Q is the moiety of formula II.

5. The compound of claim 1 selected from the group consisting of:
1. (S)-N-[[3-[4(5-Cyano-1,3,4-thiadiazol-2-yl)-3-fluorophenyl]-2-oxo-5-oxazolidinyl]-methyl]acetamide;
2. (S)-5-[4-[5-[(Acetylamino)methyl]-2-oxo-3-oxazolidinyl]-2-fluorophenyl]-1,3,4-thiadiazole-2-carboxamide;
3. (S)-N-[[3-[3-Fluoro-4(5-methyl-1,3,4-thiadiazol-2-yl)phenyl]-2-oxo-5-oxazolidinyl]methyl]acetamide;
4. (S)-N-[[3-[4-(5-Ethyl-1,3,4-thiadiazol-2-yl)-3-fluorophenyl]-2-oxo-5-oxazolidinyl]methyl]acetamide;
5. (S)-N-[[3-[3-Fluoro-4-(5-propyl-1,3,4-thiadiazol-2-yl)phenyl]-2-oxo-5-oxazolidinyl]methyl]acetamide;
6. (S)-N-[[3-[4-[5-(Aminomethyl)-1,3,4-thiadiazol-2-yl]-3-fluorophenyl]-2-oxo-5-oxazolidinyl]methyl]acetamide;
7. S)-N-[[3-[3-Fluoro-4-[5-[[(methylsulfonyl)amino]methyl]-1,3,4-thiadiazol-2-yl]phenyl]-2-oxo-5-oxazolidinyl]methyl]acetamide;
8. (S)-N-[[3-[3-Fluoro-4-(5-fluoromethyl-1,3,4-thiadiazol-2-yl)phenyl]-2-oxo-5-oxazolidinyl]methyl]acetamide;
9. (S)-N-[[3-[3-Fluoro-4-(1,3,4-thiadiazol-2-yl)phenyl]-2-oxo-5-oxazolidinyl]methyl]acetamide;
10. (S)-N-[[3-[4-(5-Acetoxymethyl-1,3,4-thiadiazol-2-yl)-3-fluorophenyl]-2-oxo-5-oxazolidinyl]methyl]acetamide;
11. (S)-N-[[3-[3-Fluoro-4-(5-hydroxymethyl-1,3,4-thiadiazol-2-yl)phenyl]-2-oxo-5-oxazolidinyl]methyl]acetamide;
12. (S)-N-[[3-[3-Fluoro-4-[5-(methoxymethyl)-1,3,4-thiadiazol -2-yl]phenyl]-2-oxo-5-oxazolidinyl]methyl]acetamide;
13. (S)-N-[[3-[4-[5-(Cyanomethyl)-1,3,4-thiadiazol-2-yl]-3-fluorophenyl]-2-oxo-5-oxazolidinyl]methyl]acetamide;
14. (S)-5-[4-[5-[(Acetylamino)methyl]-2-oxo-3-oxazolidinyl]-2-fluorophenyl]-1,3,4-thiadiazole-2-acetamide;
15. (S)-N-[[3-[3-Fluoro-4-[5-(trifluoromethyl)-1,3,4-thiadiazol-2-yl]phenyl]-2-oxo-5-oxazolidinyl]methyl]acetamide;
16. (S)-N-[[3-[3-Fluoro-4-[5-(3-oxobutyl)-1,3,4-thiadiazol-2-yl]phenyl]-2-oxo-5-oxazolidinyl]methyl]acetamide;
17. (5S)-N-[[3-[3-Fluoro-4-[5-(3-hydroxybutyl)-1,3,4-thiadiazol-2-yl]phenyl]-2-oxo5-oxazolidinyl]methyl]acetamide;
18. (S)-Methyl 5-[4-[5-[(acetylamino)methyl]-2-oxo-3-oxazolidinyl]-2-fluorophenyl]-1,3,4-thiadiazole-2-propanoate;
19. (S)-5-[4-[5-[(Acetylamino)methyl]-2-oxo-3-oxazolidinyl]-2-fluorophenyl]-1,3,4-thiadiazole-2-propanamide;
20. (S)-N-[[3-[4-[5-(2-Cyanoethyl)-1,3,4-thiadiazol-2-yl]-3-fluorophenyl]-2-oxo-5-oxazolidinyl]methyl]acetamide;
21. (S)-N-[[3-[3-Fluoro-4-[5-[(methylthio)methyl]-1,3,4-thiadiazol-2-yl]phenyl]-2-oxo-5-oxazolidinyl]methyl]acetamide;
22. (S)-N-[[3-[3-Fluoro-4-[5-[(methylsulfmyl)methyl]-1,3,4-thiadiazol-2-yl]phenyl]-2-oxo-5-oxazolidinyl]methyl]acetamide;

23. (S)-N-[[3-[3-Fluoro-4-[5-[2-(methylthio)ethyl]-1,3,4-thiadiazol-2-yl]phenyl]-2-oxo-5-oxazolidinyl]methyl]acetamide;
24. (S)-N-[[3-[3-Fluoro-4-[5-[2-(methylsulfmyl)ethyl]-1,3,4-thiadiazol-2-yl]phenyl]-2-oxo-5-oxazolidinyl]methyl]acetamide;
25. (S)-Ethyl 5-[4-[5-[(acetylamino)methyl]-2-oxo-3-oxazolidinyl]-2-fluorophenyl]-1,3,4-thiadiazole-2-acetate;
26. (S)-N-[[3-[3-Fluoro-4-[5-(2-hydroxyethyl)-1,3,4-thiadiazol-2-yl]phenyl]-2-oxo-5-oxazolidinyl]methyl]acetamide;
27. (S)-Ethyl 5-[4-[5-[(acetylamino)methyl]-2-oxo-3-oxazolidinyl]-2-fluorophenyl]-1,3,4-thiadiazole-2-carboxylate;
28. (5S)-N-[[3-[3-Fluoro-4-[5-(2-hydroxypropyl)-1,3,4-thiadiazol-2-yl]phenyl]-2-oxo-5-oxazolidinyl]methyl]acetamide;
29. (S)-N-[[3-[4-(4,5-Dihydro-5-oxo-1,3,4-thiadiazol-2-yl)-3-fluorophenyl]-2-oxo-5-oxazolidinyl]methyl]acetamide;
30. (S)-N-[[3-[4-(5-Amino-1,3,4-thiadiazol-2-yl)-3-fluorophenyl]-2-oxo-5-oxazolidinyl]methyl]acetamide;
31. (S)-N-[[3-[3-Fluoro-4-[5-(methylthio)-1,3,4-thiadiazol-2-yl]phenyl]-2-oxo-5-oxazolidinyl]methyl]acetamide;
32. (S)-N-[[3-[3-Fluoro-4-(5-methyl-1,3,4-thiadiazol-2-yl)phenyl]-2-oxo-5-oxazolidinyl]methyl]propanamide;
33. (S)-3-[4-[5-[(Acetylamino)methyl]-2-oxo-3-oxazolidinyl]-2-fluorophenyl]-1,2,4-thiadiazole-5-carboxamide;
34. (S)-N-[[3-[3-Fluoro-4-(1,2,4-thiadiazol-5-yl)phenyl]-2-oxo-5-oxazolidinyl]methyl]acetamide;
35. (S)-N-[[3-[3-Fluoro-4-(5-methyl-1,2,4-oxadiazol-3-yl)phenyl]-2-oxo-5-oxazolidinyl]methyl]acetamide;
36. (S)-N-[[3-[3-Fluoro-4-(1,2,4-oxadiazol-3-yl)phenyl]-2-oxo-5-oxazolidinyl]methyl]acetamide;
37. (S)-3-[4-[5-[(Acetylaniino)methyl]-2-oxo-3-oxazolidinyl]-2-fluorophenyl]-1,2,4-oxadiazole-5-carboxamide;
38. (S)-N-[[3-[4-(5-Cyano-1,2,4-oxadiazol-3-yl)-3-fluorophenyl]-2-oxo-5-oxazolidinyl]methyl]acetamide;
39. (S)-N-[[3-[3-Fluoro-4-[5-(trifluoromethyl)-1,2,4-oxadiazol-3-yl]phenyl]-2-oxo-5-oxazolidinyl]methyl]acetamide;
40. (S)-N-[[3-[3-Fluoro-4-(1,2,4-oxadiazol-5-yl)phenyl]-2-oxo-5-oxazolidinyl]methyl]acetamide;
41. (S)-N-[[3-[3-Fluoro-4-[5-(formylamino)-1,3,4-thiadiazol-2-yl]phenyl]-2-oxo-5-oxazolidinyl]methyl]acetamide;
42. (S)-N-[[3-[4-[5-(2-Chloroethyl)-1,3,4-thiadiazol-2-yl]-3-fluorophenyl]-2-oxo-5-oxazolidinyl]methyl]acetamide;
43. (S)-N-[[3-[3-Fluoro-4-[5-(1-propenyl)-1,3,4-thiadiazol-2-yl]phenyl]-2-oxo-5-oxazolidinyl]methyl]acetamnide;
44. (S)-N-[[3-[4-[5-(2-Aminoethyl)-1,3,4-thiadiazol-2-yl]-3-fluorophenyl]-2-oxo-5-oxazolidinyl]methyl]acetamide;
45. (S)-N-[[3-[4-[5-[2-(Acetylamino)ethyl]-1,3,4-thiadiazol-2-yl]-3-fluorophenyl]-2-oxo-5-oxazolidinyl]methyl]acetamide;
46. (S)-N-[[3-[3-Fluoro-4-[5-[2-[(methylsulfonyl)amino]ethyl]-1,3,4-thiadiazol-2-yl]phenyl]-2-oxo-5-oxazolidinyl]methyl]acetamide;
47. (5S)-N-[[3-[3-Fluoro-4-[5-(methylsulfmyl)-1,3,4-thiadiazol-2-yl]phenyl]-2-oxo-5-oxazolidinyl]methyl]acetamide;
48. (S)-N-[[3-[3-Fluoro-4-[5-(1-methylethyl)-1,3,4-thiadiazol-2-yl]phenyl]-2-oxo-5-oxazolidinyl]methyl]acetamide;
49. (S)-N-[[5-[4-[5-[(Acetylamino)methyl]-2-oxo-3-oxazolidinyl]-2-fluorophenyl]-1,3,4-thiadiazol-2-yl]methyl]acetamide;
50. (S)-N-[[3-[3-Fluoro-4-[5-(3-hydroxypropyl)-1,3,4-thiadiazol-2-yl]phenyl]-2-oxo-5-oxazolidinyl]methyl]acetamide;
51. [S-(R*,R*)]-N-[[3-[3-Fluoro-4-[5-(1-hydroxyethyl)-1,3,4-thiadiazol-2-yl]phenyl]-2-oxo-5-oxazolidinyl]methyl]acetamide;
52. [S-(R*,S*)]-N-[[3-[3-Fluoro-4-[5-(1-hydroxyethyl)-1,3,4-thiadiazol-2-yl]phenyl]-2-oxo-5-oxazolidinyl]methyl]acetamide;
53. (S)-N-[[3-[3-Fluoro-4-[5-(2-nitroethyl)-1,3,4-thiadiazol-2-yl]phenyl]-2-oxo-5-oxazolidinyl]methyl]acetamide;
54. (S)-N-[[3-[3-Fluoro-4-[5-(3-nitropropyl)-1,3,4-thiadiazol-2-yl]phenyl]-2-oxo-5-oxazolidinyl]methyl]acetamide;
55. [S-(R*,R*)]-N-[[3-[4-[5-(1-Aminoethyl)-1,3,4-thiadiazol-2-yl]-3-fluorophenyl]-2-oxo-5-oxazolidinyl]methyl]acetamide;
56. [S-(R*,S*)]-N-[[3-[4-[5-(1-Aminoethyl)-1,3,4-thiadiazol-2-yl]-3-fluorophenyl]-2-oxo-5-oxazolidinyl]methyl]acetamide;
57. (S)-N-[[3-[4-[5-(3-Aminopropyl)-1,3,4-thiadiazol-2-yl]-3-fluorophenyl]-2-oxo-5-oxazolidinyl]methyl]acetamide;
58. (S)-N-[3-[5-[4-[5-[(Acetylanino)methyl]-2-oxo-3-oxazolidinyl]-2-fluorophenyl]-1,3,4-thiadiazol-2-yl]propyl]acetamide;
59. (S)-N-[[3-[4-(5-Acetyl-1,3,4-thiadiazol-2-yl)-3-fluorophenyl]-2-oxo-5-oxazolidinyl]methyl]acetamide;
60. (S)-N-[[3-[4-[5-(3-Chloropropyl)-1,3,4-thiadiazol-2-yl]-3-fluorophenyl]-2-oxo-5-oxazolidinyl]methyl]acetamide;
61. (S)-N-[[3-[4-[5-(3-Cyanopropyl)-1,3,4-thiadiazol-2-yl]-3-fluorophenyl]-2-oxo-5-oxazolidinyl]methyl]acetamide;
62. (S)-N-[[3-[3-Fluoro-4-[5-(methylsulfonyl)-1,3,4-thiadiazol-2-yl]phenyl]-2-oxo-5-oxazolidinyl]methyl]acetamide;
63. (S)-N-[[3-[3-Fluoro-4-[5-[3-(hydroxyimino)butyl]-1,3,4-thiadiazol-2-yl]phenyl]-2-oxo-5-oxazolidinyl]methyl]acetamide;
64. (S)-N-[[3-[3-Fluoro-4-[5-[2-(hydroxyimino)ethyl]-1,3,4-thiadiazol-2-yl]phenyl]-2-oxo-5-oxazolidinyl]methyl]acetamide;
65. (S)-N-[[3-[3-Fluoro-4-[5-[3-(methoxyimino)butyl]-1,3,4-thiadiazol-2-yl]phenyl]-2-oxo-5-oxazolidinyl]methyl]acetamide;
66. (S)-N-[[5-[4-[5-[(Acetyloxyacetylamino)methyl]-2-oxo-3-oxazolidinyl]-2-fluorophenyl]-1,3,4-thiadiazol-2-yl]methyl]acetamide;

67. (S)-N-[[5-[4-[5-[(Hydroxyacetylamino)methyl]-2-oxo-3-oxazolidinyl]-2-fluorophenyl]-1,3,4-thiadiazol-2-yl]methyl]acetamide;
68. (S)-N-[5-[4-[5-[(Acetylamino)methyl]-2-oxo-3-oxazolidinyl]-2-fluorophenyl]-1,3,4-thiadiazol-2-yl]-2-(acetyloxy)acetamide;
69. (S)-N-[[3-[3-Fluoro-4-[5-[(methylsulfonyl)methyl]-1,3,4-thiadiazol-2-yl]phenyl]-2-oxo-5-oxazolidinyl]methyl]acetamide;
70. (S)-N-[[3-[3-Fluoro-4-[5-[2-(methylsulfonyl)ethyl]-1,3,4-thiadiazol-2-yl]phenyl]-2-oxo-5-oxazolidinyl]methyl]acetamide;
71. (S)-N-[[3-[3-Fluoro-4-(1,3,4-thiadiazol-2-yl)phenyl]-2-oxo-5-oxazolidinyl]methyl]propanamide;
72. (S)-N-[[3-[3-Fluoro-4-[5-(2-methoxyethyl)-1,3,4-thiadiazol-2-yl]phenyl]-2-oxo-5-oxazolidinyl]methyl]propanamide;
73. (S)-N-[[3-[3-Fluoro-4-[5-(2-methoxyethyl)-1,3,4-thiadiazol-2-yl]phenyl]-2-oxo-5-oxazolidinyl]methyl]acetamide;
74. (S)-N-[[3-[3-Fluoro-4-(1,3,4-thiadiazol-2-yl)phenyl]-2-oxo-5-oxazolidinyl]methyl]ethanethioamide;
75. (S)-[[3-[3-Fluoro-4-(1,3,4-thiadiazol-2-yl)phenyl]-2-oxo-5-oxazolidinyl]methyl]thiourea;
76. (S)-N-[[3-[3-Fluoro-4-(1,3,4-thiadiazol-2-yl)phenyl]-2-oxo-5-oxazolidinyl]methyl]propanethioamide;
77. N-[((5S)-3-{4-[5-(aminomethyl)-1,3,4-thiadiazol-2-yl]-3-fluorophenyl}-2-oxo-1,3-oxazolidin-5-yl)methyl]ethanethioamide;
78. 2-({[5-(4-{(5S)-5-[(ethanethioylamino)methyl]-2-oxo-1,3-oxazolidin-3-yl}-2-fluorophenyl)-1,3,4-thiadiazol-2-yl]methyl}amino)-2-oxoethyl acetate; and
79. N-{[5-(4-{(5S)-5-[(ethanethioylamino)methyl]-2-oxo-1,3-oxazolidin-3-yl}-2-fluorophenyl)-1,3,4-thiadiazol-2-yl]methyl}-2-hydroxyacetamide.

6. The compound of claim 5 which is
1. (S)-N-[[3-[4-(5-Cyano-1,3,4-thiadiazol-2-yl)-3-fluorophenyl]-2-oxo-5-oxazolidinyl]methyl]acetamide;
2. (S)-N-[[3-[3-Fluoro-4-(5-methyl-1,3,4-thiadiazol-2-yl)phenyl]-2-oxo-5-oxazolidinyl]methyl]acetamide;
3. (S)-N-[[3-[4(5-Ethyl-1,3,4-thiadiazol-2-yl)-3-fluorophenyl]-2-oxo-5-oxazolidinyl]methyl]acetamide;
4. (S)-N-[[3-[4-[5-(Aminomethyl)-1,3,4-thiadiazol-2-yl]-3-fluorophenyl]-2-oxo-5-oxazolidinyl]methyl]acetamide;
5. (S)-N-[[3-[3-Fluoro-4-[5-[[(methylsulfonyl)amino]methyl]-1,3,4-thiadiazol-2-yl]phenyl]-2-oxo-5-oxazolidinyl]methyl]acetamide;
6. (S)-N-[[3-[3-Fluoro-4-(5-fluoromethyl-1,3,4-thiadiazol-2-yl)phenyl]-2-oxo-5-oxazolidinyl]methyl]acetamide;
7. (S)-N-[[3-[3-Fluoro-4-(1,3,4-thiadiazol-2-yl)phenyl]-2-oxo-5-oxazolidinyl]methyl]acetamide;
8. (S)-N-[[3-[4-(5-Acetoxymethyl-1,3,4-thiadiazol-2-yl)-3-fluorophenyl]-2-oxo-5-oxazolidinyl]methyl]acetamide;
9. (S)-N-[[3-[3-Fluoro-4-(5-hydroxymethyl-1,3,4-thiadiazol-2-yl)phenyl]-2-oxo-5-oxazolidinyl]methyl]acetamide;
10. (S)-N-[[3-[4-[5-(Cyanomethyl)-1,3,4-thiadiazol-2-yl]-3-fluorophenyl]-2-oxo-5-oxazolidinyl]methyl]acetamide;
11. (S)-5-[4-[5-[(Acetylamino)methyl]-2-oxo-3-oxazolidinyl]-2-fluorophenyl]-1,3,4-thiadiazole-2-acetamide;
12. (S)-N-[[3-[3-Fluoro-4-[5-(3-oxobutyl)-1,3,4-thiadiazol-2-yl]phenyl]-2-oxo-5-oxazolidinyl]methyl]acetamide;
13. (S)-N-[[3-[4-[5-(2-Cyanoethyl)-1,3,4-thiadiazol-2-yl]-3-fluorophenyl]-2-oxo-5-oxazolidinyl]methyl]acetamide;
14. (S)-N-[[3-[3-Fluoro-4-[5-[2-(methylsulfinyl)ethyl]-1,3,4-thiadiazol-2-yl]phenyl]-2-oxo-5-oxazolidinyl]methyl]acetamide;
15. (S)-N-[[3-[3-Fluoro-4-[5-(2-hydroxyethyl)-1,3,4-thiadiazo 1-2-yl]phenyl]-2-oxo-5-oxazolidinyl]methyl]acetamide;
16. (S)-N-[[3-[4-(4,5-Dihydro-5-oxo-1,3,4-thiadiazol-2-yl)-3-fluorophenyl]-2-oxo-5-oxazolidinyl]methyl]acetamide;
17. (S)-N-[[3-[3-Fluoro-4-[5-(methylthio)-1,3,4-thiadiazol-2-yl]phenyl]-2-oxo-5-oxazolidinyl]methyl]acetamide;
18. (S)-N-[[3-[3-Fluoro-4-(5-methyl-1,3,4-thiadiazol-2-yl)phenyl]-2-oxo-5-oxazolidinyl]methyl]propanamide;
19. (5S)-N-[[3-[3-Fluoro-4-[5-(methylsulfinyl)-1,3,4-thiadiazol-2-yl]phenyl]-2-oxo-5-oxazolidinyl]methyl]acetamide;
20. (S)-N-[[3-[3-Fluoro-4-[5-(3-hydroxypropyl)-1,3,4-thiadiazol-2-yl]phenyl]-2-oxo-5-oxazolidinyl]methyl]acetamide;
21. [S-(R*,R*)]-N-[[3-[3-Fluoro-4-[5-(1-hydroxyethyl)-1,3,4-thiadiazol-2-yl]phenyl]-2-oxo-5-oxazolidinyl]methyl]acetamide
22. [S-(R*,S*)]-N-[[3-[3-Fluoro-4-[5-(1-hydroxyethyl)-1,3,4-thiadiazol-2-yl]phenyl]-2-oxo-5-oxazolidinyl]methyl]acetamide;
23. (S)-N-[[3-[3-Fluoro-4-[5-(2-nitroethyl)-1,3,4-thiadiazol-2-yl]phenyl]-2-oxo-5-oxazolidinyl]methyl]acetamide;
24. (S)-N-[[3-[3-Fluoro-4-[5-(3-nitropropyl)-1,3,4-thiadiazol-2-yl]phenyl]-2-oxo-5-oxazolidinyl]methyl]acetamide;
25. [S-(R*,R*)]-N-[[3-[4-[5-(1-Aminoethyl)-1,3,4-thiadiazol-2-yl]-3-fluorophenyl]-2-oxo-5-oxazolidinyl]methyl]acetamide;
26. [S-(R*,S*)]-N-[[3-[4-[5-(1-Aminoethyl)-1,3,4-thiadiazol-2-yl]-3-fluorophenyl]-2-oxo-5-oxazolidinyl]methyl]acetamide;
27. (S)-N-[[3-[4-[5-(3-Cyanopropyl)-1,3,4-thiadiazol-2-yl]-3-fluorophenyl]-2-oxo-5-oxazolidinyl]methyl]acetamide;
28. (S)-N-[[3-[3-Fluoro-4-[5-[3-(hydroxyimino)butyl]-1,3,4-thiadiazol-2-yl]phenyl]-2-oxo-5-oxazolidinyl]methyl]acetamide;
29. (S)-N-[[3-[3-Fluoro-4-[5-[2-(hydroxyimino)ethyl]-1,3,4-thiadiazol-2-yl]phenyl]-2-oxo-5-oxazolidinyl]methyl]acetamide;
30. (S)-N-[[3-[3-Fluoro-4-[5-[2-(methylsulfonyl)ethyl]-1,3,4-thiadiazol-2-yl]phenyl]-2-oxo-5-oxazolidinyl]methyl]acetamide;
31. (S)-N-[[3-[3-Fluoro-4-(1,3,4-thiadiazol-2-yl)phenyl]-2-oxo-5-oxazolidinyl]methyl]propanamide;
32. (S)-N-[[3-[3-Fluoro-4-(1,3,4-thiadiazol-2-yl)phenyl]-2-oxo-5-oxazolidinyl]methyl]ethanethioamide;

33. (S)-[[3-[3-Fluoro-4-(1,3,4-thiadiazol-2-yl)phenyl]-2-oxo-5-oxazolidinyl]methyl]thiourea;
34. (S)-N-[[3-[3-Fluoro-4-(1,3,4-thiadiazol-2-yl)phenyl]-2-oxo-5-oxazolidinyl]methyl]propanethioamide;
35. N-[((5S)-3-{4-[5-(aminomethyl)-1,3,4-thiadiazol-2-yl]-3-fluorophenyl}-2-oxo-1,3-oxazolidin-5-yl)methyl]ethanethioamide;
36. 2-({[5-(4-{(5S)-5-[(ethanethioylamino)methyl]-2-oxo-1,3-oxazolidin-3-yl}-2-fluorophenyl)-1,3,4-thiadiazol-2-yl]methyl}amino)-2-oxoethyl acetate; or
37. N-{[5-(4-{(5S)-5-[(ethanethioylamino)methyl]-2-oxo-1,3-oxazolidin-3-yl}-2-fluorophenyl)-1,3,4-thiadiazol-2-yl]methyl}-2-hydroxyacetamide.

* * * * *